(12) United States Patent
Choi et al.

(10) Patent No.: US 12,398,371 B2
(45) Date of Patent: Aug. 26, 2025

(54) METHOD FOR MASS PRODUCING NATURAL KILLER CELL AND USE OF NATURAL KILLER CELL OBTAINED BY THE METHOD AS ANTI-CANCER AGENT

(71) Applicant: KOREA RESEARCH INSTITUTE OF BIOSCIENCE, Daejeon (KR)

(72) Inventors: In Pyo Choi, Daejeon (KR); Suk Ran Yoon, Daejeon (KR); Sooyun Lee, Daejeon (KR)

(73) Assignee: Korea Research Institute of Bioscience, Daejeon (KR)

( * ) Notice: Subject to any disclaimer, the term of this patent is extended or adjusted under 35 U.S.C. 154(b) by 1367 days.

(21) Appl. No.: 16/811,063

(22) Filed: Mar. 6, 2020

(65) Prior Publication Data

US 2020/0277574 A1    Sep. 3, 2020

Related U.S. Application Data

(63) Continuation-in-part of application No. 15/547,026, filed as application No. PCT/KR2016/000474 on Jan. 15, 2016, now abandoned.

(30) Foreign Application Priority Data

Jan. 27, 2015  (WO) ............... PCT/KR2015/000854

(51) Int. Cl.
| | |
|---|---|
| *A61K 40/15* | (2025.01) |
| *A61K 40/42* | (2025.01) |
| *A61P 35/00* | (2006.01) |
| *C12N 5/0783* | (2010.01) |

(52) U.S. Cl.
CPC ............ *C12N 5/0646* (2013.01); *A61K 40/15* (2025.01); *A61K 40/42* (2025.01); *A61P 35/00* (2018.01); *A61K 2239/31* (2023.05); *A61K 2239/38* (2023.05); *A61K 2239/50* (2023.05); *A61K 2239/53* (2023.05); *A61K 2239/54* (2023.05); *A61K 2239/55* (2023.05); *C12N 2501/2315* (2013.01); *C12N 2501/2321* (2013.01); *C12N 2506/00* (2013.01); *C12N 2509/10* (2013.01)

(58) Field of Classification Search
None
See application file for complete search history.

(56) References Cited

U.S. PATENT DOCUMENTS

| | | |
|---|---|---|
| 2012/0121544 A1 | 5/2012 | Choi et al. |
| 2013/0011376 A1 | 1/2013 | Peled et al. |
| 2014/0023626 A1 | 1/2014 | Peled et al. |
| 2014/0120072 A1 | 5/2014 | Yonemitsu et al. |
| 2015/0152387 A1 | 6/2015 | Lee et al. |

FOREIGN PATENT DOCUMENTS

| | | |
|---|---|---|
| CN | 103923879 A | 7/2014 |
| EP | 1185867 A2 | 3/2002 |
| JP | 2013-532469 A | 8/2013 |
| JP | 2015-502756 A | 1/2015 |
| KR | 10-2010-0045704 A | 5/2010 |
| KR | 10-1077912 B1 | 10/2011 |
| KR | 10-2012-0100207 A | 9/2012 |
| KR | 10-2014-0051263 A | 4/2014 |
| WO | 2010-013947 A2 | 2/2010 |
| WO | 2012/009422 A | 1/2012 |
| WO | 2013/094988 A1 | 6/2013 |
| WO | 2013-168978 A | 11/2013 |

OTHER PUBLICATIONS

Stern et. al. (Bone Marrow Transpl. 2013, 48: 433-438) (Year: 2013).*
Shu et. al. (Progress in Cryopreservation of Stem Cells and Immune Cells for Cytotherapy, 2015, Chapter 2, pp. 23-42) (Year: 2015).*
Romee et.al. (Blood, Dec. 2012, 120(24): 4751-4760) (Year: 2012).*
Lee et al (Blood, 2012, 120(21): 1900, abstract 703, 3 pages) (Year: 2012).*
NIH NCI, definition of monocyte, 2024, 1 page (Year: 2024).*
Horowitz et al (Science TranslationalMedicine.org, 2013, 5(208): 208ra145, pp. 1-11) (Year: 2013).*
CliniMACSTM 2019 (Year: 2019).
RosetteSepTM 2019 (Year: 2019).
CryoStorR Cs10 (2019) (Year: 2019).
Tonn, T. et al.; "Treatment of patients with advanced cancer with the natural killer cell line NK-92"; Cytotherapy; vol. 15, No. 12; 2013, pp. 1563-1570 (8 pages).
Extended European Search Report issued in corresponding European Application No. 16743625.2 dated Jan. 26, 2018 (9 pages).
Office Action issued in corresponding Japanese Application No. 2017-536867 dated May 31, 2018, and English translation thereof (10 pages).
"The proinflammatory cytokines IL-2, IL-15 and IL-21 modulate the repertoire of mature human natural killer cell receptors", Arthritis Research & Therapy, 2007, Vo. 9, R125, pp. 1-15. National Publication of International Patent Application No. 2013-532469 (15 pages), De Rham et al.
Improved Post-Thaw Recovery of Peripheral Blood Stem/ Progenitor Cells Using a Novel Intracellular-like Cryopreservation Solution Cytotherapy: 2009, vol. 11, No. 4, pp. 472-479 (14 pages).

(Continued)

*Primary Examiner* — Misook Yu
*Assistant Examiner* — Marianne Dibrino
(74) *Attorney, Agent, or Firm* — Norris McLaughlin, P.A.

(57) ABSTRACT

Disclosed is a method for producing a large amount of natural killer cells and the use of the natural killer cells as an anticancer agent. The method produces fresh NK cells with high purity within a short time, and can also produce cold-preserved NK cells and thawed cryopreserved NK cells having efficacy comparable to the fresh NK cells. NK cells having efficacy comparable to the fresh NK cells can also be produced from cryopreserved CD3-negative cells. The fresh NK cells, cold-preserved NK cells and cryopreserved NK cells exhibit therapeutic effects against various cancers, including colorectal cancer, lung cancer, liver cancer, pancreatic cancer and leukemia, indicating these NK cells are effective as cellular therapeutic agents. Also disclosed are doses and methods of administration that show excellent effects when the fresh NK cells, cold-preserved NK cells and cryopreserved NK cells are used as pharmaceutical compositions for cellular therapy.

7 Claims, 33 Drawing Sheets

(56) References Cited

OTHER PUBLICATIONS

International Search Report issued in PCT/KR2016/000474 mailed on Apr. 27, 2016 (2 pages).
Written Opinion of the International Searching Authority issued in PCT/KR2016/000474 mailed on Apr. 27, 2016, English translation—16 pages.
International Search Report issued in PCT/KR2015/000854 mailed on Oct. 26, 2015 (3 pages).
Choi, I. et al.; "Donor-Derived Natural Killer Cells Infused after Human Leukocyte Antigen-Haploidentical Hematopoietic Cell Transplantation: A Dose-Escalation Study"; Biology of Blood and Marrow Transplantation, vol. 20, No. 5, 2014, pp. 696-704 (9 pages).
De Maria, A. et al.; "Revisiting human natural killer cell subset function revealed cytolytic CD56dimCD16+ NK cells as rapid producers of abundant IFN-g on activiation"; PNAS, vol. 108, No. 2, Jan. 11, 2011, pp. 728-732 (5 pages).
Di Santo, J.P. et al.; "Natural Killer Cell Developmental Pathways: A Question of Balance"; Annu. Rev. Immunol., vol. 24, 2006, pp. 257-286 (32 pages).
Cooper, M.A. et al.; "The biology of human natural killer-cell subsets"; TRENDS in Immunology, vol. 22, No. 11, Nov. 2001, pp. 633-640 (8 pages).
Itoh, K. et al.; "Lysis of Human Solid Tumor Cells by Lymphokine-Activated Natural Killer Cells"; The Journal of Immunology, vol. 136, No. 10, May 15, 1986, pp. 3910-3915 (6 pages).
Bordignon, C. et al.; "Cell therapy: achievements and perspectives"; Haematologica, vol. 84, 1999, pp. 1110-1149 (40 pages).
Konjević, G. et al.; "Association of NK cell dysfunction with changes in LDH characteristics of peripheral blood lymphocytes (PBL) in breast cancer patients"; Breast Cancer Research and Treatment, vol. 66, 2001, pp. 255-263 (9 pages).
Ryuke, Y. et al.; "Growth inhibition of subcutaneous mouse melanoma and induction of natural killer cells by liposome-mediated interferon-b gene therapy"; Melanoma Research, vol. 13, 2003, pp. 349-356 (8 pages).
Villegas, F.R. et al.; "Prognostic significance of tumor infiltrating natural killer cells subset CD57 in patients with squamous cell lung cancer"; Lung Cancer, vol. 35, 2002, pp. 23-28 (6 pages).
Castriconi, R. et al.; "Human NK cell infusions prolong survival of metastatic human neuroblastoma-bearing NOD/scid mice"; Cancer Immunol Immunother, vol. 56, 2007, pp. 1733-1742 (10 pages).
Dewan, Z., Md. et al.; "Role of natural killer cells in hormone-independent rapid tumor formation and spontaneous metastasis of breast cancer cells in vivo"; Breast Cancer Res. Treat., vol. 104, 2007, pp. 267-275 (9 pages).
Galy, A. et al.; "Human T, B, Natural Killer, and Dendritic Cells Arise from a Common Bone Marrow Progenitor Cell Subset"; Immunity, vol. 3, Oct. 1995, pp. 459-473 (15 pages).
Mrózek, E. et al.; "Role of Interleukin-15 in the Development of Human CD56+ Natural Killer Cells from CD34+ Hematopoietic Progenitor Cells"; Blood, vol. 87, No. 7, Apr. 1, 1996, pp. 2632-2640 (10 pages).
Sivori, S. et al.; "IL-21 induces both rapid maturation of human CD34+ cell precursors towards NK cells and acquisition of surface killer ig-like receptors"; Eur. J. Immunol. vol. 33, 2003, pp. 3439-3447 (9 pages).
Grzywacz, B. et al.; "Coordinated acquisition of inhibitory and activating receptors and functional properties by developing human natural killer cells"; Blood, vol. 108, No. 12, Dec. 1, 2006, pp. 3824-3833 (10 pages).
Disanto, J.P. et al.: "Lymphoid development in mice with a targeted deletion of the interleukin 2 receptor g chain"; Proc. Natl. Acad. Sci. USA, vol. 92, Jan. 1995, pp. 377-381 (5 pages).
Shibuya, A. et al.; "Lymphokine Requirement for the Generation of Natural Killer Cells from CD34+ Hematopoietic Progenitor Cells"; Blood, vol. 85, No. 12, Jun. 15, 1995, pp. 3538-3546 (9 pages).
DiSanto, et al.; J P et "Absence of Interleukin 2 Production in a Severe Combined Immunodeficiency Disease Syndrome with T Cells"; J. Exp. Med., vol. 171, May 1990, pp. 1697-1704 (8 pages).
Ogasawara, K. et al.; "Requirement for IRF-1 in the microenvironment supporting development of natural killer cells"; Nature, vol. 391, Feb. 12, 1998, pp. 700-703 (4 pages).
Leonard, W.J. et al.; "Interleukin-21: A Modulator of Lymphoid Proliferation, Apoptosis and Differentiation"; Nature, vol. 5, Sep. 2005, pp. 688-697 (11 pages).
Takaki, R. et al.; "IL-21 Enhances Tumor Rejection through a NKG2D-Dependent Mechanism"; The Journal of Immunology, vol. 175, 2005, pp. 2167-2173 (7 pages).
Asao, H. et al.; "Cutting Edge: The Common g-Chain is an Indispensable Subunit of the IL-21 Receptor Complex"; The Journal of Immunology, vol. 167, 2001, pp. 1-5 (5 pages).
Parrish-Novak, J. et al.; "Interleukin 21 and its receptor are involved in NK cell expansion and regulation of lymphocyte function"; Nature, vol. 408, Nov. 2, 2000, pp. 57-63 (7 pages).
Strengell, M. et al.; "IL-21 in Synergy with IL-15 or IL-18 Enhances IFN-g Production in Human NK and T Cells"; The Journal of Immunology, vol. 170, 2003, pp. 5464-5469 (6 pages).
Brady, J. et al.; "IL-21 Induces the Functional Maturation of the Murine NK Cells"; The Journal of Immunology, vol. 172, 2004, pp. 2048-2058 (11 pages).
Moroz, A. et al.; "IL-21 Enhances and Sustains CD8+ T Cell Responses to Achieve Durable Tumor Immunity: Comparative Evaluation of IL-2, IL-15, and IL-21"; The Journal of Immunology, vol. 173, 2004, pp. 900-909 (10 pages).
Written Opinion of the International Searching Authority issued in PCT/KR2015/000854 mailed on Oct. 26, 2015 (10 pages).
Koehl, U. et al.; "IL-2 activated NK cell immunotherapy of three children after haploidentical stem cell transplantation"; Blood Cells, Molecules & Diseases, vol. 33, 2004, pp. 261+-266 (6 pages).
PCT/KR2015/000854 published Aug. 4, 20166 English translation, 86 pages.

\* cited by examiner

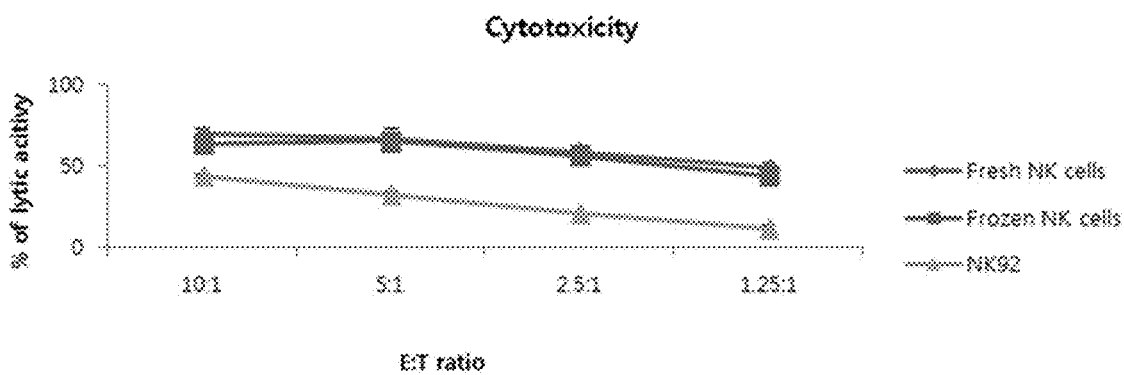
FIG. 2d
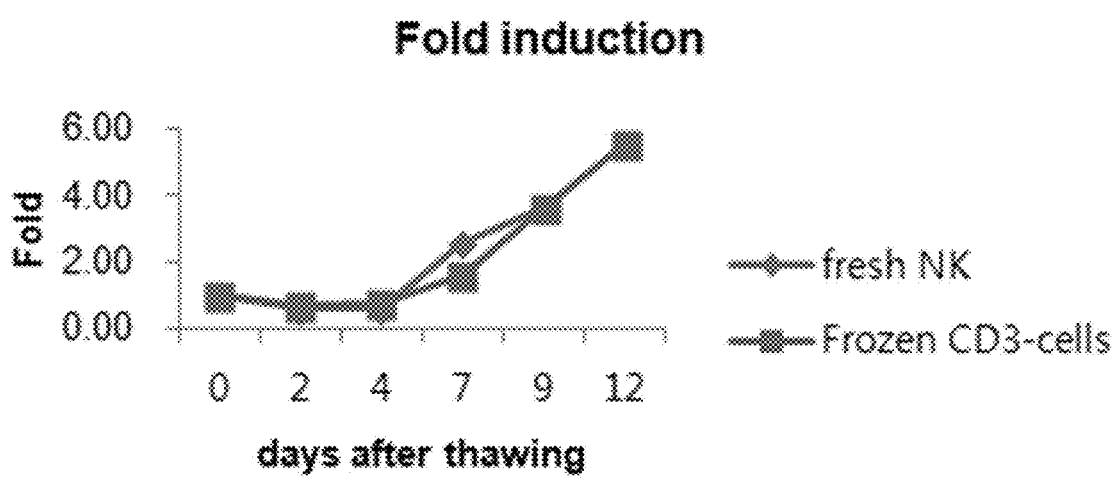
FIG. 2e
FIG. 2f a. Degree of differentiation b. NK receptors (CD94)

1st V.O

1st 3×10$^5$

1st 1×10$^6$

H-E Staining, ×200

1st 3×10$^6$

1st V.O      1st $3\times10^5$      1st $1\times10^6$      1st $3\times10^6$

CD56, x400

| IFN-γDetection | Mean Result | SD |
|---|---|---|
| PB-NK | 49.28 | 1.63 |
| KRIBB-NK(avg) | 619.2 | 18.1 |
| KRIBB-NK1 | 443.5 | 4.04 |
| KRIBB-NK2 | 799.61 | 35.86 |
| KRIBB-NK3 | 614.34 | 14.45 |

METHOD FOR MASS PRODUCING NATURAL KILLER CELL AND USE OF NATURAL KILLER CELL OBTAINED BY THE METHOD AS ANTI-CANCER AGENT

CROSS REFERENCE TO RELATED APPLICATIONS

This application is a continuation-in-part of U.S. patent application Ser. No. 15/547,026, filed Jul. 27, 2017, now pending, which is a 371 of PCT/KR2016/000474, filed on Jan. 15, 2016, which, in turn, claims priority of PCT/KR2015/000854, filed Jan. 27, 2015. This application claims the benefit and priority of the prior applications and incorporates their disclosures by reference in their entirety.

FIELD OF THE INVENTION

The present invention relates to a method for producing cryopreserved NK cells and a method of producing NK cells from frozen CD3-negative cells.

BACKGROUND OF THE INVENTION

For tumor treatment, various treatment methods, including surgery, radiotherapy and chemotherapy, have been developed. However, in the case of some tumors, frequent recurrence of the tumors has posed a serious problem. For this reason, the potential of cellular therapy based on patient's immunity has been proposed.

Immune responses that remove tumors are caused by complex interactions between immune cells having various functions. Immune cells that directly remove tumor cells include natural killer cells (hereinafter referred to as NK cells) and cytotoxic T lymphocytes (CTLs), and antigen-presenting cells that present antigens to these effector cells include dendritic cells (DCs) and B cells. In addition to these cells, there are helper T cells, regulatory T cells and the like, which release various cytokines.

Among the cells of the immune cells, NK cells are a type of lymphocytes and are distributed in human bone marrow, spleen, peripheral lymph nodes and peripheral blood, and it is known that about 10% of lymphocytes in the peripheral blood are NK cells (Ann Rev Immunol., 24: 257-286, 2006). NK cells are positive for CD56 and CD16 but negative for CD3. Unlike T-cells, NK cells kill tumor cells and virally infected cells without previous stimulation or MEC restriction, and do not express clonally rearranged receptors (Trends Immunol., 22: 633-640, 2001). NK cell-mediated apoptosis is associated with the release of cytoplasmic granules containing perform and granzyme and pathways including FasL and TRAIL. NK cells release various cytokines, particularly IFN-γ, INF-α, GM-CSF and IL-10, and express various receptors on the cell surface, and these receptors are involved in cell adhesion, activation of cytotoxicity, or inhibition of cytotoxicity. Furthermore, NK cells recognize MEC class I molecules via KIRs (killer immunoglobulin-like receptors), and most KIRs are killing inhibitory receptors. When such inhibitory receptors are not recognized as MEC molecules, cell killing will occur.

Based on this cytotoxicity of NK cells, new cellular therapies have been attempted either to treat solid tumors using lymphokine activated killer cells (LAK) and tumor infiltration lymphocytes (TILs) or to perform immunotherapy through donor lymphocyte infusion (Tilden. A. B. et al, *J. Immunol.*, 136: 3910-3915, 1986; Bordignon C. et al., *Hematologia*, 84: 1110-1149, 1999) to thereby prevent rejection from occurring in bone marrow implantation or organ transplantation. In addition, it was reported that the defect in NK cell differentiation and activity is related to various cancer diseases, including breast cancer (Konjevic G. et al., *Breast Cancer Res. Treat.*, 66: 255-263, 2001), melanoma (Ryuke Y. et al., *Melanoma Res.*, 13: 349-356, 2003), and lung cancer (Villegas F R., et al., *Lung Cancer,* 35: 23-28, 2002). Thus, to treat such diseases, NK cell therapy is attracting attention.

Most NK cells present in vivo in a normal state are present in an inactivated state. However, to use NK cells for actual therapeutic applications, activated NK cells are required. For this reason, studies on activation of NK cells from normal blood or inactivated patient's blood have been actively conducted.

High NK cell cytotoxicity achieved by in vitro activation of NK cells demonstrated the cellular immunotherapy potential of NK cells. It was reported that NK cells activated in vitro exhibit therapeutic effects against various types of cancer, particularly blood cancer such as leukemia, when they are administered after allogenic bone marrow transplantation (*Blood Cells Molecules & Disease,* 33: 261-266, 2004). However, the clinically distinct therapeutic effect of NK cells against solid cancers other than blood cancer has not yet been demonstrated. Specifically, it was reported that administration of NK cells before development of a tumor can interfere with engraftment of the tumor (*Cancer Immunol. Immunother.,* 56(11): 1733-1742, 2007), but it hardly appears to be a suitable therapeutic model. In addition, there are animal study results indicating that intraperitoneal administration of NK cells inhibited the growth of breast cancer cells, but it is unclear whether this effect results from NK cells (*Breast Cancer Res. Treat.,* 104(3): 267-275, 2007).

In addition, in order to effectively use NK cells for anticancer cellular immunotherapy, it is required to obtain a large number of NK cells. However, because NK cells account for 10-15% of lymphocytes in blood and the number, differentiation and function of NK cells in cancer patients are often reduced, it is difficult to actually obtain a sufficient number of NK cells. Accordingly, it is urgently required to obtain a large amount of NK cells by proliferation or differentiation of NK cells.

It is known that NK cells are derived from hematopoietic stem cells (HSCs). Methods for inducing differentiation into NK cells were reported which comprise isolating hematopoietic stem cells from umbilical cord blood in vitro and treating and culturing the isolated cells with suitable cytokines to thereby induce differentiation into NK cells (Galy et al., *Immunity* 3: 459-473, 1995; Mrozek E, et al., *Blood* 87:2632-2640, 1996; Sivori, S. et al., *Eur J Immunol.* 33:3439-3447, 2003; B. Grzywacz, et al., *Blood* 108: 3824-3833, 2006). Specifically, these methods may comprise adding Flt-3L, IL-7, SCF and IL-15 to $CD34^+$ HSCs and culturing the HSCs for 5 weeks to induce differentiation into $CD3^-CD56^+$ NK cells. However, such differentiation methods have shortcomings in that it is difficult to obtain a sufficient amount of cells for treatment and in that much time and cost are required, indicating that these methods are difficult to apply to actual clinical practice.

It is known that, in mice deficient in expression of $\gamma_c$ of cytokine receptors, B cells and T cells are found but NK cells are not found, indicating that receptors having $\gamma_c$ play an important role in NK cell differentiation (Singer, B et al., *Proc. Natl. Acad. Sci. USA* 92, 377-381, 1995). The $\gamma_c$ forms of receptor include IL-2, IL-4, IL-7, IL-9, IL-15 and IL-21 receptors, and among them, IL-2 was reported to function to promote the proliferation and activation of mature NK cells (Shibuya, A. et al., *Blood* 85, 3538-3546, 1995). It was reported that the number of NK cells in IL-2-deficient humans and mice significantly decreases (DiSanto, J. P. et al., *J Exp. Med.* 171, 1697-1704, 1990), but there are also study results indicating that deficiency of IL-2 and IL-2Ra has an indirect effect on the number and activation of NK cells. In addition, IL-2R (IL-2 receptor) chains are involved in formation of IL-15 receptor.

IL-15 is involved in NK cell differentiation, as demonstrated by the fact that mice lacking interferon-regulating factor-1 (IRF-1) that is transcription factor required for IL-15 production lack NK cells (Kouetsu et al., *Nature* 391, 700-703, 1998) and that NK cells are not found in mice lacking IL-15 or IL-15Ra. Thus, it was reported that IL-15 directly promotes the growth and differentiation of NK cells by the IL-15 receptor that is expressed in NK cells (MrozekE et al., *Blood* 87, 2632-2640, 1996).

IL-21 is a cytokine which is secreted by activated $CD4^+$ T cells (*Nature*, 5:688-697, 2005), and the IL-21 receptor (IL-21R) is expressed in lymphocytes such as dendritic cells, NK cells, T cells and B cells (Rayna Takaki, et al., *J. Immunol* 175: 2167-2173, 2005). IL-21 is structurally very similar to IL-2 and IL-15, and IL-21R shares a chain with IL-2R, IL-15, IL-7R and IL-4R (Asao et al., *J. Immunol,* 167: 1-5, 2001). It was reported that IL-21 induces the maturation of NK cell progenitors from bone marrow (Parrish-Novak, et al., *Nature,* 408: 57-63, 2000). Particularly, it was reported that IL-21 increases the effector functions (such as cytokine-producing ability and apoptotic ability) of NK cells (M. Strengell, et al., *J Immunol,* 170: 5464-5469, 2003; J. Brady, et al., *J Immunol,* 172: 2048-2058, 2004), and that IL-21 also increases the effector functions of $CD8^+$ T cells, thereby promoting the anticancer responses of innate and adaptive immune systems (Rayna Takaki, et al., *J Immunol* 175: 2167-2173, 2005; A. Moroz, et al., *J Immunol,* 173: 900-909, 2004). Furthermore, it was reported that IL-21 activates NK cells isolated from human peripheral blood (Parrish-Novak, et al., *Nature,* 408: 57, 2000), and plays an important role in inducing mature NK cells from hematopoietic stem cells isolated from umbilical cord blood (J. Brady, et al., *J Immunol,* 172: 2048, 2004).

KR20140051263A discloses a method for producing an optimum number of NK cells for a cell therapy by amplifying the NK cells from collected blood cells, including the steps of cultivating in the culture medium and removing the CD3 positive cells.

Meanwhile, despite the potential of the above-described cells as cancer therapeutic agents, the number of NK cells present in vivo is not large. For this reason, in order to use such NK cells as cancer therapeutic agents, a technology is necessarily required which produces NK cells in large amounts enabling the sufficient efficacy of NK cells to be maintained in vivo. However, there is a problem in that in vitro proliferation and culture of a large amount of NK cells are not properly achieved. For this reason, it has been required to develop a technology for culturing and proliferating NK cells at an actually useful level, and many studies on this development have been conducted.

However, a clinically applicable level has not yet been achieved.

SUMMARY OF THE INVENTION

Disclosure

Technical Problem

Accordingly, the present inventors have conducted studies to develop a method for producing a large amount of NK cells in a more efficient and economical manner. As a result, the present inventors have found that, when CD3-negative cells obtained by removing CD3-positive T cells from monocytes are treated with cytokines such as IL-15 and IL-21 and then cultured, a large amount of highly pure NK cells can be produced within a short time compared to conventional NK cell production methods, and that fresh NK cells produced by this method of the present invention inhibit the growth of cancer cells in mouse models xenografted with colorectal cancer, lung cancer, liver cancer and pancreatic cancer cell lines, reduce the weight of cancer cells in the mouse models, and also exhibit their therapeutic effects in blood cancer such as leukemia, indicating that the NK cells produced by the method of the present invention can be used as a pharmaceutical composition for preventing or treating cancer. Furthermore, the present inventors have identified the dose of NK cells and a method for administration of NK cells in treatment of actual cancer patients with NK cells produced by the method of the present invention.

In addition, the present inventors have found that cold-preserved NK cells and cryopreserved NK cells exhibit anticancer effects comparable with fresh NK cells depending on conditions where fresh NK cells are cold-preserved or cryopreserved, and have also identified the dose of NK cells and a method for administration of NK cells in each of the case in which cold-preserved NK cells are used alone, the case in which cryopreserved NK cells are used alone, and the case in which cold-preserved NK cells or cryopreserved NK cells are used in a mixture with fresh NK cells.

In addition, the present inventors have found that fresh NK cells can be produced by thawing cryopreserved CD3-negative cells depending on conditions where CD3-negative cells are cryopreserved.

Technical Solution

The present disclosure provides a method for producing fresh NK cells, the method comprising the steps of:
1) obtaining CD3-negative cells by removing CD3-positive T cells from monocytes; and
2) obtaining cultured CD3-negative cells by treating the CD3-negative cells of step 1) with IL-15 and IL-21, wherein step 1) is performed by allowing the CD3-positive T cells to crosslink to erythrocytes and then isolating the CD3-negative cells by density-gradient centrifugation.

In the present disclosure, the isolation of the CD3-negative cells by density-gradient centrifugation by allowing the CD3-positive T cells to crosslink to erythrocytes in step 1) may be performed using an antibody that uses the CD3-negative cells. For example, the isolation of the CD3-negative cells may be performed using the product ROSETTESEP™ Human NK Cell Enrichment Cocktail (manufactured and marketed by STEMCELL Technologies Inc.). The above product is a cocktail of tetrameric antibody complexes recognizing CD3, CD4, CD19, CD36, CD66b, CD123 and glycophorin A. CD3 positive cells, CD4 positive cells, CD19 positive cells, CD36 positive cells, CD66b positive cells and CD123 positive cells bind to the tetrameric antibody complexes together with erythrocytes expressing glycophorin A to form cross-links. When centrifugation is then performed, the cells form a pellet by density gradient, and a medium comprising a high concentration of CD3-negative NK cells can be obtained from the upper layer portion.

In an embodiment of the present disclosure, the culturing in step 2) may be performed at a cell concentration of $1 \times 10^6$ cells/ml, but this cell concentration may be properly determined by those skilled in the art such that it causes no abnormalities in the morphology and activity of the cells.

In one embodiment of the present disclosure, the culturing in step 2) may be performed for 10-24 days, but the culture period may be determined by confirming that the cultured cells show a characteristic of CD3$^-$CD56$^+$.

In one embodiment of the present disclosure, the culturing in step 2) may be performed at a cell concentration of $1\times10^6$ cells/ml.

In one embodiment of the present disclosure, the culturing in step 2) may be performed for 10-24 days.

In the method, the culturing in step 2) may be performed using a stationary culture or suspension culture method. As used herein, the term "stationary culture" means that cells are cultured in an incubator without agitating or shaking, and the term "suspension culture" means that cells are cultured in a suspended state by aeration or agitation such that the cells are not attached to the bottom or side portion of the reactor. Furthermore, the reactor for stationary culture and the reactor for suspension culture may be the same or different. For example, when the reactor for stationary culture and the reactor for suspension culture are the same, stationary culture is completed in the same reactor and then a medium containing necessary nutrient components such as cytokine may additionally be supplied to the same reactor, followed by suspension culture. When different reactors are used, the cultured cells after stationary culture may be transferred into the reactor for suspension culture.

In the present disclosure, the fresh NK cells may be CD3$^-$CD56$^+$.

In the present disclosure, the NK cells are preferably derived from umbilical cord blood, bone marrow or peripheral blood monocytes, but any type of cells may be used as progenitor, as long as they are CD3-negative cells.

The present disclosure provides a pharmaceutical composition for preventing or treating cancer comprising the fresh NK cells produced by the above-described method, as an active ingredient.

In the present disclosure, the pharmaceutical composition means a "cellular therapeutic agent". As used herein, the term "cellular therapeutic agent" refers to cells and tissues prepared by isolation from an individual, culture and special operations, and means a pharmaceutical product (US FDA regulations) which is used for the purposes of treatment, diagnosis and prevention and which is obtained through a series of actions, including growing and screening living autologous or allogenic cells in vitro in order to restore the structure and function of the cells or changing the biological characteristics of cells by any other methods.

In the present disclosure, the cancer is not limited as long as it is a cancer that can be treated with NK cells. For example, the cancer may be any one selected from the group consisting of liver cancer, lung cancer, colorectal cancer, breast cancer, prostate cancer, ovarian cancer, pancreatic cancer, cervical cancer, thyroid cancer, laryngeal cancer, leukemia, brain tumor, neuroblastoma, retinoblastoma, head and neck cancer, salivary gland cancer, and lymphoma. Preferably, the cancer may be any one cancer selected from the group consisting of colorectal cancer, lung cancer, liver cancer, pancreatic cancer, and leukemia.

In one embodiment of the present disclosure, the composition may comprise $1\times10^5$ or more, $3\times10^5$ or more, $3\times10^6$ or more, $1\times10^6$ or more, $3\times10^6$ or more, $6\times10^6$ or more, or $1\times10^7$ or more fresh NK cells.

In one embodiment of the present disclosure, the composition may further comprise IL-2.

In the present disclosure, the composition may be administered at intervals of 14-42 days, preferably 14-35 days, more preferably 14-30 days. However, the interval of administration is not limited thereto.

In one embodiment of the present disclosure, the composition may be administered once a week for 4 weeks, or may be administered twice a week for 2 weeks.

In one embodiment of the present disclosure, the composition may comprise $3\times10^6$ fresh NK cells and may be administered once a week for 4 weeks.

In another embodiment of the present disclosure, the composition may comprise $3\times10^6$ fresh NK cells and may be administered twice a week for 2 weeks.

In another embodiment of the present disclosure, the composition may comprise $6\times10^6$ fresh NK cells and may be administered once a week for 2 weeks.

The present disclosure also provides a method for producing cold-preserved NK cells, the method comprising the steps of:
1) obtaining CD3-negative cells by removing CD3-positive T cells from monocytes; and
2) obtaining cultured CD3-negative cells by treating the CD3-negative cells of step 1) with IL-15 and IL-21,
3) preserving the cultured CD3-negative cells at 4° C. for 15 hours or less,
wherein step 1) is performed by allowing the CD3-positive T cells to crosslink to erythrocytes and then isolating the CD3-negative cells by density-gradient centrifugation.

In the present disclosure, the CD3-negative cells in step 3) may be preserved for 15 hours or less, for example, 12 hours or more, for example, 10 hours or less. However, the preservation time is not limited thereto.

In the present disclosure, the cold-preserved NK cells may be CD3$^-$CD56$^+$.

The present disclosure also provides a pharmaceutical composition for preventing or treating cancer comprising cold-preserved NK cells produced by the above-described method, as an active ingredient.

In the present disclosure, the cancer may be any one cancer selected from the group consisting of colorectal cancer, lung cancer, liver cancer, pancreatic cancer, and leukemia. However, the kind of cancer is not limited thereto, and may be any cancer that can be prevented, alleviated or treated with NK cells.

In one embodiment of the present disclosure, the composition may comprise $1\times10^5$ or more, $3\times10^5$ or more, $3\times10^6$ or more, $1\times10^6$ or more, $3\times10^6$ or more, $6\times10^6$ or more, or $1\times10^7$ or more cold-preserved NK cells.

In one embodiment of the present disclosure, the composition may further comprise IL-2.

In the present disclosure, the composition may be administered at intervals of 14-42 days, preferably 14-35 days, more preferably 14-30 days. However, the interval of administration is not limited thereto.

In one embodiment of the present disclosure, the composition may be administered once a week for 4 weeks, or may be administered twice a week for 2 weeks.

In one embodiment of the present disclosure, the composition may comprise $3\times10^6$ cold-preserved NK cells and may be administered once a week for 4 weeks.

In another embodiment of the present disclosure, the composition may comprise $3\times10^6$ cold-preserved NK cells and may administered twice a week for 2 weeks.

In another embodiment of the present disclosure, the composition may comprise $6\times10^6$ cold-preserved NK cells and may administered once a week for 2 weeks.

The present invention also provides a method for producing cryopreserved NK cells, the method comprising the steps of:
1) obtaining CD3-negative cells by removing CD3-positive T cells from monocytes; and
2) obtaining cultured CD3-negative cells by treating the CD3-negative cells of step 1) with IL-15 and IL-21,
3) freezing the cultured CD3-negative cells of step 2) in a cryopreservation medium containing 10% DMSO (dimethyl sulfoxide) under serum-free, protein-free and animal component-free conditions for 2 months or less, wherein the freezing is performed by stepwise cooling from −70° C. to −200° C.

As used herein, the term "freezing" means an operation of freezing the NK cells of the present invention. The freezing may be performed using various freezing media. For example, the freezing may be performed using a cryopreservation box containing isopropyl alcohol. However, the freezing may also be performed using other means. In addition, in order to prevent damage to the cells during the freezing, a solution containing a cryoprotective agent may be used. As used herein, the term "cryoprotective agent" refers to a substance which is added to a medium for the purpose of reducing frost damage when living biological cells are preserved in a frozen state. The cryoprotective agent that may be used in the present invention may be glycerol, sugar, glucose or the like, but is not particularly limited thereto.

In one embodiment of the present invention, the freezing period may be performed for 2 months or less, preferably 6 weeks or less, more preferably 1 month or less. However, the freezing period is not limited thereto, and may be suitably adjusted within a range in which the effect of the cryopreserved NK cells is maintained.

In one embodiment of the present disclosure, the concentration of the CD3-negative cells in step 3) may be 1.5× cells/ml, but is not limited thereto.

The present disclosure also provides a method for producing thawed cryopreserved NK cells, the method comprising the steps of:

A method for producing thawed cryopreserved NK cells, the method comprising the steps of:
1) obtaining CD3-negative cells by removing CD3-positive T cells from monocytes; and
2) obtaining cultured CD3-negative cells by treating the CD3-negative cells of step 1) with IL-15 and IL-21,
3) obtaining cryopreserved NK cells by freezing the cultured CD3-negative cells of step 2) in a cryopreservation medium containing 10% DMSO (dimethyl sulfoxide) under serum-free, protein-free and animal component-free conditions for 2 months or less, wherein the freezing is performed by stepwise cooling from −70° C. to −200° C.; and
4) quick thawing the cryopreserved NK cells at 37° C., and washing out the cryopreservation medium.

As used herein, the term "thawing" refers to an operation that increases the temperature of the cryopreserved NK cells to room temperature so as to enable the cells to exhibit normal physiological activity during use.

In the present invention, the thawed cryopreserved NK cells may be CD3−.

The present disclosure also provides a pharmaceutical composition for preventing or treating cancer comprise thawed cryopreserved NK cells produced by the above-described method, as an active ingredient.

In the present disclosure, the cancer may be any one cancer selected from the group consisting of colorectal cancer, lung cancer, liver cancer, pancreatic cancer, and leukemia. However, the kind of cancer is not limited thereto, and may be any cancer which can be prevented, alleviated or treated with NK cells.

In one embodiment of the present disclosure, the composition may comprise $1\times10^5$ or more, $3\times10^5$ or more, $3\times10^6$ or more, $1\times10^6$ or more, $3\times10^6$, $6\times10^6$ or more, or $1\times10^7$ or more thawed cryopreserved NK cells.

In one embodiment of the present disclosure, the composition may further comprise distilled water or serum-free medium.

In one embodiment of the present disclosure, the composition may further comprise IL-2.

In the present disclosure, the composition may be administered at intervals of 14-42 days, preferably 14-35 days, more preferably 14-30 days. However, the administration interval is not limited thereto.

In one embodiment of the present disclosure, the composition may be administered once a week for 4 weeks, or may be administered twice a week for 2 weeks, or may be administered twice a week for 4 weeks.

In one embodiment of the present disclosure, the composition may comprise $3\times10^6$ NK thawed cryopreserved cells, and may be administered once a week for 4 weeks.

In another embodiment of the present disclosure, the composition may comprise $3\times10^6$ NK thawed cryopreserved cells, and may be administered twice a week for 2 weeks.

In another embodiment of the present disclosure, the composition may comprise $6\times10^6$ thawed cryopreserved NK cells, and may be administered once a week for 2 weeks.

The present invention also provides a method of producing NK cells from frozen CD3-negative cells, the method comprising the steps of:
1) obtaining CD3-negative cells by removing CD3-positive T cells from monocytes; and
2) obtaining frozen CD3-negative cells by freezing the obtained CD3-negative cells of step 1) in a cryopreservation medium containing 10% DMSO (dimethyl sulfoxide) under serum-free, protein-free and animal component-free conditions for 2 months or less, wherein the freezing is performed by stepwise cooling from −70° C. to −200° C.;
3) obtaining thawed CD3-negative cells by thawing the frozen CD3-negative cells of step 2); and
4) obtaining cultured CD3-negative cells by treating the CD3-negative cells of step 3) with IL-15 and IL-21.

In the present invention, the NK cells produced from frozen CD3-negative cells by the above-described method have the same properties and effects as those of fresh NK cells. Thus, the NK cells produced from frozen CD3-negative cells may be used as an active ingredient in a composition for preventing or treating cancer, in the same manner as fresh NK cells.

The present disclosure also provides a pharmaceutical composition for preventing or treating cancer comprising the fresh NK cells and thawed NK cells produced according to the above-described methods of the present invention, as an active ingredient.

In one embodiment of the present disclosure, each of the fresh NK cell and the thawed NK cells may be comprised in a single dose in an amount of $1\times10^5$ or more cells, $3\times10^5$ or more cells, $3\times10^6$ or more cells, $1\times10^6$ or more cells, $3\times10^6$ or more cells, $6\times10^6$ or more cells, or $1\times10^7$ or more cells.

In one embodiment of the present disclosure, the fresh NK cell and the thawed NK cells may be administered once a week for 4 weeks, or administered twice a week for 2 weeks, or administered twice a week for 4 weeks. Preferably, the fresh NK cells may be administered once a week for 1 week, and the thawed cryopreserved NK cells may be administered twice a week for 3 weeks. However, the administration method may be suitably adjusted.

The pharmaceutical composition of the present disclosure may be prepared using a pharmaceutically suitable and physiologically acceptable adjuvant in addition to the active ingredient. The adjuvant may be one or more of an excipient, a disintegrating agent, a sweetener, a binder, a coating agent, a swelling agent, a lubricant and a flavoring agent.

For administration, the composition of the present disclosure may be formulated to comprise one or more pharmaceutically acceptable carriers in addition to the above-described active ingredient. The pharmaceutically acceptable carriers include saline, sterile water, Ringer's solution, buffered saline, dextrose solution, malto-dextrin solution, glycerol, ethanol, liposome and a mixture of one or more of these components. If necessary, the composition of the present disclosure may comprise other conventional additives, including antioxidants, buffers, and bacteriostatic agents. In addition, a diluent, a dispersing agent, a surfactant, a binder and a lubricant may further be added to the composition of the present disclosure to thereby prepare an injectable formulation such as an aqueous solution, a suspension or an emulsion, or a pill, capsule, granule or tablet formulation. Furthermore, a target organ-specific antibody or ligand bound to the carrier may be used so that the composition can act specifically in the target organ. Furthermore, the composition of the present disclosure may be preferably formulated by a suitable method known in the art or a method disclosed in Remington's Pharmaceutical Science (the latest edition, Mack Publishing Company, Easton PA) to prepare formulations suitable for each disease or component.

The pharmaceutical composition of the present disclosure may be provided as a liquid, suspension, dispersion, emulsion, gel, injectable solution or sustained-release formulation of the active ingredient. Preferably, the composition of the present disclosure may be formulated as an injectable solution.

If the pharmaceutical composition of the present disclosure is formulated as an injectable solution, it may be prepared as a physically or chemically very stable injectable solution by adjusting the pH with an aqueous acid solution or a buffer such as phosphate, which may be used for injection, in order to ensure the stability of the injectable formulation during distribution.

More specifically, the injectable formulation may be prepared by dissolving the composition in injectable water together with a stabilizer or a dissolution aid, and then sterilizing the solution by high-temperature sterilization under reduced pressure or by sterile filtration. The injectable water may be injectable distilled water or an injectable buffer, for example, phosphate buffered saline (pH 3.5 to 7.5) or sodium dihydrogen phosphate ($NaH_2PO_4$)-citrate buffer. The phosphate used may be in the form of sodium salt, potassium salt, anhydride or hydrate, and may also be in the form of citrate, anhydride or hydrate.

Furthermore, the stabilizer that is used in the present disclosure comprises sodium pyrosulfite, sodium bisulfite ($NaHSO_3$), sodium metabisulfite ($Na_2S_2O_3$) or ethylenediaminetetraacetic acid, and the dissolution aid comprises a base such as sodium hydroxide (NaOH), sodium hydrogen carbonate ($NaHCO_3$), sodium carbonate ($NaCO_3$) or potassium hydroxide (KOH), or an acid such as hydrochloric acid (HCl) or acetic acid ($CH_3COOH$).

The injectable formulation according to the present disclosure can be prepared to be bioabsorbable, biodegradable, biocompatible. "Bioabsorbable" means that the injectable formulation is capable of disappearing from its initial application site in the body, with or without degradation of the dispersed injectable formulation. "Biodegradable" means that the injectable formulation is capable of breaking down or degrading within the body, by hydrolysis or enzymatic degradation. Biocompatible means that all of the components are nontoxic in the body.

The injectable formulation according to the present disclosure may be prepared using conventional diluents including fillers, extenders, binders, wetting agents and surfactants or excipients.

The composition or active ingredient of the present disclosure may be administered using a conventional method by an intravenous, intra-arterial, intraperitoneal, intramuscular, intrasternal, transdermal, intranasal, subcutaneous, intrauterine, inhalation, topical, intrarectal, oral, intraocular or intradermal route depending on the intended use. Preferably, it may be administered intravenously. The composition or active ingredient of the present disclosure may be administered by injection or catheter.

In the composition of the present disclosure, the dose of the active ingredient may be adjusted within the range of $1\times10$ to $1\times10^{50}$ cells/kg, preferably $1\times10$ to $1\times10^{30}$ cells/kg, more preferably $1\times10^5$ to $1\times10^{20}$ cells/kg, most preferably $1\times10^7$ to $1\times10^9$ cells/kg, for an adult weighing 60 kg. However, the optimal dose can be easily determined by those skilled in the art, and may vary depending on various factors, including the kind of disease, the severity of the disease, the contents of the active ingredient and other components in the composition, the type of the formulation, and the patient's age, body weight, general health condition, sex and diet, the time of administration, the route of administration, the secretion rate of the composition, the time period of treatment, and a particular drug which is used in combination with the composition.

In the composition of the present disclosure, the active ingredient may be contained in an amount of 0.001-50 wt % based on the total weight of the composition. However, the content of the active ingredient is not limited thereto.

The composition of the present disclosure may further contain one or more anticancer agents.

The present disclosure provides a method for preventing or treating cancer, comprising administering a therapeutically effective amount of the fresh NK cells to subjects in need of cancer treatment.

In the present disclosure, the subjects in need of cancer treatment may be mammals, including humans. For examples, the subjects may be humans, dogs, cats, horses or the like.

The present disclosure provides a method for preventing or treating cancer, comprising administering a therapeutically effective amount of the cryopreserved NK cells to subjects in need of cancer treatment.

The present disclosure provides a method for preventing or treating cancer, comprising administering a therapeutically effective amount of the thawed cryopreserved NK cells to subjects in need of cancer treatment.

As used herein, the term "therapeutically effective amount" refers to the amount of the active ingredient or pharmaceutical composition that evokes a biological or pharmaceutical response within an animal or human subject, and is an amount that is determined by researchers, veterinarians, doctors or other clinicians. The therapeutically effective amount includes an amount that leads to alleviation of symptoms of the disease or disorder to be treated. It is obvious to those skilled in the art that the therapeutically effective amount of the active ingredient and the number of administrations of the active ingredient according to the present disclosure can vary depending on the desired effect.

The present disclosure provides the use of the fresh NK cells for preparing a medicament for cancer treatment.

The present disclosure provides the use of the cold-preserved NK cells for preparing a medicament for cancer treatment.

The present disclosure provides the use of the thawed cryopreserved NK cells for preparing a medicament for cancer treatment.

Advantageous Effects

The use of the methods of the present invention can produce fresh NK cells with high purity within a short time compared to conventional method, and can also produce cold-preserved NK cells and thawed cryopreserved NK cells, which have efficacy comparable with that of the fresh NK cells. Furthermore, it can produce NK cells, which have efficacy comparable with that of the fresh NK cells, from cryopreserved CD3-negative cells.

The fresh NK cells, cold-preserved NK cells and cryopreserved NK cells produced by the methods of the present invention can exhibit therapeutic effects against various cancers, including colorectal cancer, lung cancer, liver cancer, pancreatic cancer and leukemia, indicating that these NK cells can be effectively used as cellular therapeutic agents.

In addition, the present inventors have established doses and methods of administration, which show excellent effects when the fresh NK cells, cold-preserved NK cells and cryopreserved NK cells of the present invention are used as pharmaceutical compositions for cellular therapy.

The present disclosure provides NK cells exhibiting NK cell receptor expression characteristics as described in FIG. 2C herein.

Specifically, NK cells according to the present disclosure express any one or more NK cell receptors selected from a group consisting of CD122, CD94, NKG2D, CD158a (KIR2DL1), CD158b (KIR2DL2/3), KIR3DL1, NKp46, NKp44 and NKp30.

Specifically, the NK cell according to the present disclosure is a natural killer cell having any one or more characteristics selected from a group consisting of:

a) increase in expression of any one or more selected from a group consisting of NKG2D, NKp30, NKp44, and NKp46 as compared to natural killer cells isolated from peripheral blood;

b) decrease in expression of KIR2DL2/3, KIR3DL1, or a combination thereof as compared to natural killer cells isolated from peripheral blood.

In the present disclosure, the increase and decrease in the expression of the natural killer cell receptors are based on results of mean intensity analysis using FACS. Specifically, % represents a percentage of cells having a positive result with respect to a specific protein among total cells.

The percentage (%) change may be expressed in % as compared to an untreated control. The percentage change may be directly compared with that of a conventional general peripheral blood-derived natural killer cells and the like to provide information on the increase or decrease thereof.

For example, the increase in NKp30 may be expressed in % compared to the untreated control. This percentage change may be directly compared with that of the conventional general natural killer cell, in particular, a conventional general peripheral blood-derived natural killer cell to provide information on the increase or decrease thereof.

In addition, the increased ratio of NKp30 may be expressed in multiples by confirming a ratio of a percentage of an expression of memory-like natural killer cells according to the present disclosure with respect to a percentage of an expression of the conventional general natural killer cells, in particular, the conventional general peripheral blood-derived natural killer cells.

In one example, mean fluorescence intensity (MFI) on C in FIG. 2 provides information about a relative value to an expression intensity of each NK cell receptor.

In the present disclosure, the NK cell may preferably be further characterized by having increase in secretion of IFN-γ, as compared to the natural killer cell isolated from peripheral blood.

As used herein, "the conventional general natural killer cell" refers to an NK cell that is separated from a human body and maintains its characteristics exhibited as it is separated from the human body without being subjected to any additional stimulation process. Specifically, the conventional natural killer cell refers to a natural killer cell that may be obtained by a method of separating a cell having such as CD3 negative and/or CD56 positive characteristics from monocytes and the like such as a conventionally known NK cell separation method. Specifically, the expressions "peripheral blood-derived natural killer cell", "natural killer cells isolated from peripheral blood" and "conventional general peripheral blood-derived natural killer cells" which represent the general NK cells not produced by the method according to the present disclosure mean a natural killer cell that may be obtained by a method of separating a cell having such as CD3 negative and/or CD56 positive characteristics from peripheral blood-derived monocytes and the like such as a conventionally known NK cell separation method. The conventional natural killer cell may refer to an NK cell having only general CD56 positive characteristics as separated by a method of separating only CD56 positive cells from monocytes but may not be limited thereto. This separation method may refer to a conventional CD56-positive cell separation method in which CD56 negative cells are removed but CD56 positive cells are maintained using a CS column and Vario MACS. In other words, the natural killer cell isolated from peripheral blood may be a general cell having CD56$^+$ characteristics as separated from the monocytes of peripheral blood and may be a mature cell whose differentiation is terminated. Generally, the mature cells whose differentiation is terminated may have CD27$^-$ and CD11b$^+$ characteristics. In addition, the mature cells whose differentiation is terminated may have exhibited any one or more characteristics selected from a group consisting of CD56+, CD122+, NKp30+ NKp44+ NKp46+ and KIR+ characteristics.

The present disclosure provides a method for producing NK cells having the above-mentioned characteristics, the method comprising steps of:
1) removing CD3-positive T cells from monocytes to obtain CD3-negative cells; and
2) culturing the CD3-negative cells by treating the CD3-negative cells of step 1) with IL-15 and IL-21;
wherein step 1) is performed by allowing the CD3-positive T cells to crosslink to erythrocytes and then isolating the CD3-negative cells by density-gradient centrifugation; and wherein the treatment in the step 2) does not employ other cytokines other than IL-15 and IL-21.

The NK cell according to the present disclosure is an NK cell expressing any one or more NK cell receptors selected from a group consisting of CD122, CD94, NKG2D, CD158a, CD158b, KIR3DL1, NKp46, NKp44 and NKp30.

More preferably, the NK cell according to the present disclosure may express any one or more selected from the group consisting of CD94, NKG2D, NKp46, NKp44, and NKp30 in a higher degree than the general peripheral blood NK cell expresses. Further, the NK cell according to the present disclosure may express CD158b, (KIR2DL2/3) KIR3DL1 or a combination thereof in a lower degree than the general peripheral blood NK cell expresses.

More specifically, the NK cell according to the present disclosure has a) the characteristic of increase in expression of any one or more selected from the group consisting of NKG2D, NKp30, NKp44, and NKp46, as compared to that of the natural killer cells isolated from peripheral blood.

Specifically, the increase in expression of NKp30 may be at least 5%, 10%, 15%, 20%, 30% or more when compared to the expression of NKp30 in the conventional general natural killer cells (especially, peripheral blood-derived natural killer cells). Specifically, this may mean the increase compared with the natural killer cells isolated from peripheral blood.

Further, the increase in expression of NKp30 may be 1.1 times, 1.2 times, 1.3 times, 1.4 times, 1.5 times, 1.6 times, 1.7 times, 1.8 times, 1.9 times, 2 times, 3 times, 4 times or greater than that of NKp30 in the conventional natural killer cells.

NKp30 is a receptor that increases the killing ability of NK cells. Therefore, the increase in expression thereof has the advantage of enhancing the killing ability.

Specifically, the increase in expression of NKG2D may be at least 5%, 10%, 15%, 20%, 30%, 40%, 50%, 60%, 70%, 90%, or more compared to the expression of NKG2D in conventional general natural killer cells (especially, peripheral blood-derived NK cells). Specifically, this may mean the increase compared with the natural killer cells isolated from peripheral blood.

Further, the increase in expression of NKG2D may be 1.1 times, 1.2 times, 1.3 times, 1.4 times, 1.5 times, 1.6 times, 1.7 times, 1.8 times, 2 times, 3 times or more than that of the NKG2D in the conventional natural killer cells.

NKG2D is one of the receptors for inducing NK cell activity. The activity of the NK cell itself may be enhanced when the activity of NKG2D is increased.

Specifically, the increase in expression of NKp44 may be at least 5%, 10%, 15%, 20%, 30%, 40%, 50%, 60%, 70%, 90%, or more compared to the expression of NKp44 in conventional general natural killer cells (especially, peripheral blood-derived NK cells). Specifically, this may mean the increase compared with the natural killer cells isolated from peripheral blood.

Further, the increase in expression of NKp44 may be 1.1 times, 1.2 times, 1.3 times, 1.4 times, 1.5 times, 1.6 times, 1.7 times, 1.8 times, 2 times, 5 times, 10 times, 15 times, 20 times, 30 times, 40 times, 50 times or greater compared to that of NKp44 in the conventional general natural killer cells.

NKp44 is one of the receptors for inducing NK cell activity and has an advantage in that the activity of NK cells itself may be enhanced if the activity of NKp44 is increased.

Specifically, the increase in an expression of NKp46 may be at least 5%, 10%, 15%, 20%, 30%, 40%, 50%, 60%, 70%, 80%, 90% or more, compared to the expression of NKp46 in conventional general natural killer cells (especially peripheral blood-derived NK cells). Specifically, this may mean the increase compared with the natural killer cells isolated from peripheral blood.

Further, the increase in expression of NKp46 may be 1.1 times, 1.2 times, 1.3 times, 1.4 times, 1.5 times, 1.6 times, 1.7 times, 1.8 times, 2 times, 2.5 times, 3 times, 5 times, 10 times, 20 times, 40 times, 60 times, 80 times, 90 times or more than that of NKp46 in the conventional general natural killer cells.

NKp46 is one of the receptors for inducing NK cell activity and has an advantage in that the activity of NK cells itself maybe enhanced if the activity of NKp46 is increased.

More specifically, the NK cell according to the present disclosure has b) a characteristic of decrease in the expression of KIR2DL2/3 (CD158b), KIR3DL1, or a combination thereof as compared to that of the natural killer cells isolated from peripheral blood.

Specifically, the decrease in the expression of KIR2DL2/3 (CD158b) may be at least 5%, 10%, 15%, 20%, 30% or more compared to the expression of KIR2DL2/3 in conventional general natural killer cells (particularly, peripheral blood-derived NK cells). Specifically, this may mean the decrease compared with the natural killer cells isolated from peripheral blood.

Further, the decrease in the expression of KIR2DL2/3 may be 1.1 times, 1.2 times, 1.3 times, 1.4 times, 1.5 times, 1.6 times, or more than that of the conventional general natural killer cells.

KIR2DL2/3 is one of the receptors for inducing NK cell suppression and has an advantage in that the activity of the NK cell itself may be enhanced if the activity of KIR2DL2/3 is decreased.

Specifically, the decrease in the expression of KIR3DL1 may be at least 5%, 10%, 15%, 20%, 30% or more, when compared to the expression of KIR3DL1 in conventional general natural killer cells (particularly peripheral blood-derived NK cells). Specifically, this may mean the decrease compared with the natural killer cells isolated from peripheral blood.

Further, the decrease in the expression of KIR3DL1 may be 1.1 times, 1.2 times, 1.3 times, 1.4 times, 1.5 times, 1.6 times, or more than that of conventional general natural killer cells.

KIR3DL1 is one of the receptors for inducing NK cell suppression and has an advantage in that the activity of the NK cell itself may be enhanced if the activity of KIR3DL1 is decreased.

NK cells according to the present disclosure as produced according to the production process mentioned in the present disclosure show NK cell receptor expression patterns different from that of the general NK cells, particularly, those with CD56+ characteristics as isolated from peripheral blood using a conventional method.

Infusion of the NK cells may be a treatment method for cancer patients sensitive to NK cell lysis having, for example, hematologic cancer (e.g., acute myeloid leukemia or multiple myeloma) and several solid cancers (e.g., brain tumor, ewing sarcoma, liver cancer and rhabdomyosarcoma), and the like. As the number of functional NK cells increases, the efficacy of the therapeutic antibodies as used in the treatment of several cancers, including lymphomas, colorectal cancer, liver cancer, lung cancer, and breast cancer may also be significantly increased.

The NK cells produced according to the production method in accordance with the present disclosure exhibited different NK cell receptor expression patterns from that of the known cells. Thus, the thus functionally enhanced NK cells may provide excellent anti-cancer effects.

That is, NK cells in accordance with the present disclosure increase the receptors for inducing the NK cell activity to a high level, while inhibiting or minimizing increase in the expression of the receptors for suppressing the NK cell activity. This may maximize the activity of NK cells, and may greatly enhance its functionality.

In particular, NK cells according to the present disclosure having the above characteristics may be further characterized by having increase in the secretion of IFN-γ as compared to that of the natural killer cells isolated from peripheral blood.

The NK cell according to the present disclosure exhibits increase in secretion/expression of IFN-γ as compared to the secretion/expression of IFN-γ in the conventional general natural killer cells, particularly, peripheral blood-derived natural killer cells.

Specifically, the increase in the secretion/expression of IFN-γ may be at least 20%, 30%, 40%, 50%, 60%, 100%, 200%, 300%, 400%, 500%, 1000%, 2000%, 3000% or more compared to that of IFN-γ in the conventional general natural killer cells.

The increase in secretion of IFN-γ may greatly increase the killing ability of the natural killer cells, and may greatly enhance the anti-cancer immune function by stimulating other immune cells in addition to NK cells.

Even if the natural killer cells according to the present disclosure may be frozen, thawed and then used, have an advantage in that the treatment effect thereof may be maintained.

The NK cell according to the present disclosure with the above characteristics shows enhanced killing ability. Specifically, the NK cell according to the present disclosure with the above characteristics shows enhanced killing ability to kill the cancer cells, virally infected cells, or both as compared to that of the natural killer cells isolated from peripheral blood.

The present disclosure provides a method of killing cancer cells using the NK cells having the above-mentioned characteristics.

In particular, the present disclosure provides a method of treating cancer in a subject, the method comprising administering the natural killer cell to the subject in need thereof.

BRIEF DESCRIPTION OF THE DRAWINGS

FIG. 2d show NK cell cytotoxicities.

FIG. 2e shows the cell recovery rate immediately after thawing of NK cells obtained by differentiation of CD3-negative cells thawed after freezing; FIG. 2f shows fold increase in cell number upon culture after thawing.

V.C (5% HSA): vehicle control group.

Figure 3A:
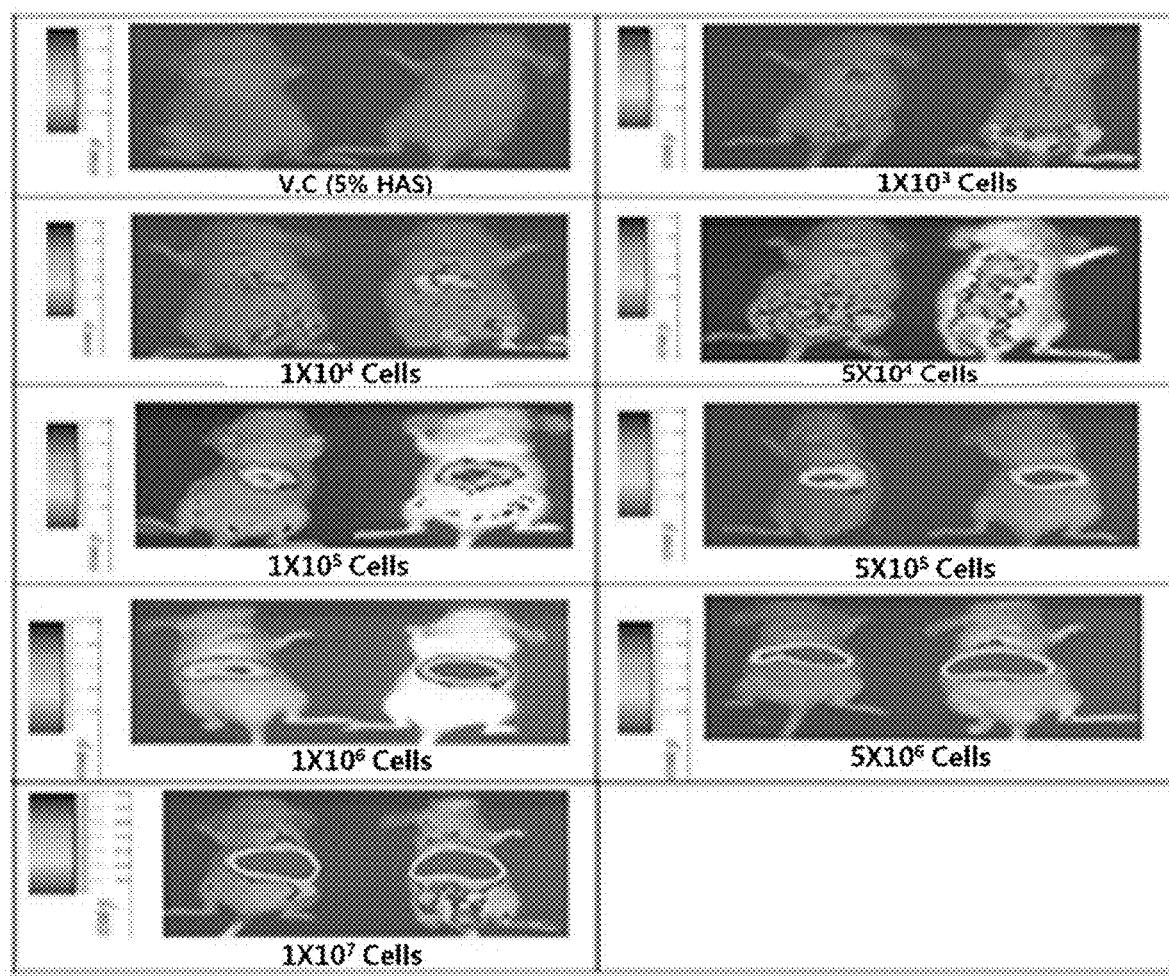
FIG. 3a shows the results of detecting NK cells in mice to measure the concentration-dependent detection limit of NK (natural killer) cells.
Figure 3B:
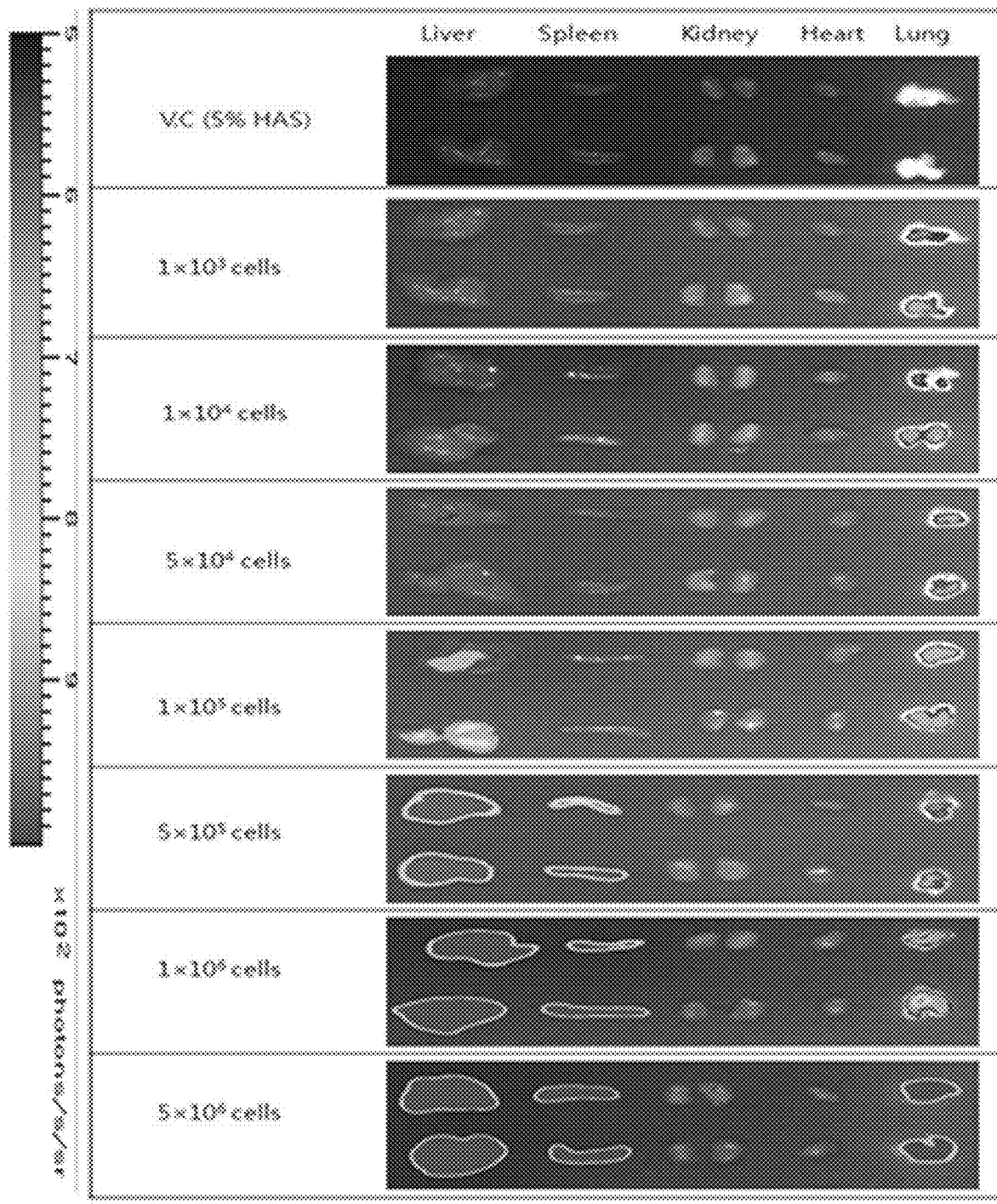

FIG. 3b shows the results of detecting NK cells in the major intra-abdominal organs of mice to measure the concentration-dependent detection limit of NK cells.

V.C (5% HSA): vehicle control group.

Figure 3C:
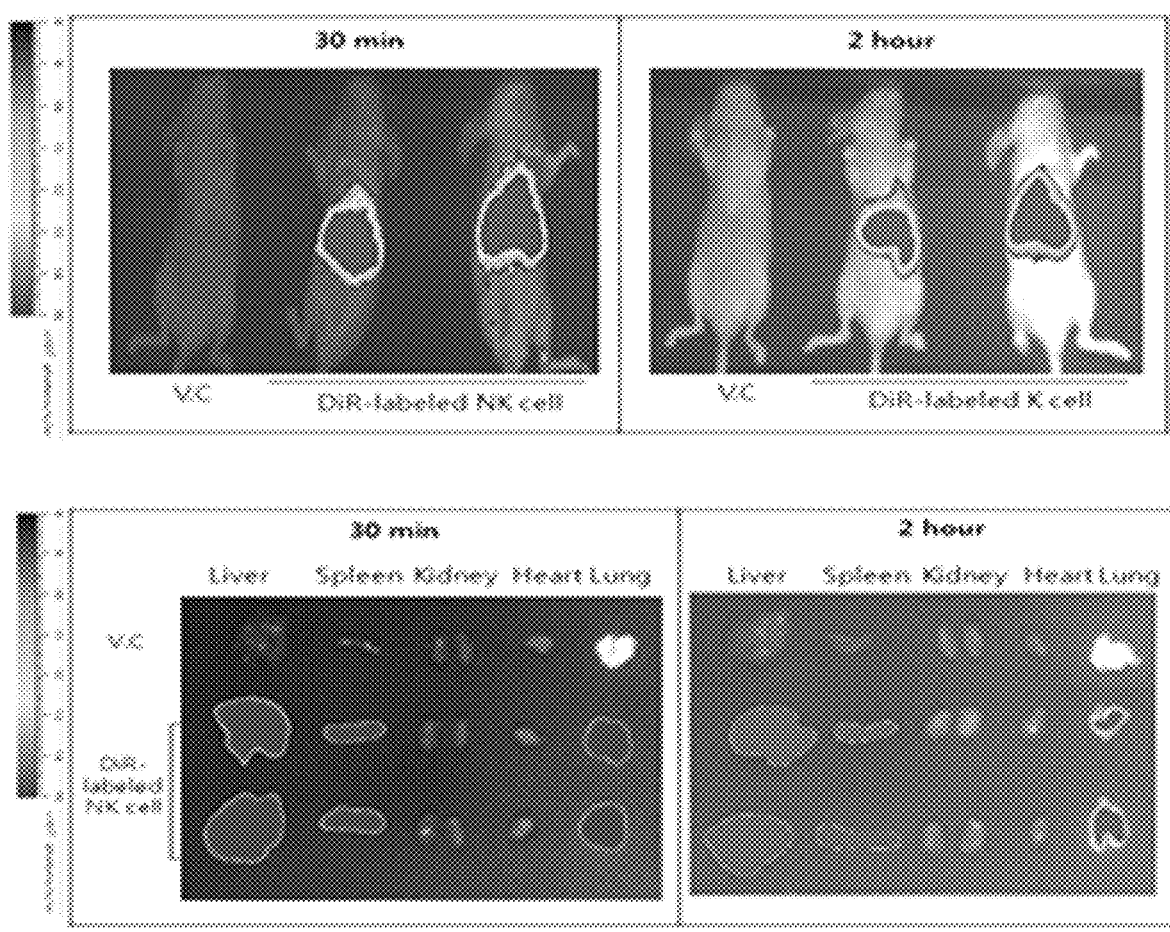

FIG. 3c shows the results of analyzing the distribution of NK cells in the major intra-abdominal organs of mice.

V.C: vehicle control group.

Figure 3D:
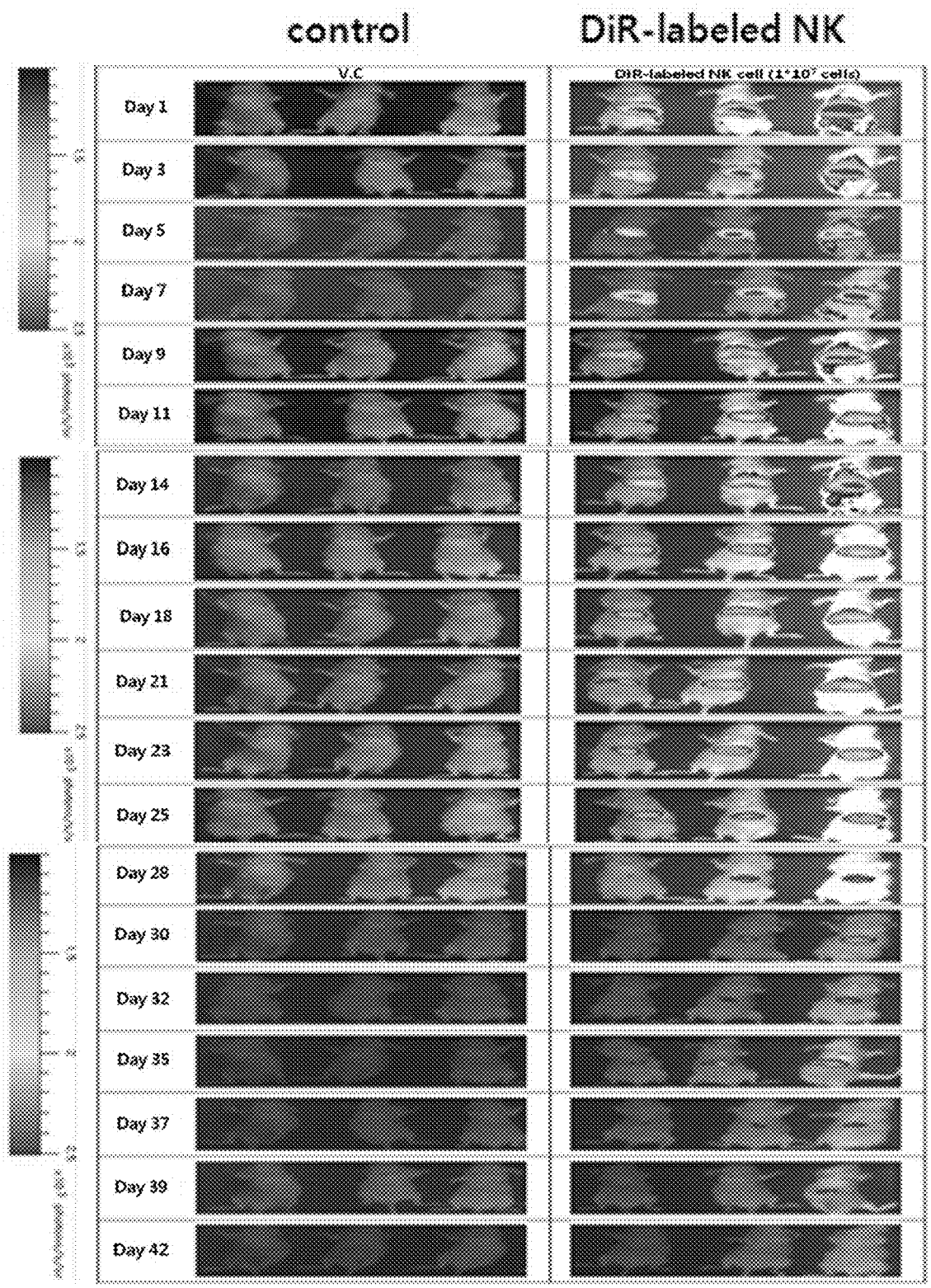

FIG. 3d shows the results of analyzing the in vivo distribution of NK cells in mice at varying time points.

Figure 4A:
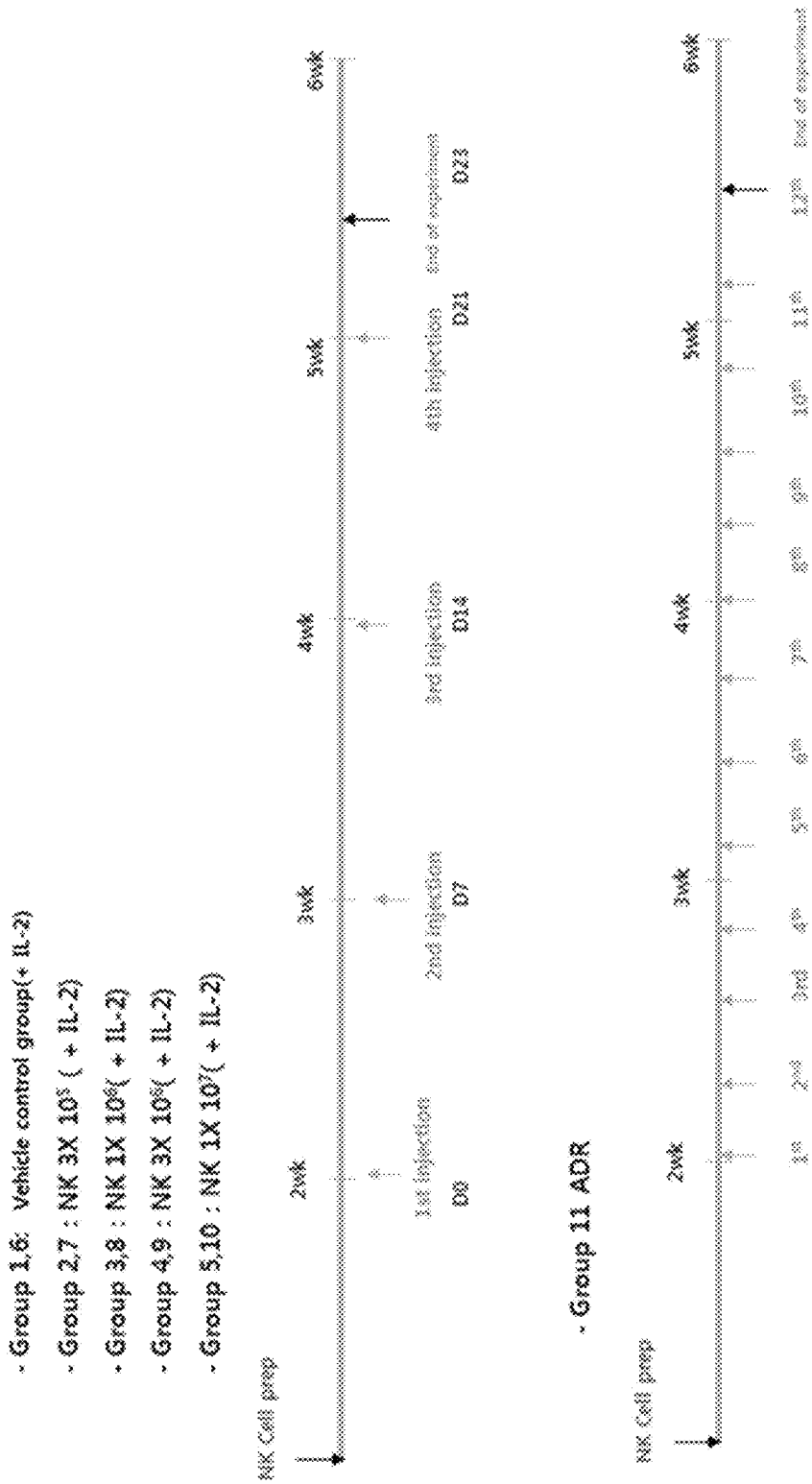

FIG. 4a shows an administration schedule for examining the anticancer effect of NK cells against colorectal cancer.

Figure 4B:
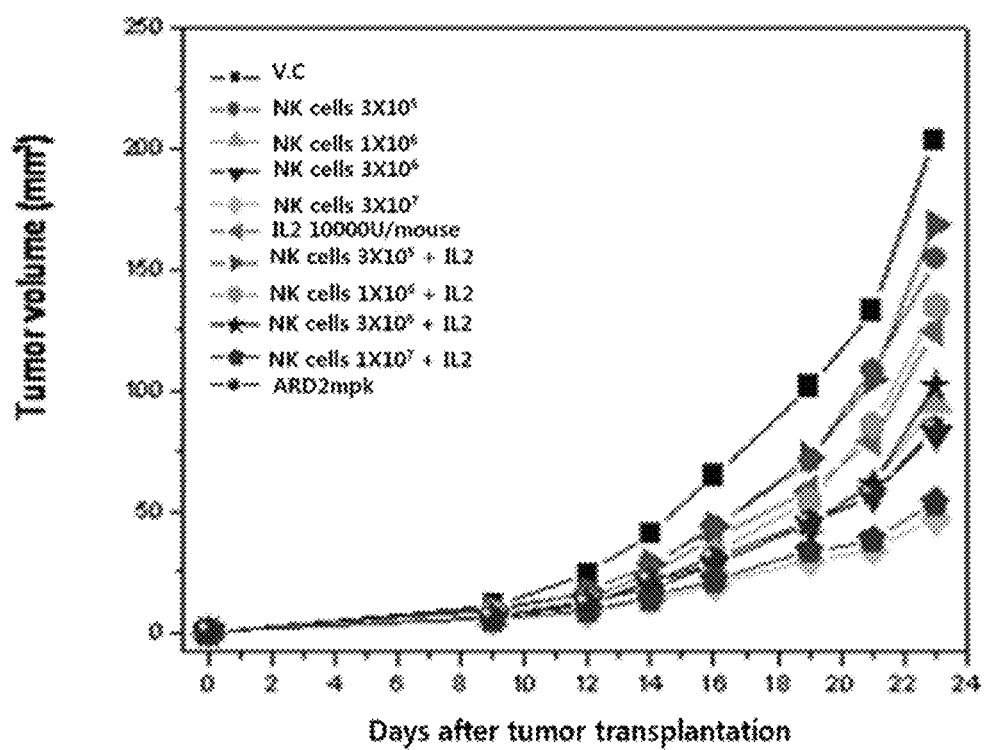

FIG. 4b shows the results of measuring the tumor size inhibitory effect of NK cells alone or in combination with IL-2 against colorectal cancer when varying number of the NK cells are used.

V.C: vehicle control group, and
ADR: adriamycin-treated group.

Figure 4C:
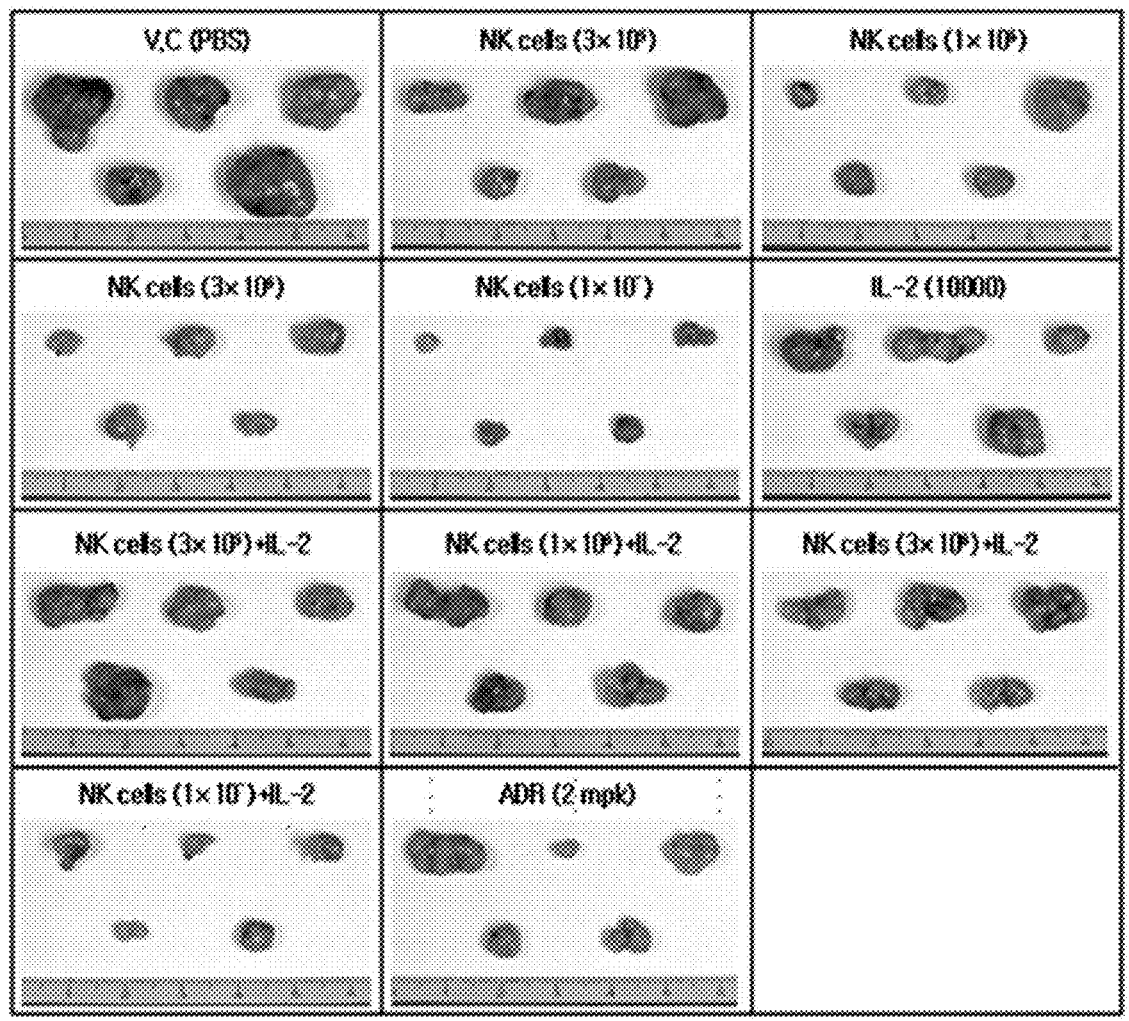

FIG. 4c shows the results of measuring the tumor weight reducing effect of NK cells alone or in combination with IL-2 against colorectal cancer when varying number of the NK cells are used.

V.C: vehicle control group, and
ADR: adriamycin-treated group.

Figure 5A:
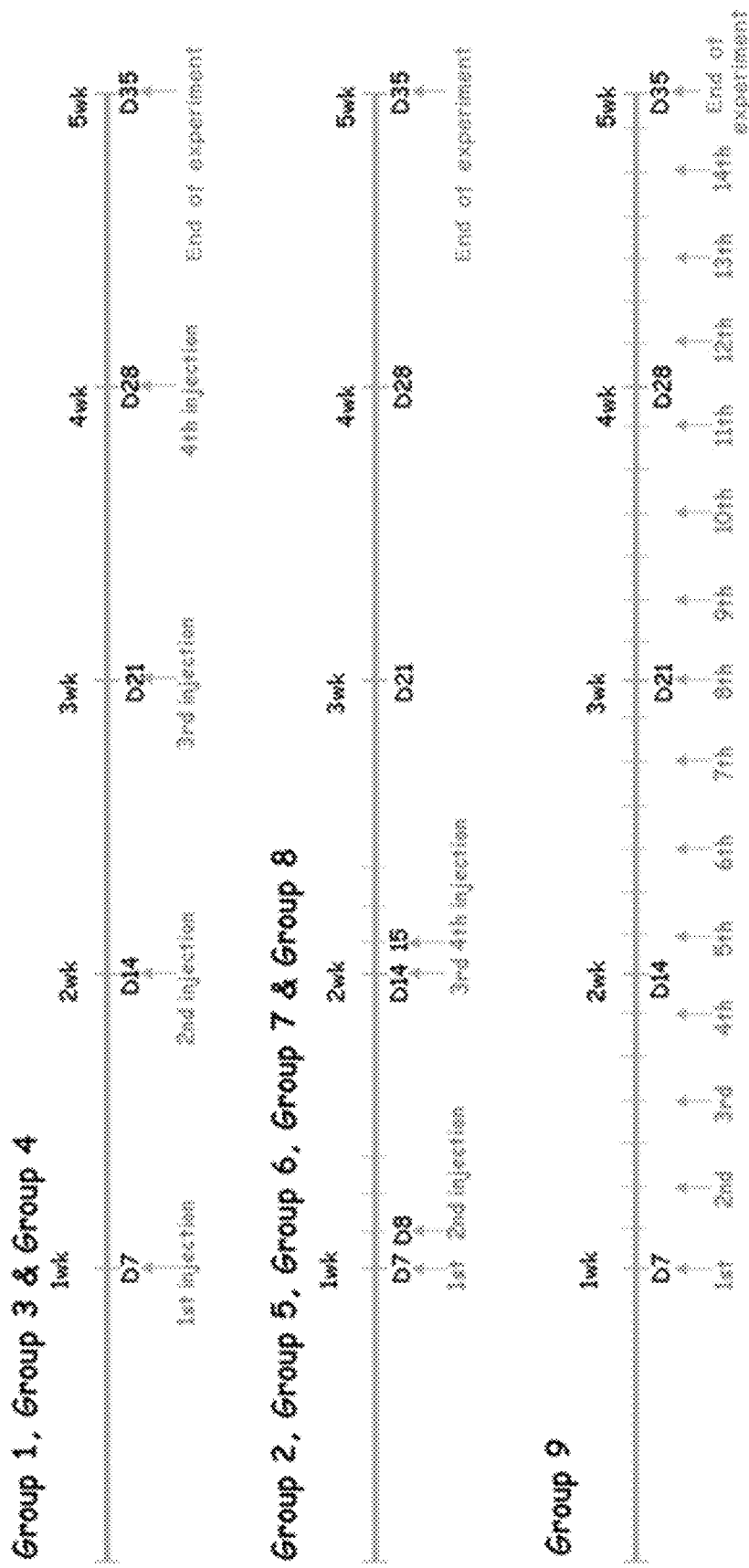

FIG. 5a shows administration schedules prepared to examine anticancer effects according to the culture conditions, preservation conditions and administration schedule of NK cells.

Figure 5B:
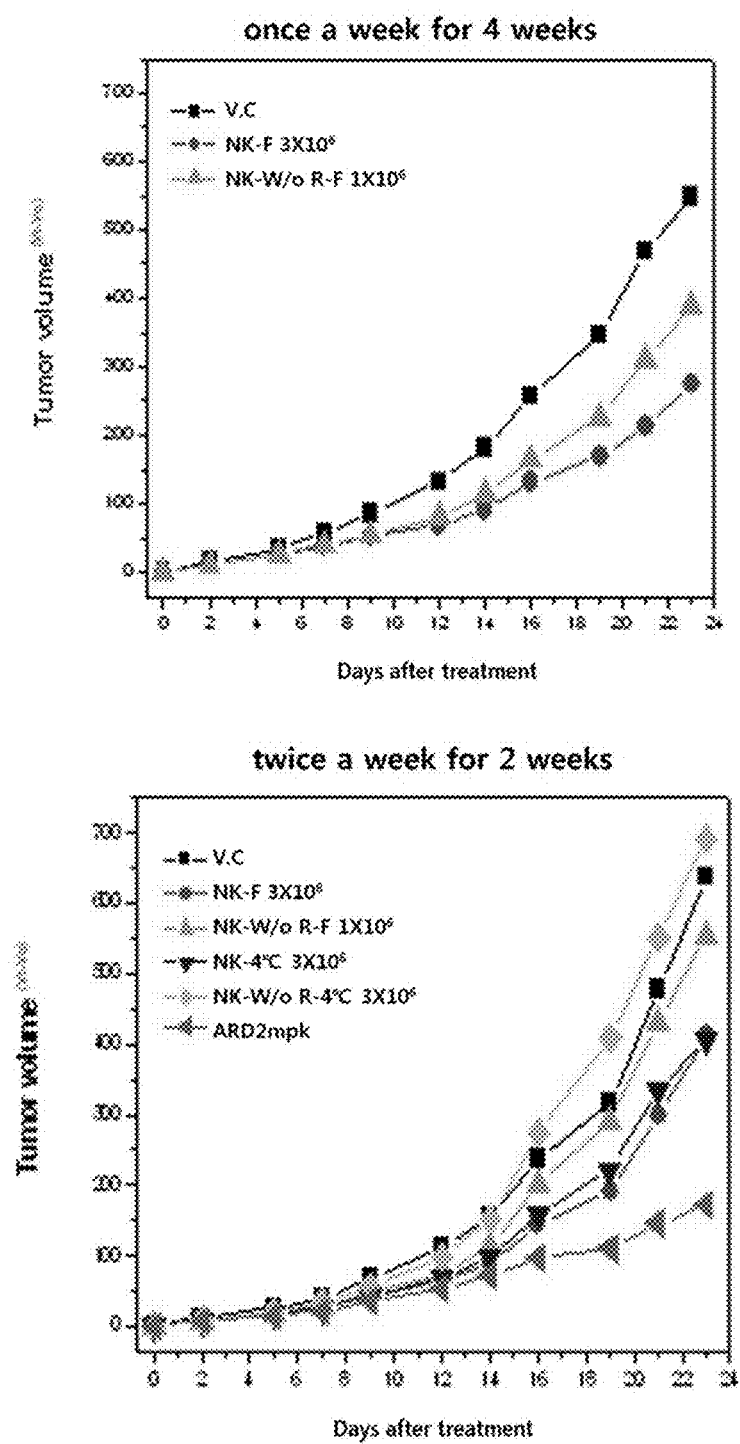

FIG. 5b shows the results of analyzing the tumor volume inhibitory effects of NK cells against colorectal cancer according to the culture conditions, preservation conditions and administration schedule of NK cells.

V.C: vehicle control group;
NK-F: fresh NK cell-treated group;
NK-W/oR-F: group treated with fresh NK cells (ROSETTESEP™-free, that is, w/o ROSETTESEP™);
NK-4° C.: group treated with NK cells cold-preserved at 4° C.;
NK-W/oR-4° C.: group treated with fresh NK cells (ROSETTESEP™-free) cold-preserved at 4° C.;
ADR: adriamycin-treated group.

Figure 5C:
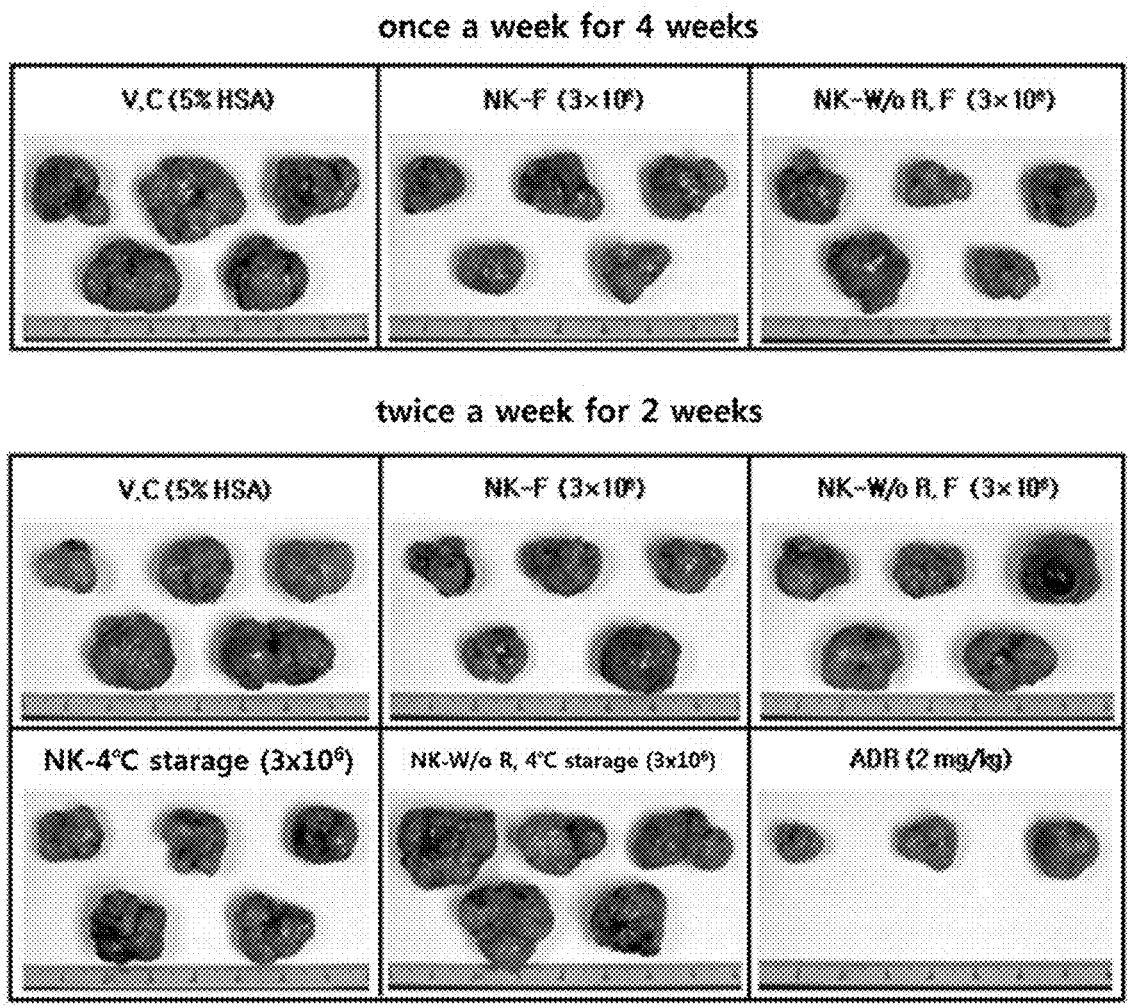

FIG. 5c shows the results of analyzing the tumor weight-reducing effects of NK cells against colorectal cancer according to the culture conditions, preservation conditions and administration schedule of NK cells.

V.C: vehicle control group;
NK-F: group treated with fresh NK cells;
NK-W/oR,F: group treated with fresh NK cells (ROSETTESEP™-free);
NK-4° C. preserved: group treated with NK cells cold-preserved at 4° C.;
NK-W/oR, 4° C. preserved: group treated with fresh NK cells (ROSETTESEP™-free) cold-preserved at 4° C.;
ADR: adriamycin-treated group.

Figure 6A:
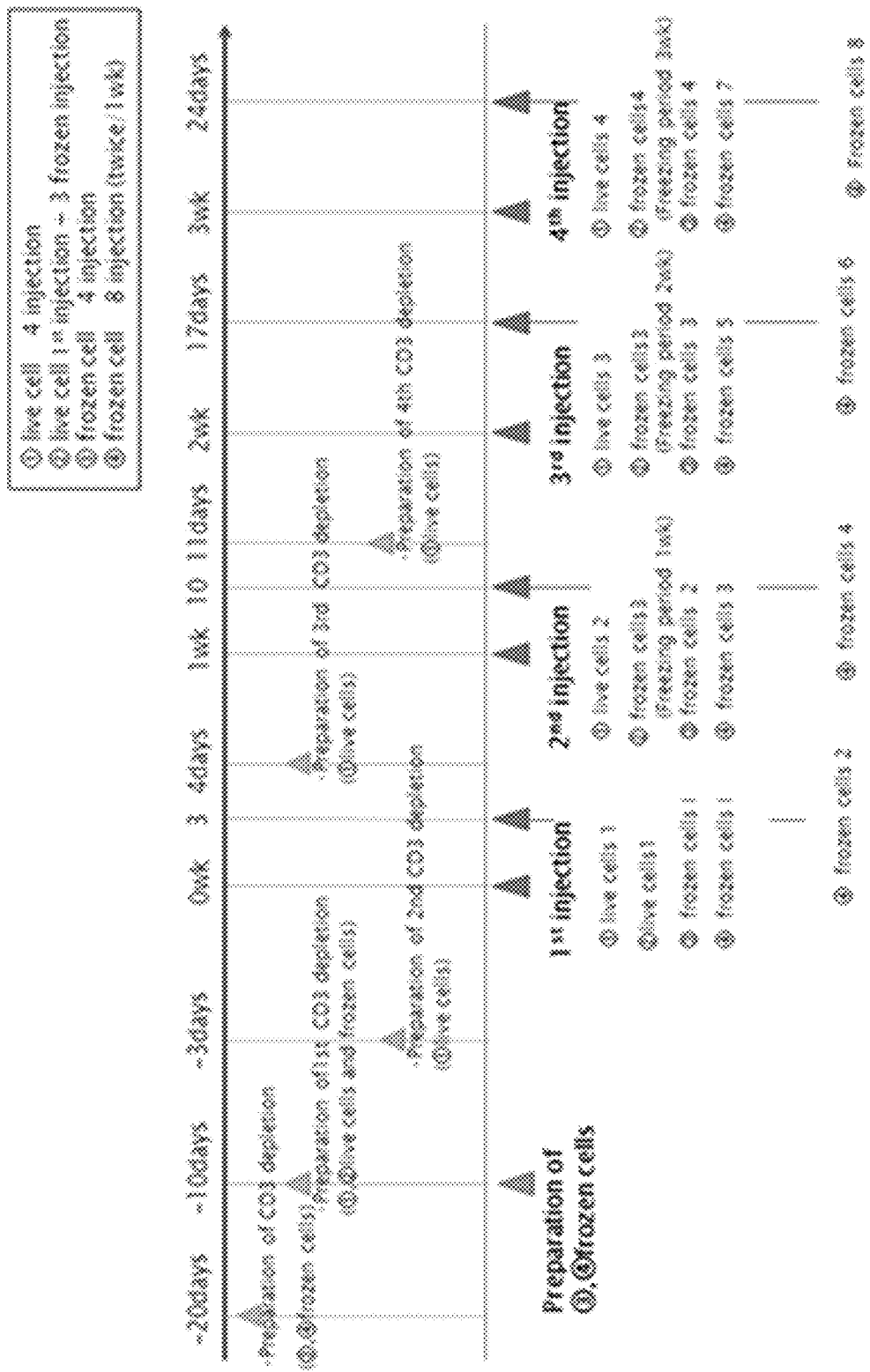

FIG. 6a shows an administration schedule prepared to examine the anticancer effect of NK cells according to freezing or not of NK cells.

Figure 6B:
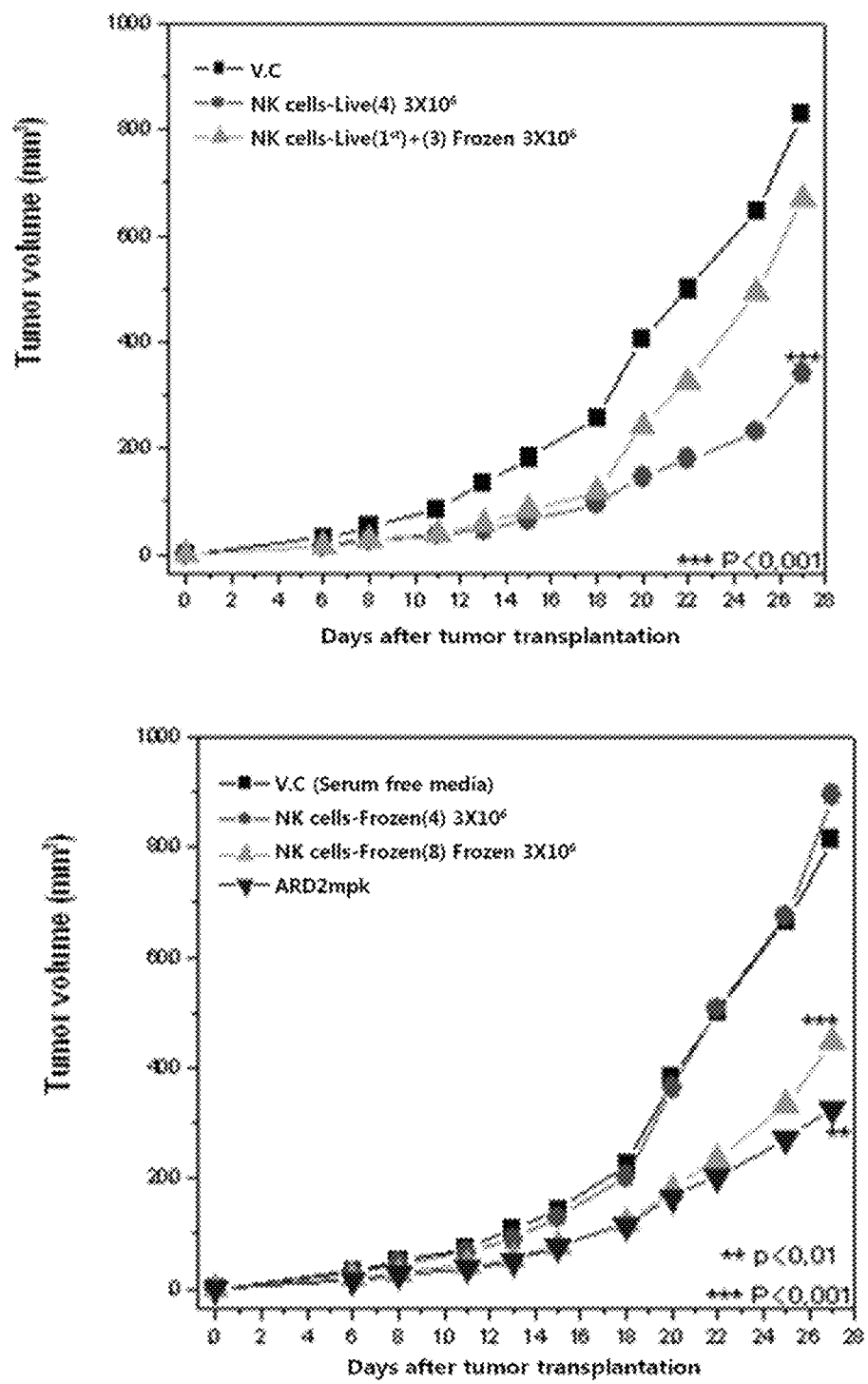

FIG. 6b shows the tumor volume inhibitory effect of NK cells against colorectal cancer according to freezing or not of NK cells.

V.C: vehicle control group;
NK Cell-Live (4): group administered four times with fresh NK cells;
NK Cell-Live (1)+(3) frozen: group administered once with fresh NK cells and three times with thawed cryopreserved NK cells;
V.C (serum-free medium): serum-free medium group;

NK cell-frozen (4): group administered four times with thawed cryopreserved NK cells;

NK cell-frozen (8): group administered eight times with thawed cryopreserved NK cells; and ADR: adriamycin-treated group.

Figure 6C:
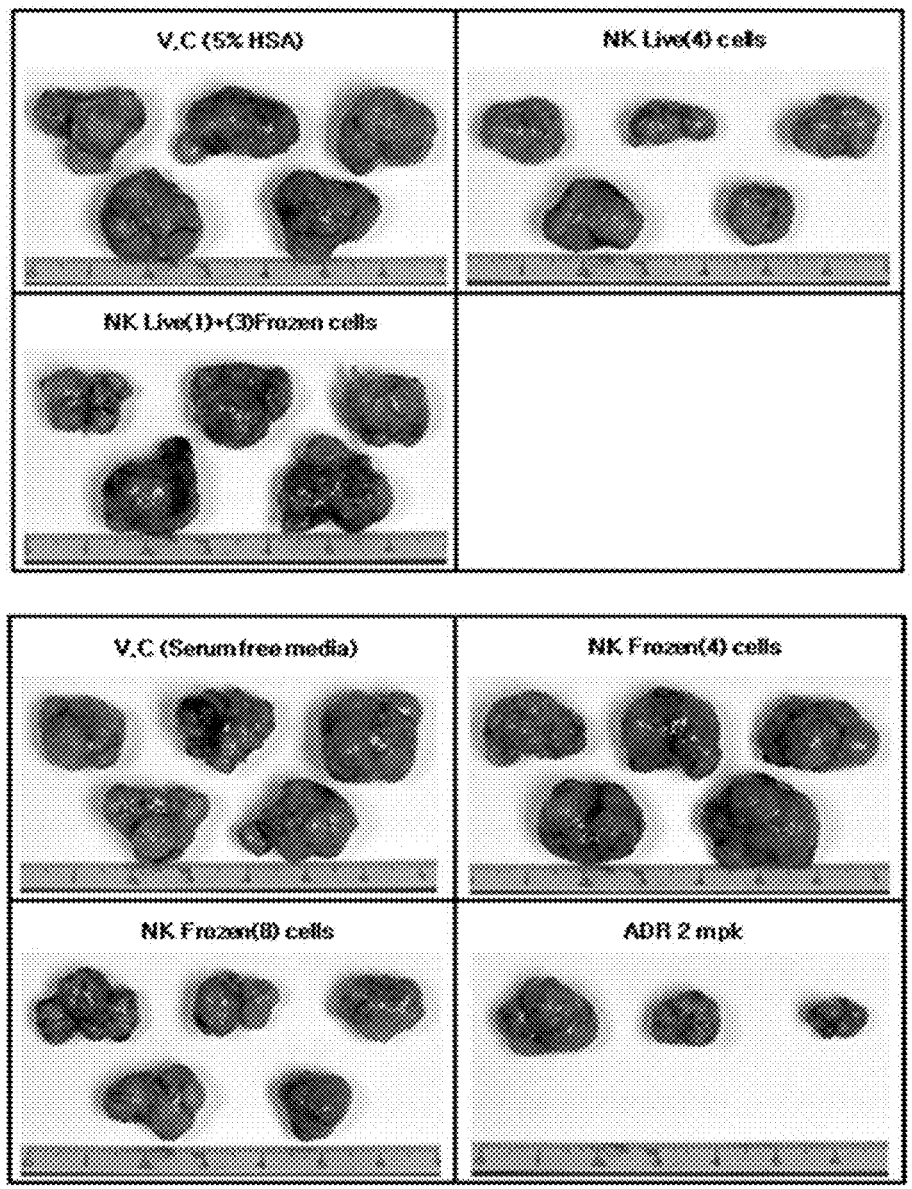

FIG. 6c shows the tumor weight-reducing effect of NK cells against colorectal cancer according to freezing or not of NK cells.

V.C: vehicle control group;

NK Cell-Live (4): group administered four times with fresh NK cells;

NK Cell-Live (1)+(3) frozen: group administered once with fresh NK cells and three times with thawed cryopreserved NK cells;

V.C (serum-free medium): serum-free medium group;

NK cell-frozen (4): group administered four times with thawed cryopreserved NK cells;

NK cell-frozen (8): group administered eight times with thawed cryopreserved NK cells; and ADR 2 mpk: adriamycin-treated group.

Figure 7A:
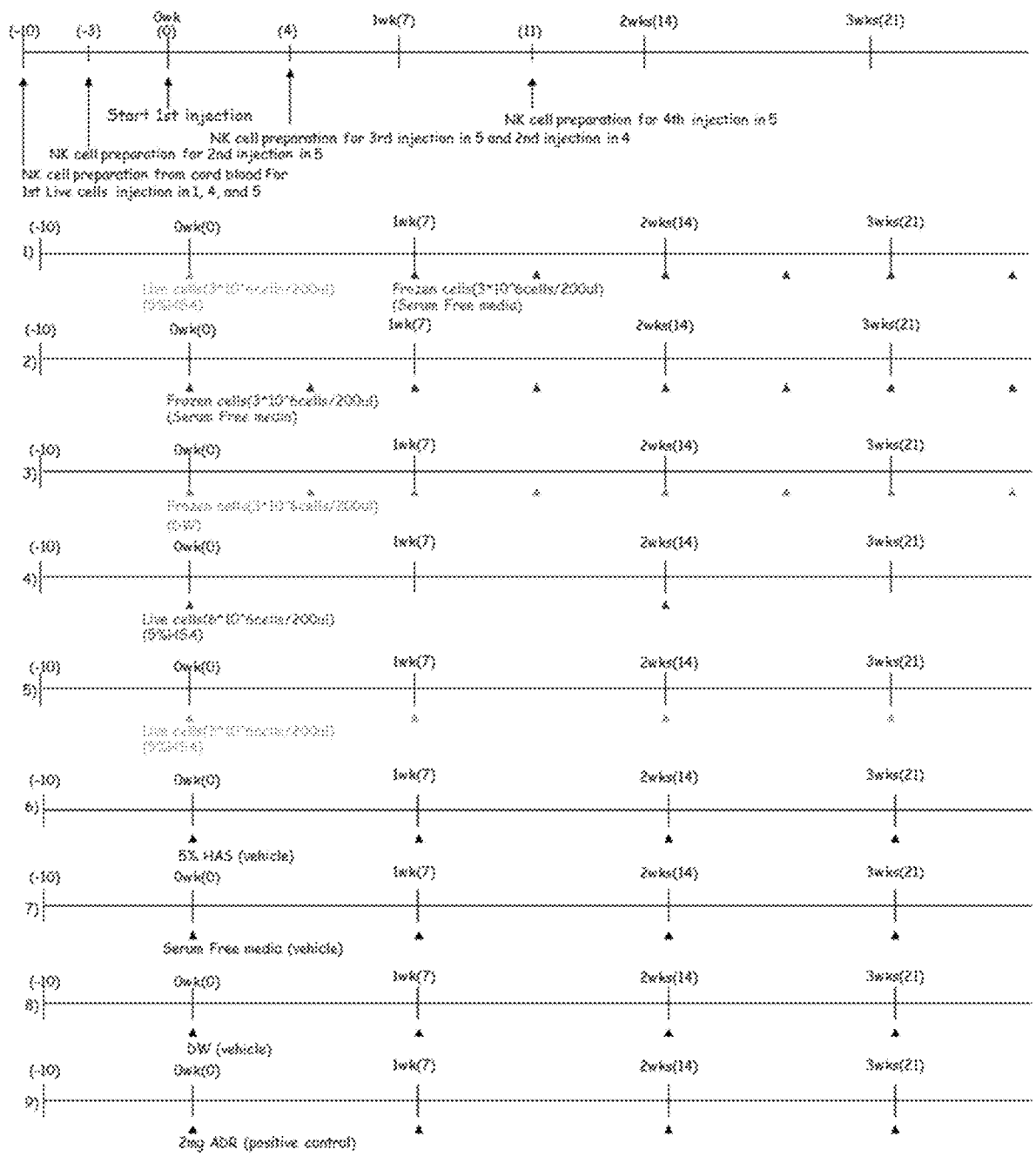

FIG. 7a shows administration schedules prepared to examine the anticancer effects of NK cells according to freezing or not of NK cells, the number of the NK cells and the number of administrations of the NK cells.

Figure 7B:
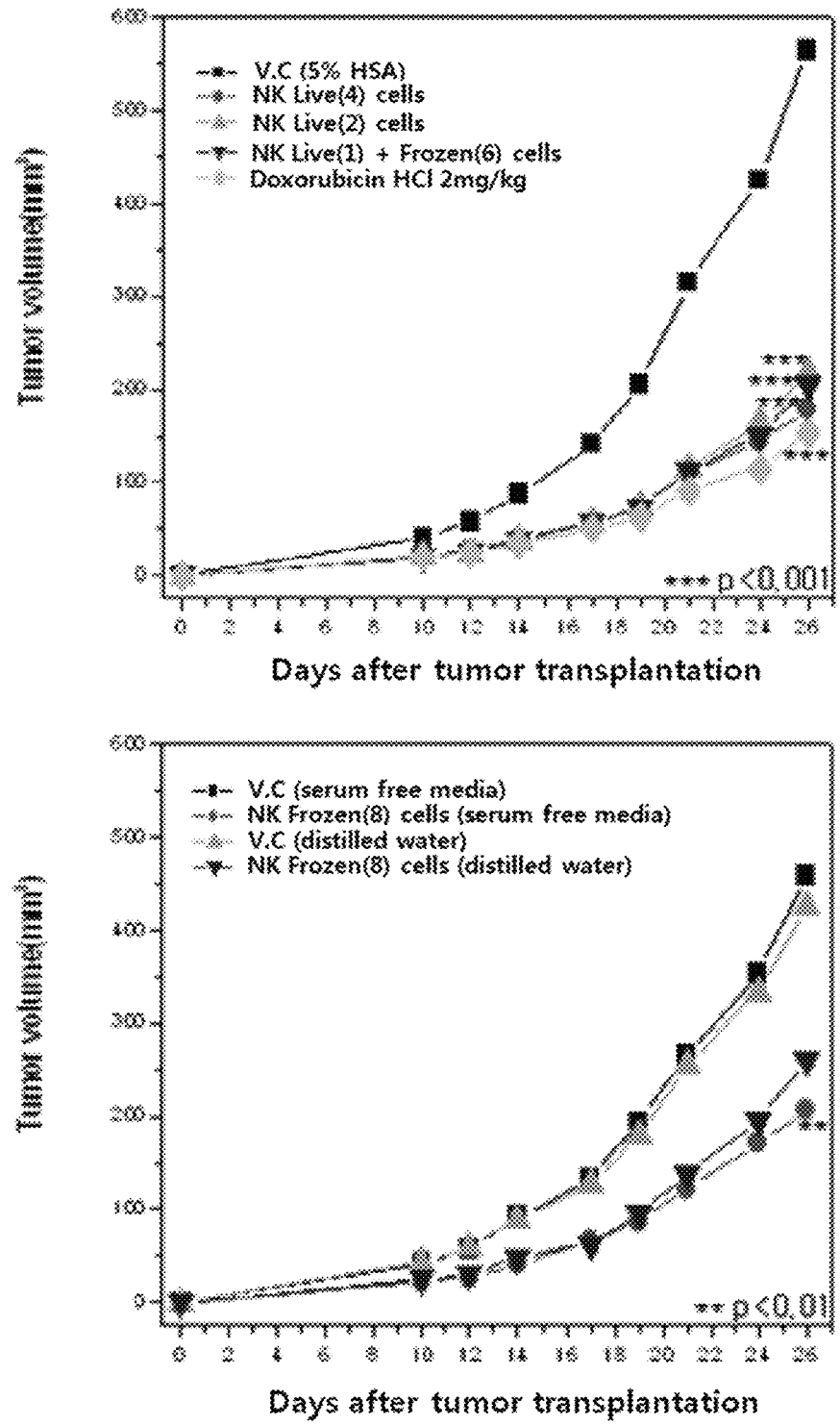

FIG. 7b shows the tumor volume effects of NK cells against colorectal cancer according to freezing or not of NK cells, the number of the NK cells and the number of administrations of the NK cells.

V.C (5% HSA): vehicle control group;

NK fresh (4) cells: group administered four times with fresh NK cells for 4 weeks;

NK fresh (2) cells: group administered twice with fresh NK cells for 4 weeks;

NK fresh (1)+(6) frozen cells: group administered once with fresh NK cells and then administered six times with thawed cryopreserved cells;

Doxorubicin HCL;

V.C (serum-free medium): serum-free control group;

NK frozen (8) cells (serum-free medium): group administered eight times with thawed cryopreserved NK cells in serum-free medium;

V.C (distilled water): sterile distilled water control group;

NK frozen (8) cells (distilled water): group administered eight times with thawed cryopreserved NK cells in sterile distilled water.

Figure 7C:
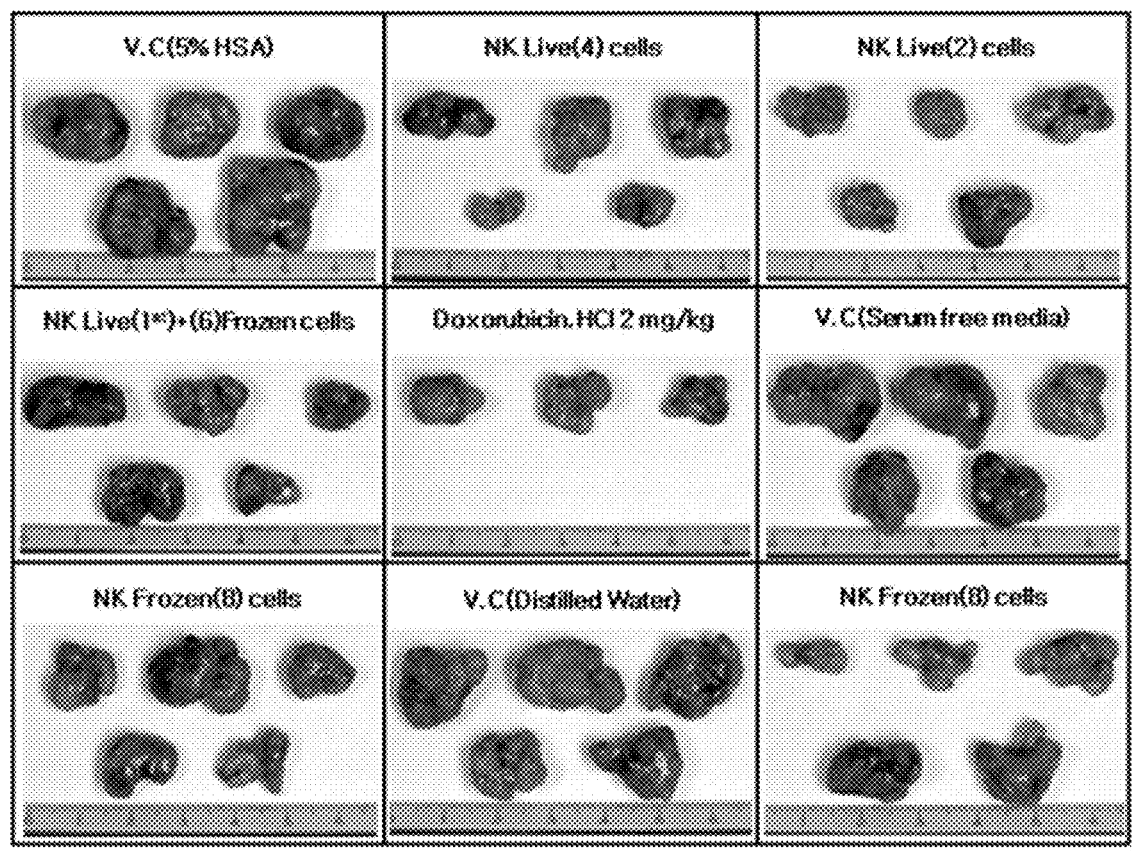

FIG. 7c shows the tumor weight-reducing effects of NK cells against colorectal cancer according to freezing or not of NK cells, the number of the NK cells and the number of administrations of the NK cells.

V.C (5% HSA): vehicle control group;

NK fresh (4) cells: group administered four times with fresh NK cells for 4 weeks;

NK fresh (2) cells: group administered twice with fresh NK cells for 4 weeks;

NK fresh (1)+(6) frozen cells: group administered once with fresh NK cells and then administered six times with thawed cryopreserved cells;

Doxorubicin HCL;

V.C (serum-free medium): serum-free control group;

NK frozen (8) cells (serum-free medium): group administered eight times with thawed cryopreserved NK cells in serum-free medium;

V.C (distilled water): sterile distilled water control group;

NK frozen (8) cells (distilled water): group administered eight times with thawed cryopreserved NK cells in sterile distilled water.

Figure 8A:
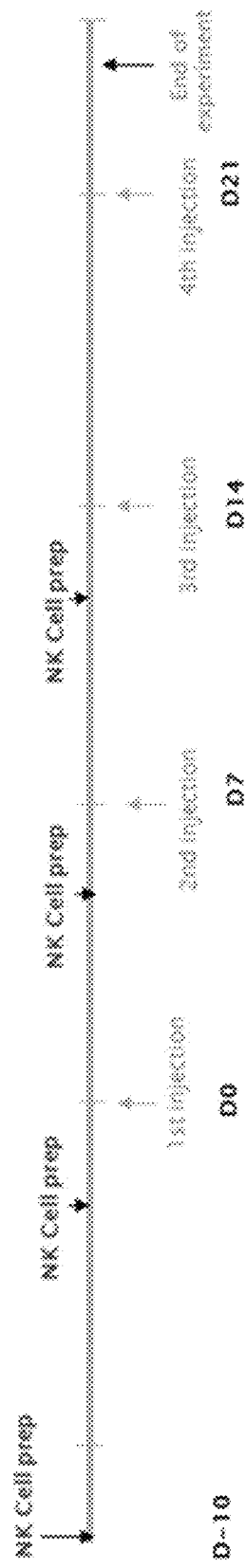

FIG. 8a shows an administration schedule prepared to examine the anticancer effect of NK cells against lung cancer according to the number of NK cells.

Figure 8B:
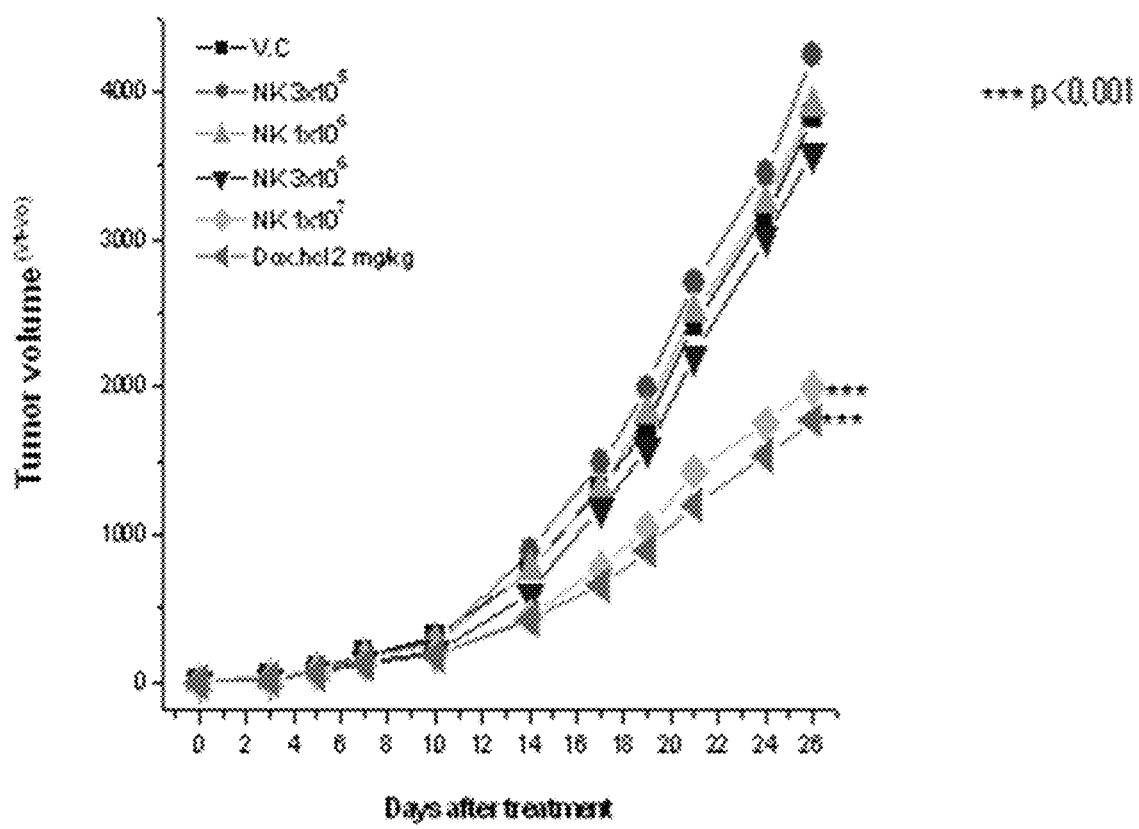

FIG. 8b shows the tumor volume inhibitory effect of NK cells against lung cancer according to the number of NK cells.

V.C: vehicle control group; and

Dox.hcl: Doxorubicin HCL.

Figure 8C:
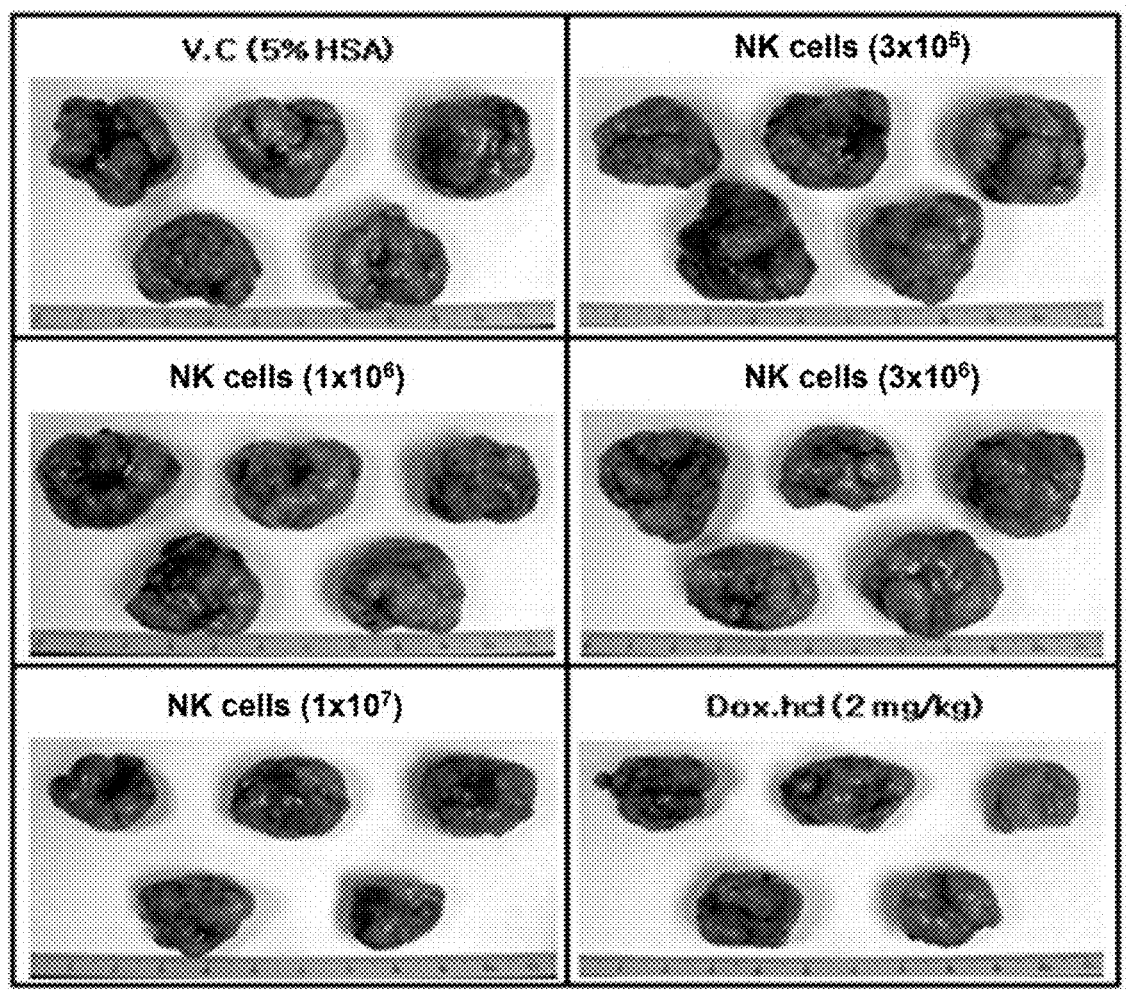

FIG. 8c shows the tumor weight-reducing effect of NK cells against lung cancer according to the number of NK cells.

V.C: vehicle control group; and

Dox.hcl: Doxorubicin HCL.

Figure 8D:
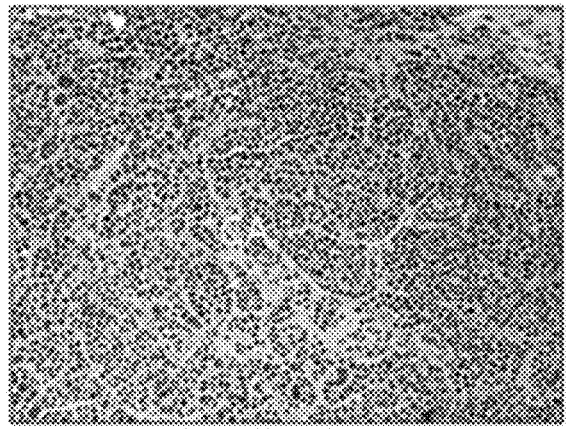
Figure 8D:
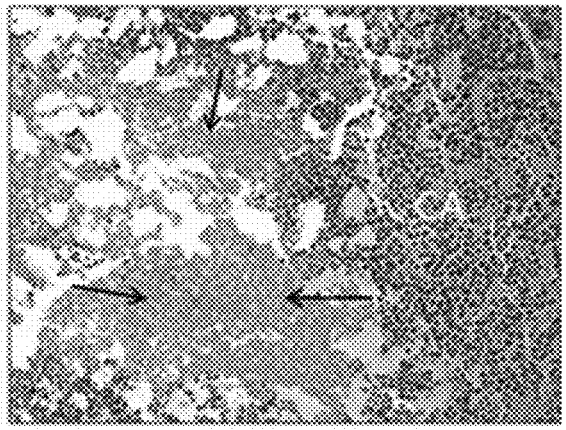
Figure 8D:
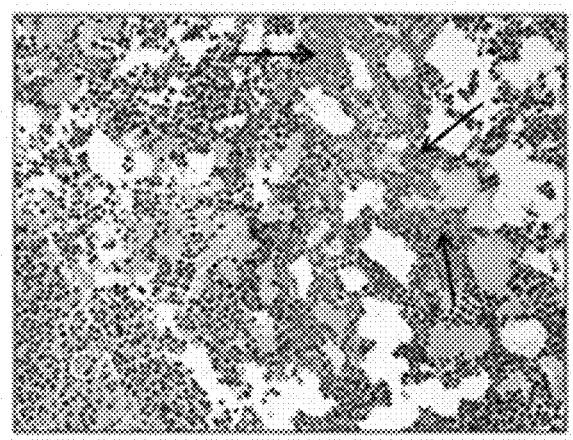
Figure 8D:
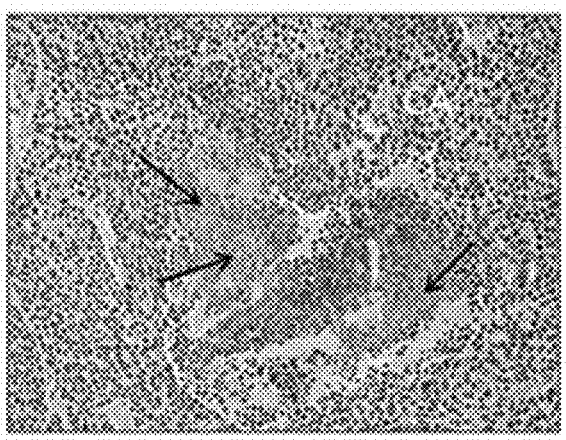

FIG. 8d shows the results of H-E staining performed to confirm that NK cells infiltrate into tumor tissue.

V.O: serum-free control group;

arrow: dead cancer cells; and

CA: cancer cells.

Figure 8E:
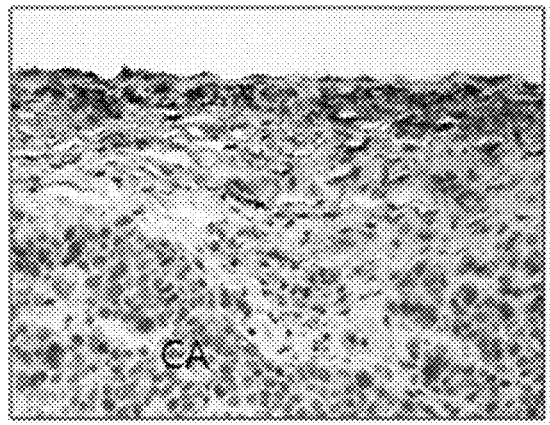
Figure 8E:
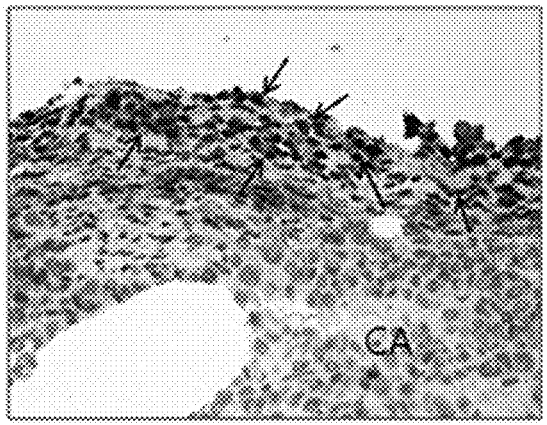
Figure 8E:
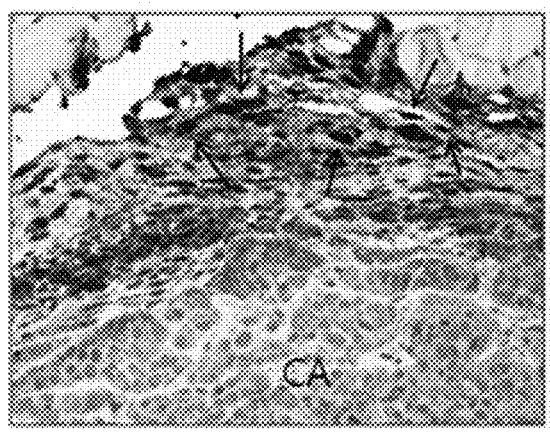
Figure 8E:
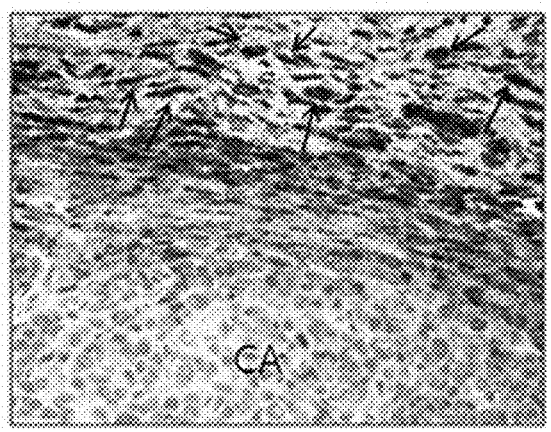

FIG. 8e shows the results of CD56 analysis performed to confirm that NK cells infiltrate into tumor tissue.

V.O: serum-free medium control group, arrow: CD56-positive cells, and

CA: cancer cells.

Figure 9A:
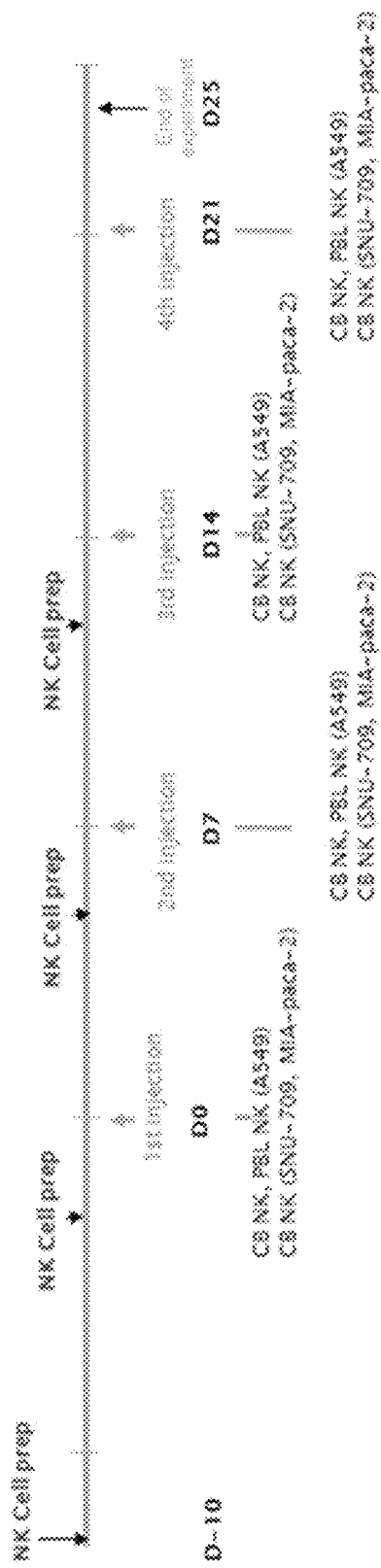

FIG. 9a shows an administration schedule prepared to examine the anticancer effects of NK cells against lung cancer, liver cancer and pancreatic cancer.

CB NK cells: umbilical cord blood-derived NK cells; and

PBL NK cells: peripheral cell-derived NK cells.

Figure 9B:
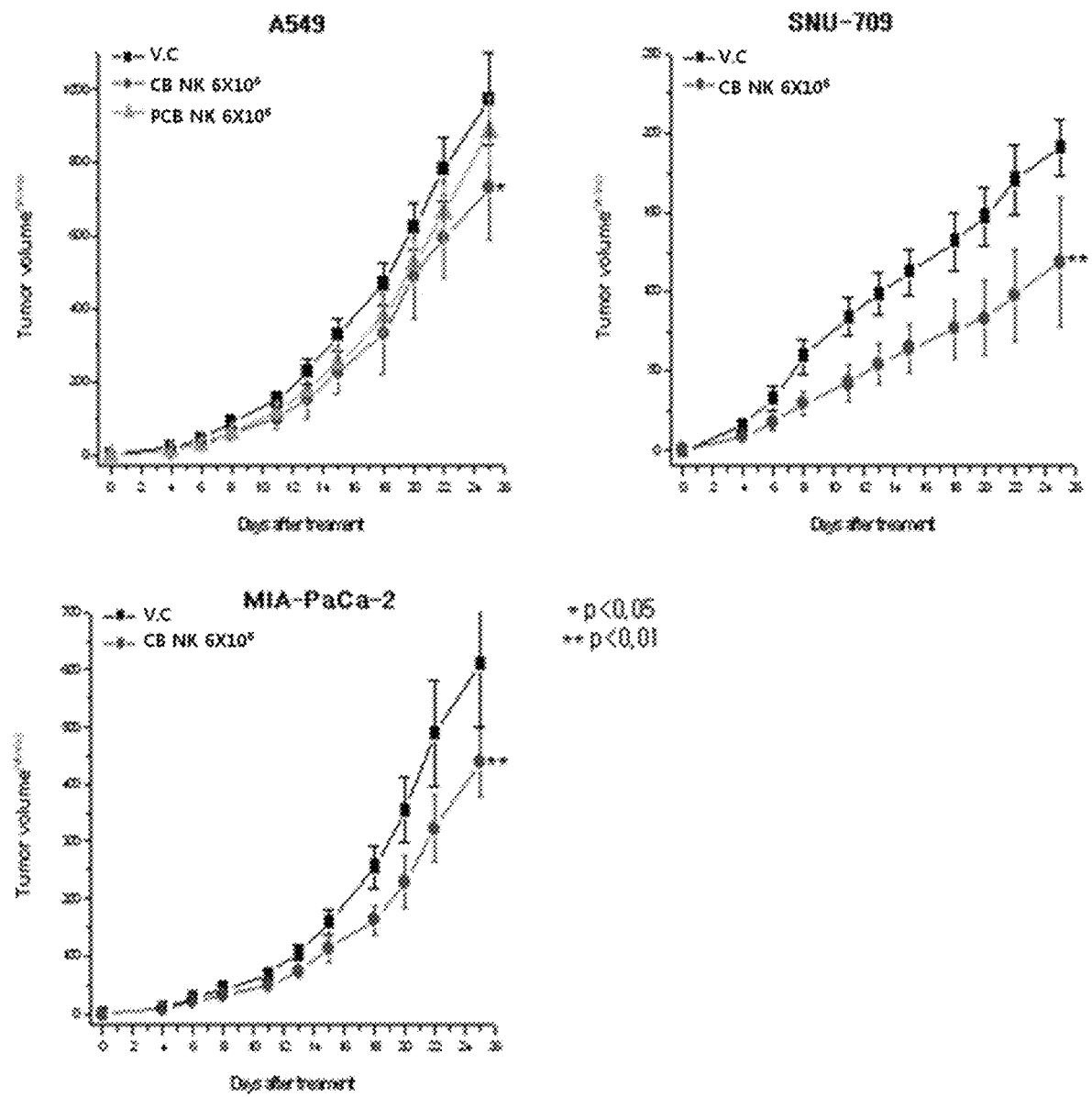

FIG. 9b shows the tumor volume inhibitory effects of NK cells against lung cancer (A549), liver cancer (SNU-709) and pancreatic cancer (MIA-PaCa-2).

V.C: vehicle control group,

CB NK cells: umbilical cord blood-derived NK cells; and

PBL NK cells: peripheral cell-derived NK cells.

Figure 9C:
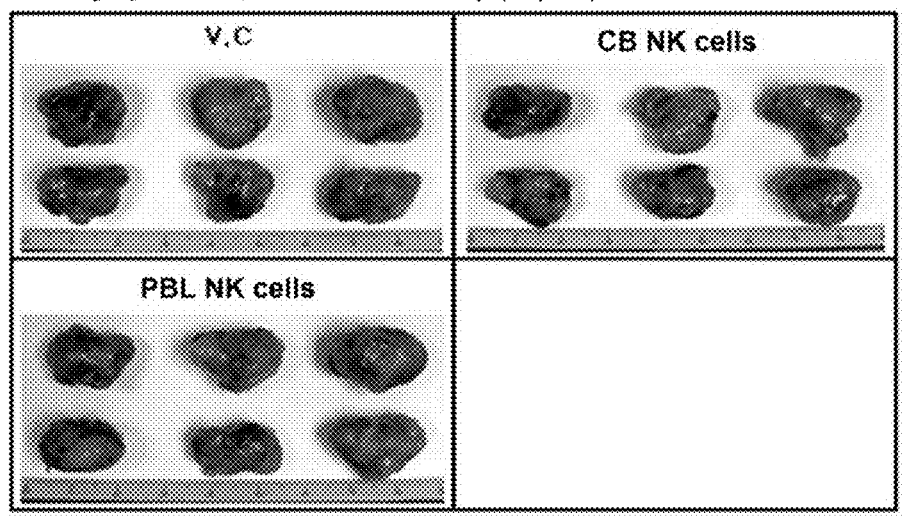
Figure 9C:
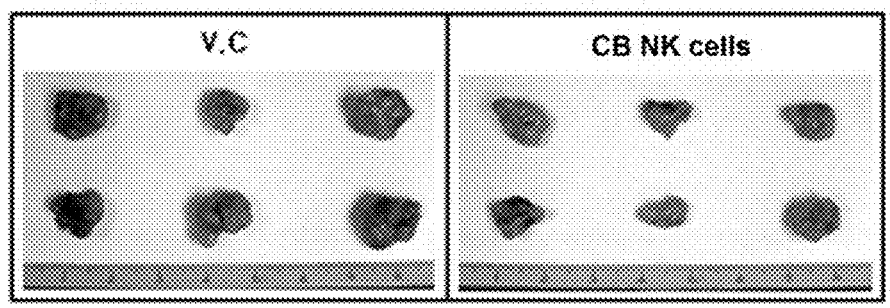
Figure 9C:
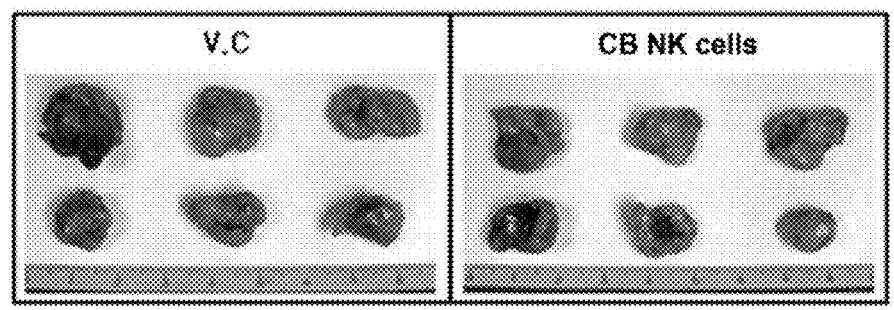

FIG. 9c shows the tumor weight-reducing effects of NK cells against lung cancer (A549), liver cancer (SNU-709) and pancreatic cancer (MIA-PaCa-2).

V.C: vehicle control group,

CB NK cells: umbilical cord blood-derived NK cells; and

PBL NK cells: peripheral cell-derived NK cells.

Figure 10:
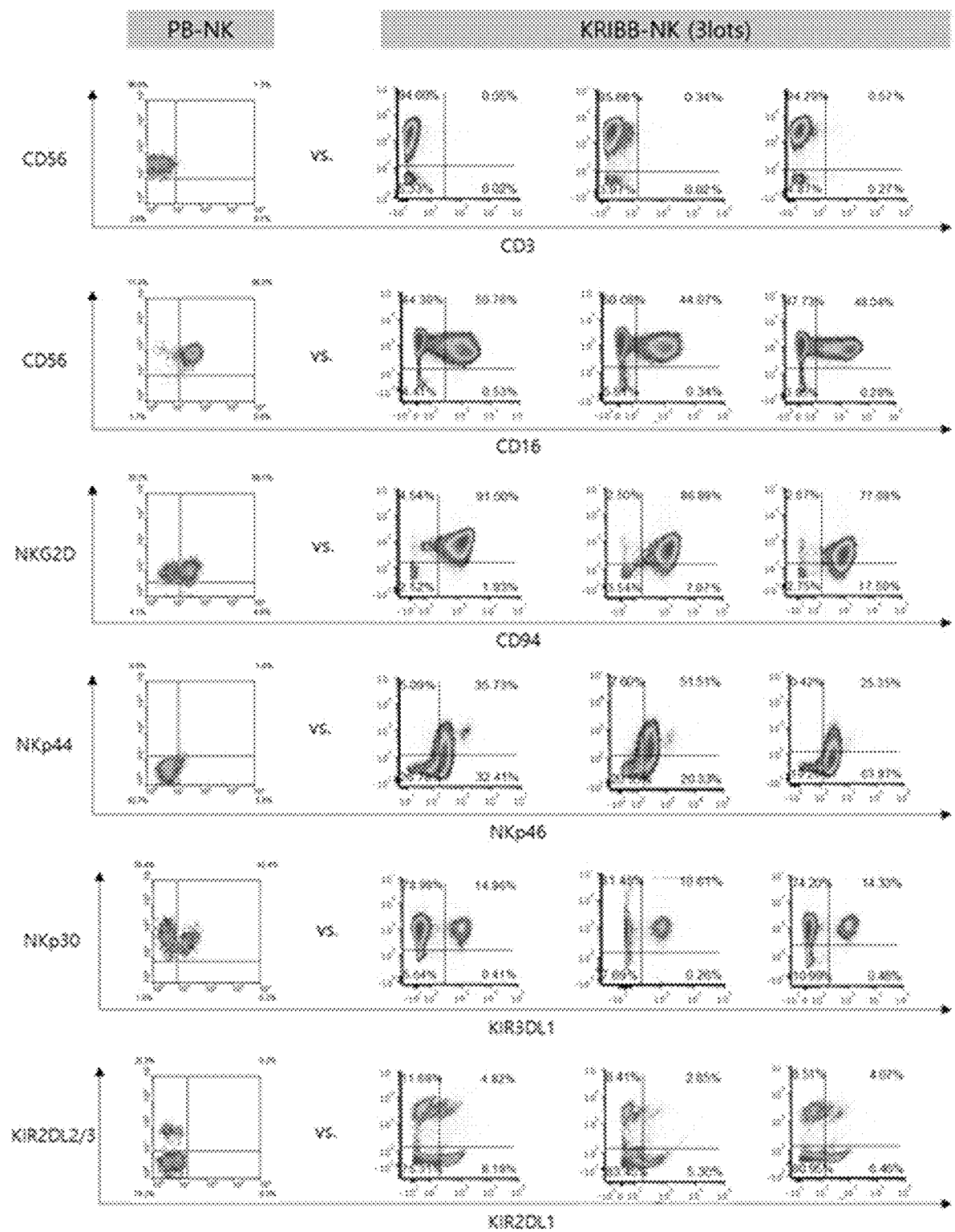

FIG. 10 shows the results of FACS analysis of NK cells (KRIBB-NK) according to the present disclosure and general peripheral blood-derived NK cells (PB-NK).

Figure 11:
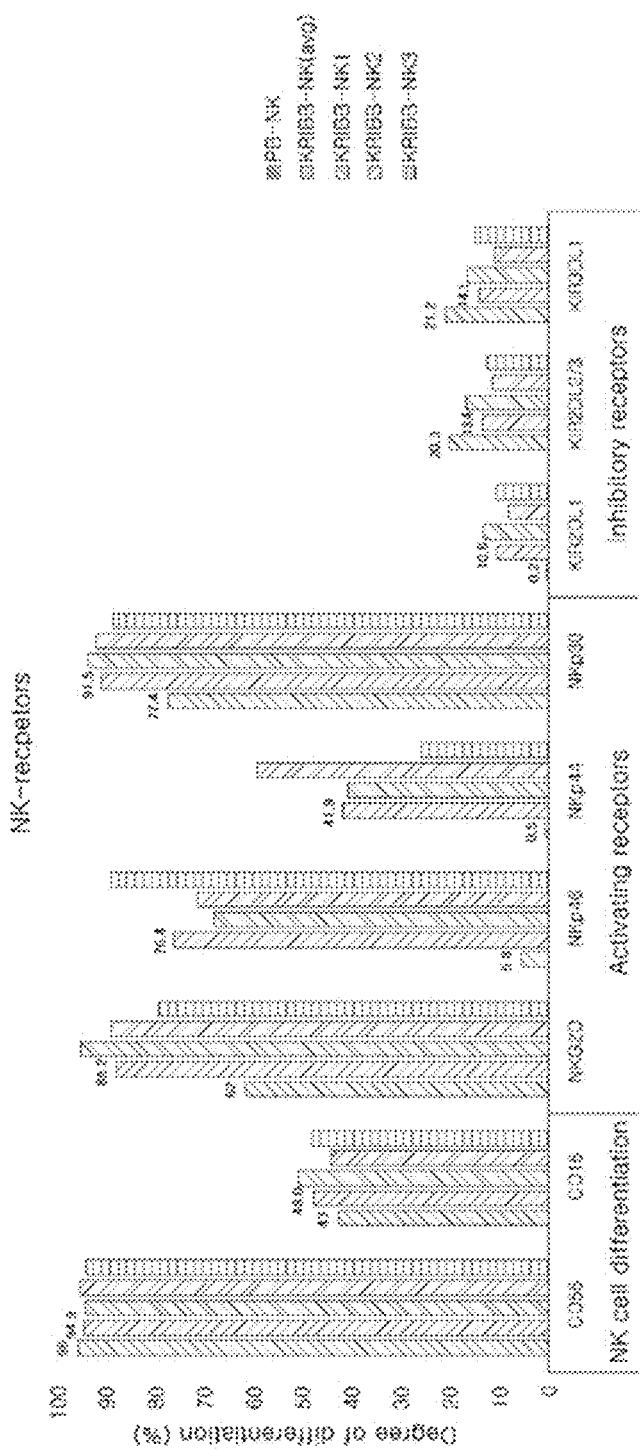

FIG. 11 shows comparison of the numerical results of FACS analysis of NK cells (KRIBB-NK) according to the present disclosure and general peripheral blood-derived NK cells (PB-NK).

Figure 12:
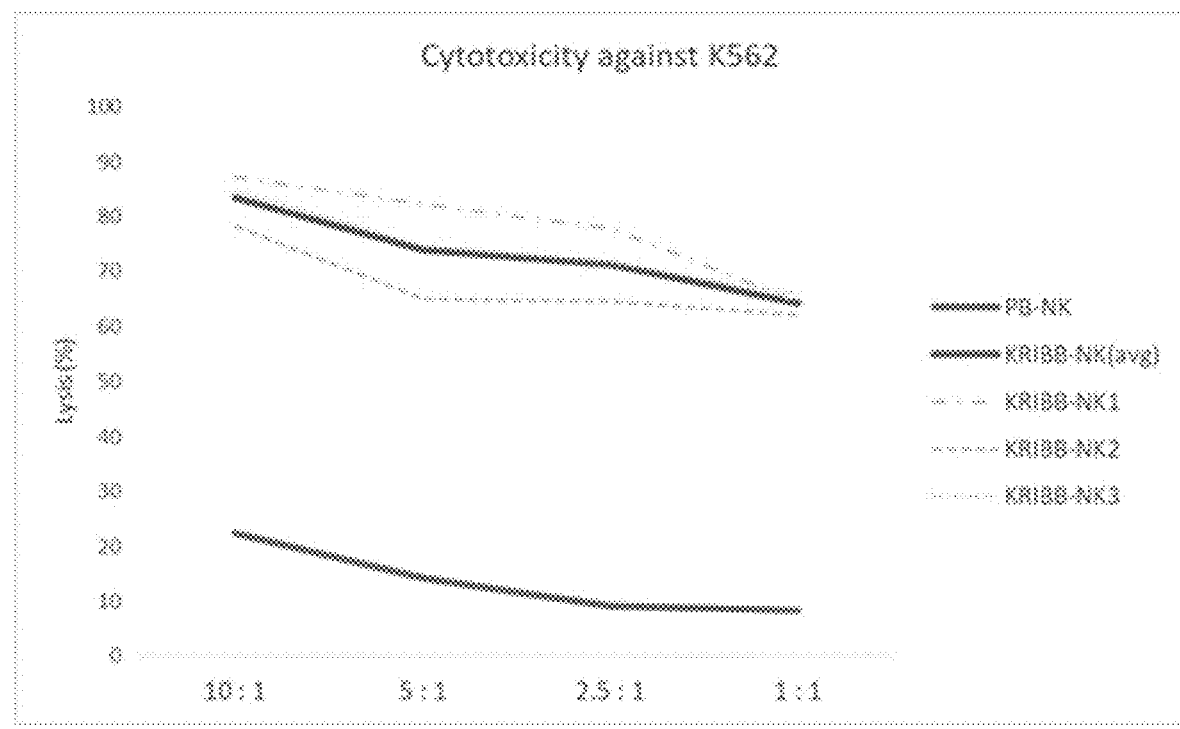

FIG. 12 shows the results of comparing the killing abilities of K562 cells by NK cells (KRIBB-NK) according to the present disclosure and general peripheral blood-derived NK cells (PB-NK).

Figure 13:
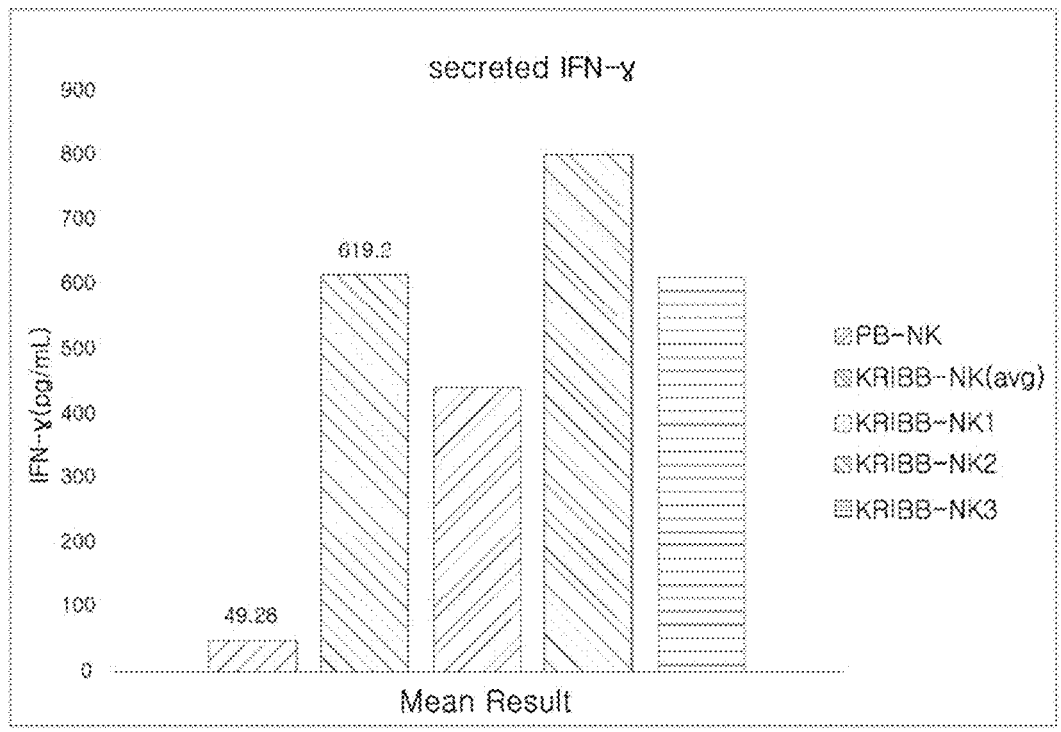
Figure 13:
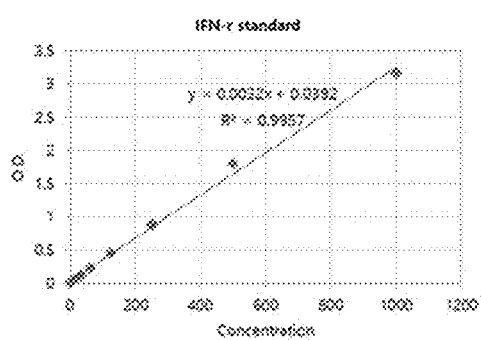

FIG. 13 shows the results of comparing the expressions of IFN-γ in NK cells (KRIBB-NK) according to the present disclosure and general peripheral blood-derived NK cells (PB-NK).

DETAILED DESCRIPTION OF THE INVENTION

Best Mode

Hereinafter, the present invention describes in detail with reference to examples and experimental examples.

Example 1: Production of NK Cells

Umbilical cord blood and peripheral blood, provided for research purposes from the Department of Obstetrics and Gynecology, Konyang University Hospital (Korea) and the Department of Obstetrics and Gynecology, Chungnam National University Hospital (Korea) (approved by the IRB of each hospital), were diluted at 2:1 with RPMI 1640 to prepare a blood dilution. The prepared blood dilution was placed carefully in the upper layer of Ficoll-Paque, and then centrifuged at 2,000 rpm for 30 minutes to obtain a mononuclear cell layer (MNC layer). Cells were carefully collected from the mononuclear cell layer, and erythrocytes were removed from the collected cells to obtain monocytes. CD3 microbeads (Miltenyi Biotech) were added to the obtained monocytes to label with CD3, and then CD3-positive cells were removed by using CS column and Vario MACS to obtain CD3-negative cells. Specifically, the CD3 microbeads (Miltenyi Biotech) recognized CD3 ε chains and capture CD3-positive cells from the monocytes so as to be magnetized. Then, among the monocytes, CD3-positive cells to which the microbeads were attached were passed through a MACS column reacting with a magnet, and thus CD3-positive cells remained in the column, and only CD3-negative cells were separated from the column.

Blood was diluted with saline and treated with a suitable amount of ROSETTESEP™ capable of cross-linking to CD3-positive cells, depending on the counted number of cells, after which the blood was agitated at room temperature for 20 minutes. After agitation, the blood was diluted 2-fold and placed onto Ficoll-Paque solution in such a manner that layers would not be mixed, after which the resulting solution was centrifuged at 2,000 rpm at room temperature for 20-30 minutes. After removal of the supernatant, the separated monocyte layer was collected and washed to obtain CD3-negative cells. The ROSETTESEP™ component is a tetrameric complex comprising mouse- and rat-derived monoclonal antibodies, glycoporin A antibody, and P9 antibody or P9 F(ab') antibody serving as a support. In the process of isolating the CD3-negative cells, the tetrameric complex of ROSETTESEP™ added to the blood crosslinks to CD3-positive cells in the blood to form immunorosettes, and the immunorosettes having a density higher than that of Ficoll is located below Ficoll by Ficoll-based density gradient centrifugation, and CD3-negative cells that did not bind to the tetrameric complex are located above Ficoll and isolated.

The isolated CD3-negative cells were seeded into a T75 flask at a concentration of $1 \times 10^6$ cells/ml, and cultured with IL-15 and IL-21 in alpha-MEM complete medium under the conditions of 37° C. and 5% $CO_2$ for 10-21 days. During culture, the concentration of the cells did not exceed $2 \times 10^6$ cells/ml, and was adjusted to a concentration of $1 \times 10^6$ cells/ml by use of a medium having the same conditions as those of the original medium. On 4, 8, 14, 18 and 21 days, the cell number was counted, and on 4, 8, 14 and 21, the cells were stained with CD3 and CD56 antibodies, and the proportion of $CD3^-CD56^+$ NK cells was analyzed by FACS according to a known method.

Figure 1:
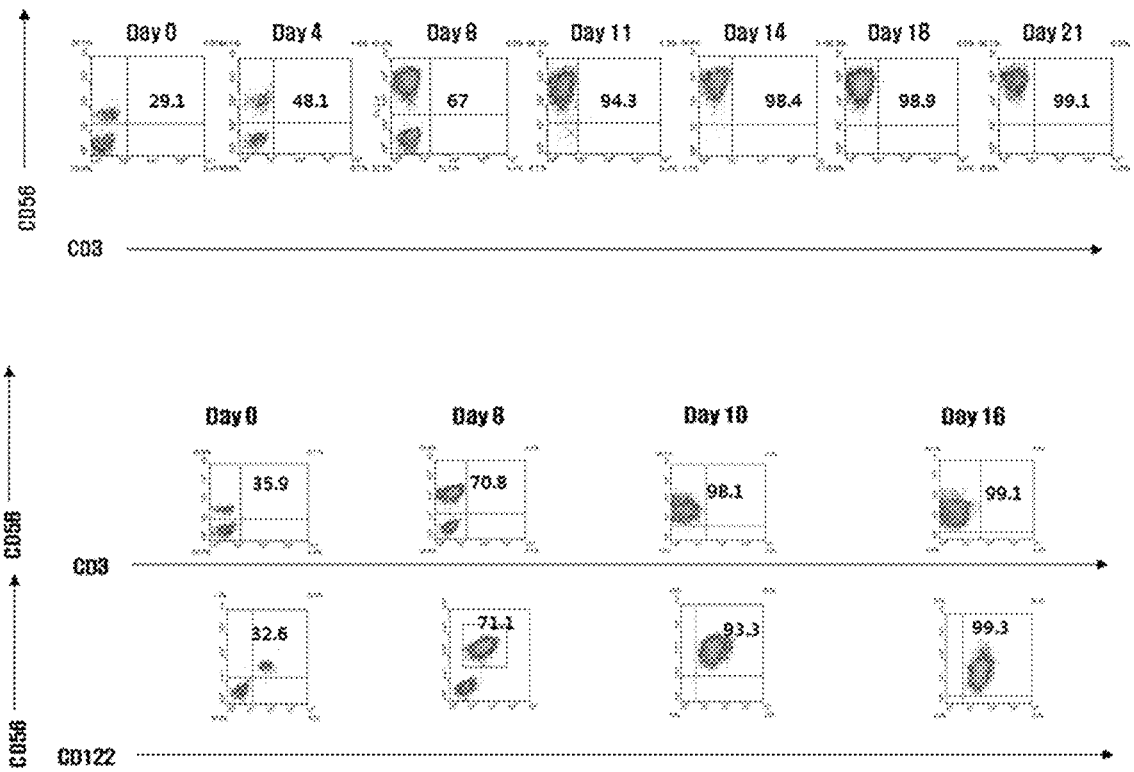
FIG. 1 shows FACS results indicating that differentiation of NK cells from CD3-negative cells isolated either from umbilical cord blood (the top of FIG. 1) or from peripheral blood (the bottom of FIG. 1) was induced after 11-21 days of culture.

As a result, as shown in FIG. 1, differentiation of NK cells from the CD3-negative cells isolated from umbilical cord blood (the top of FIG. 1) and peripheral blood (the bottom of FIG. 1) was induced after 11-21 days of culture.

Example 2: Production of Cryopreserved NK Cells 2-1: Production of Cryopreserved NK Cells from Differentiated NK Cells The NK cells (after 10 days of culture) produced by the method of Example 1 was cryopreserved to produced cryopreserved NK cells. The frozen storage was performed using a cryopreservation medium (Cryostor) containing 10% DMSO (dimethyl sulfoxide) under serum-free, protein-free and animal component-free conditions, and the differentiated NK cells were frozen at a concentration of $2.25 \times 10^7$ cells/1.5 ml ($1.5 \times 10^7$ cells/ml). The freezing was performed using a cryopreservation box containing isopropyl alcohol, and the cells were cooled stepwise from −70° C. (deep freezer) and finally preserved at −200° C. (LN2).

The cryopreservation was performed for 1 month. Immediately before use, the cryopreserved cells were thawed rapidly at 37° C. by washing the cells with saline to remove the cryopreservation medium. The thawed cryopreserved NK cells were analyzed by FACS to determine the proportion of $CD3^-CD56^+$ NK cells, the proportion of NK receptors, the cell viability, and their cytotoxicity to CML (chronic myelogenous leukemia) cells, and the characteristics thereof were compared with fresh NK cells (fresh NK cells, not cryopreserved) of the same origin.

Figure 2A:
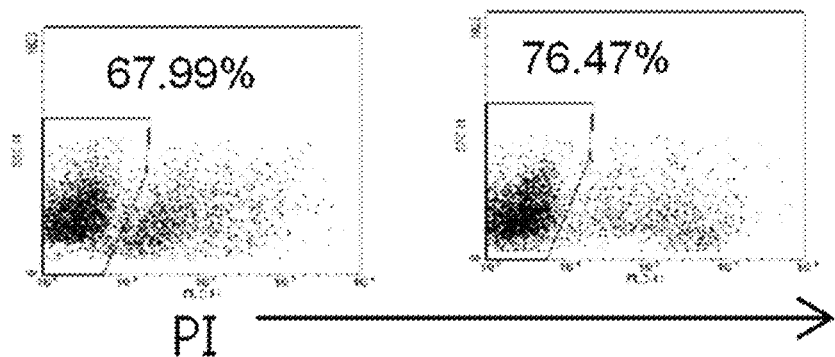
FIG. 2a shows the viability of thawed NK cells obtained by cryopreserving fresh NK cells on 10 days of culture and thawing the cryopreserved NK cells.
Figure 2B:
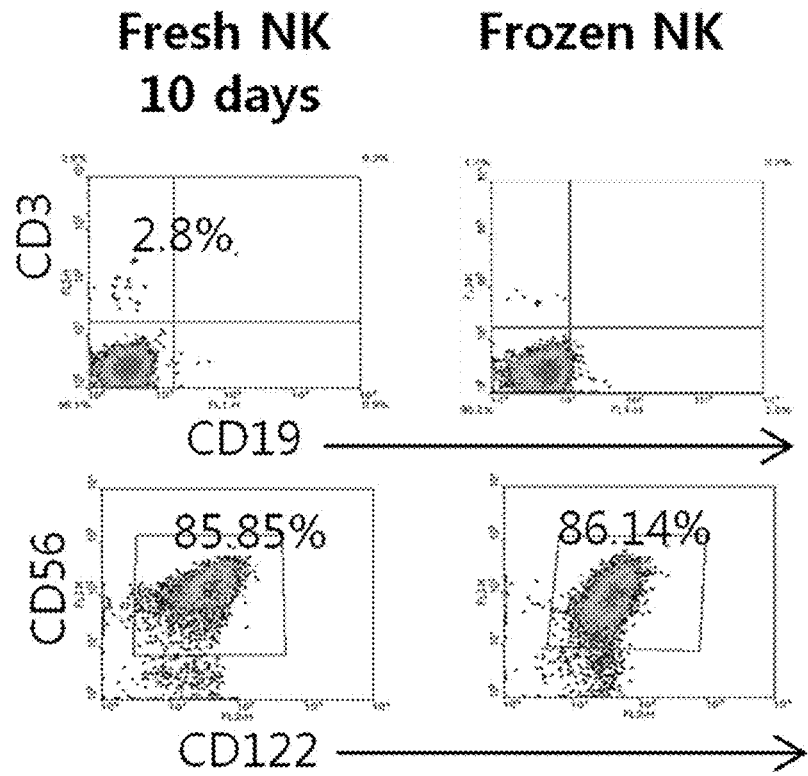
FIG. 2b shows the degree of differentiation.
Figure 2C:
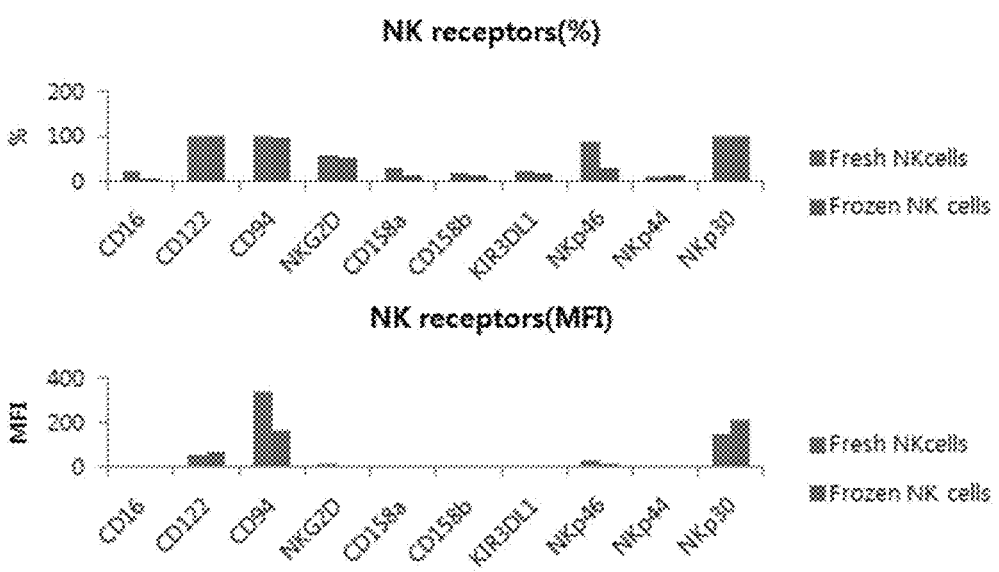
FIG. 2c shows NK cell receptors.

The results are shown in FIG. 2a (1. viability), FIG. 2b (2. degree of differentiation), FIG. 2c (3. receptors), FIG. 2d (4. cytotoxicity). As can be seen in FIGS. 2a to 2d, it was shown that the thawed cryopreserved NK cells had characteristics similar to those of fresh NK cells.

2-2: Production of NK Cells from Cryopreserved CD3-Negative Cells

According to the same method as described in Example 1, CD3-negative cells were obtained from umbilical cord blood, and the CD3-negative cells were cryopreserved using the same cryopreservation medium as described in Example 2-1. The concentration of the CD3-negative cells during cryopreservation was $2.25 \times 10^7$ cells/1.5 ml ($1.5 \times 10^7$ cells/ml), and the cryopreservation was performed for about 1 month.

To obtain differentiated NK cells from the cryopreserved CD3-negative cells, the frozen cells were thawed and cultured in the same manner as described in Example 1. On 0, 2, 4, 7, 9 and 12 days after thawing, the number and viability of the cells were measured, and on 0, 7 and 9 days after thawing, the proportion of CD3−CD56+NK cells was analyzed by FACS.

Figure 2G:
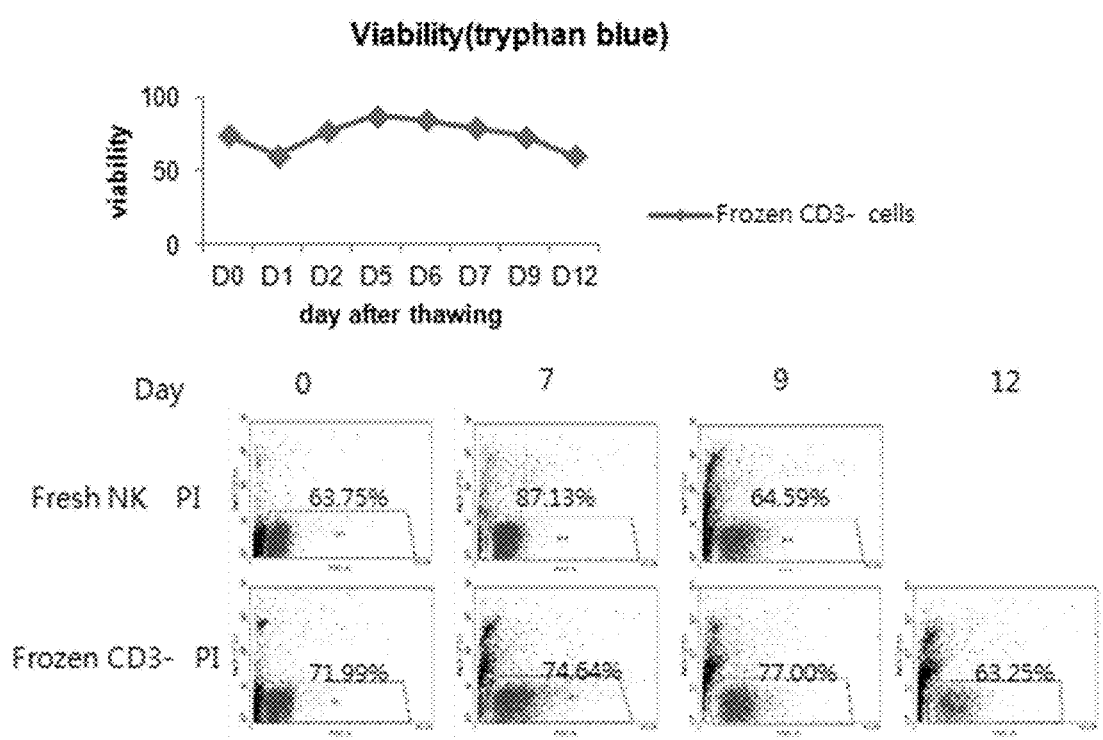
FIG. 2g shows cell viability.
Figure 2H:
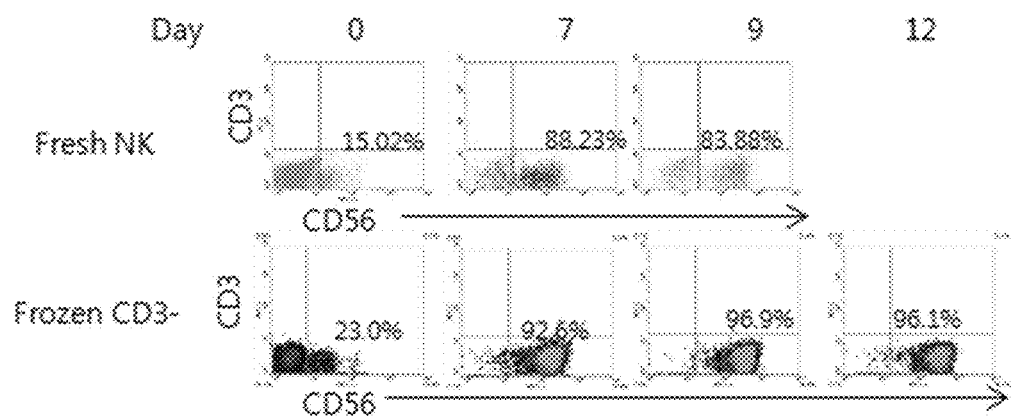
FIG. 2h shows the degree of differentiation and NK cell receptors.
Figure 2H:
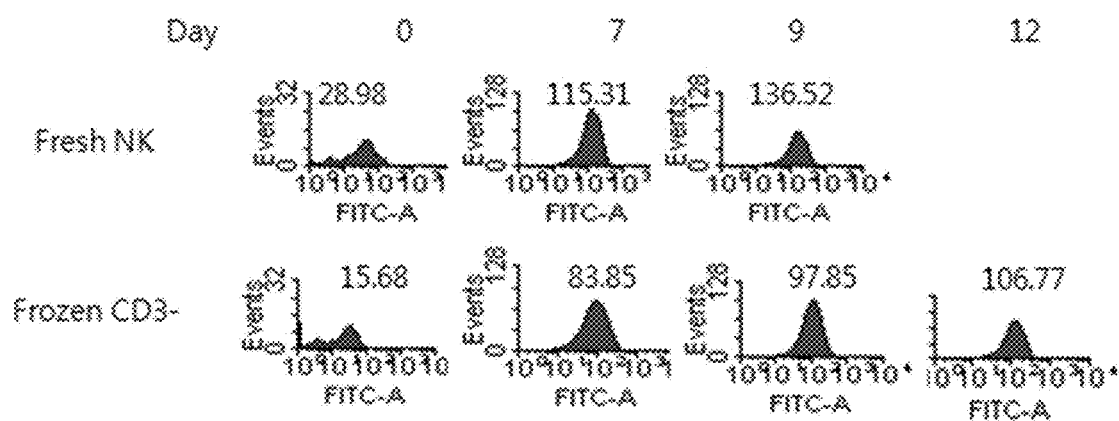

As a result, it was shown that the NK cells obtained from the cryopreserved CD3-negative cells showed characteristics similar to those of fresh NK cells with respect to all the recovery rate of cells recovered after thawing (FIG. 2e), the number of cells (FIG. 2f), the viability of cells (FIG. 2g) and the degree of differentiation (FIG. 2h).

Reference Example: Examination of In Vivo Distribution of NK Cells in Mice

In order to examine the tissue distribution of the fresh NK cells produced in Example 1, the following experiment was performed.

To examine the distribution of NK cells, the NK cells were labeled with DiR. Specifically, $1 \times 10^7$ cells were suspended in 10 ml of 1×PBS (phosphate buffered saline) containing 3.5 μg/ml of DiR (1,1'-dioctadecyl-3,3,3',3'-tetramethylindotricarbocyanine, Sigma, USA) dye and 0.5% ethanol, and were incubated at 37° C. for 1 hour. After incubation, the cells were washed twice with 1×PBS and stained with Trypan blue to examine the in vivo distribution of the NK cells.

In order to examine the tissue distribution of the DiR-labeled NK cells at varying time points, 5% HSA or DiR-labeled NK cells were injected intravenously into BALB/C female nude mice at cell concentrations of $1 \times 10^3$, $1 \times 10^4$, $5 \times 10^4$, $1 \times 10^5$, $5 \times 10^5$, $1 \times 10^6$ and $5 \times 10^6$ cells, and after a given amount of time, and the distribution of the NK cells in the mouse or the major organs (liver, spleen, heart and kidney) extracted from the mice by autopsy was examined using a live animal imaging system (PHOTONE IMAGER, Biospace) according to the manufacturer's protocol.

To measure the detection limit of the DiR-labeled NK cells at varying concentrations, the in vivo distribution of the DiR-labeled NK cells was examined 24 hours after injection of the cells. As a result, as shown in FIG. 3a, at cell concentrations equal to or lower than $5 \times 10^4$ cells, the distribution pattern of the DiR-labeled NK cells was not clear, and at cell concentrations equal to or higher than $1 \times 10^5$ cells, the image signal was strongly detected in the abdomen of the mice in a concentration-dependent manner (FIG. 3a). Furthermore, the major intra-abdominal organs (liver, spleen, kidney, heart and lung) were extracted and imaged, and as a result, it was shown that, at cell concentrations equal to or lower than $5 \times 10^4$ cells, a weak distribution of the NK cells was observed only in the lung, but at cell concentrations equal to higher than $1 \times 10^5$ cells, the image signal was strongly detected in the liver, the spleen and the lung in a concentration-dependent manner (FIG. 3b).

Next, in order to examine the distribution of the DiR-labeled NK cells in tissue, $1 \times 10^7$ cells were administered intravenously into the mice, and after 30 minutes and 2 hours, the distribution of the cells was measured. As a result, as shown in FIG. 3c, the distribution of the DiR-labeled NK cells in the abdomen was strongly detected from the start of the measurement, and image signals, which were 4-fold and 3.8-fold higher than the vehicle control group, were detected after 30 minutes and 2 hours, respectively. In addition, the liver, spleen, kidney, heart and lung, which are the major intra-abdominal organs, were extracted and imaged, and as a result, the distribution of the DiR-labeled NK cells in the liver, spleen and lung was strongly detected (FIG. 3c). Particularly, in the liver, image signals, which were about 9.5-fold and 5.1-fold higher than those in the vehicle control group, were detected at 30 minutes and 2 hours, respectively.

Next, the distribution was measured three times a week during a period ranging from one day after intravenous administration of the DiR-labeled NK cells to the day on which the DiR-labeled NK cells were not detected. As a result, as shown in FIG. 3d, up to 14 days after administration, the DiR-labeled NK cells were strongly detected, and after 14 days, the image signal started to be weakened, and on 42 days, the DiR-labeled NK cells were not detected in the measured image (FIG. 3d). The above results indicate that the NK cells of the present invention, after administered in vivo, survive in vivo for at least 30 days, and are abundantly distributed in lung, liver, spleen and the like.

Reference Example 1: Examination of the Anticancer Effect of Administration of Fresh NK Cells Against Colorectal Cancer 1-1: Examination of Tumor Volume Inhibition According to the Number of Administrations of NK Cells and the Use of NK Cells in Combination with IL-2

In order to examine the anticancer effect of the NK cells produced by the method of Example 1, mouse models xenografted with human colorectal cancer SW620 cells (Korea Research Institute of Bioscience and Biotechnology, Korea) were used.

Specifically, SW620 cells were suspended in PBS at a concentration of $2 \times 10^7$ cells/ml, and then injected subcutaneously into the axilla between the right shoulder and the chest wall in an amount of 0.3 ml per mouse. At 2 hours after injection of the cancer cells, the NK cells were injected into the mice at concentrations of $3 \times 10^5$, $1 \times 10^6$, $3 \times 10^6$ and $1 \times 10^7$ cells/mouse. In addition, IL-2 was diluted in PBS, and the mice were treated with the IL-2 dilution at an IL-2 concentration of 10,000 U/mouse. During the experimental period, 0.2 ml of the NK cells were injected into the tail vein of each mouse once a week, a total of four times (0, 7, 14 and 21 days). Then, to measure the change in the tumor volume, the sizes in the three directions of the tumor were measured using vernier calipers a total of 7 times during a period ranging from the day of start of drug administration to the day of autopsy, and then the tumor cell volume was measured using the following equation 1:

$$\text{Tumor cell volume} = (\text{length} + \text{width} + \text{height})/2 \qquad \text{Equation 1}$$

As a result, as shown in FIG. 4b, the groups injected with the NK cells at concentrations of $3 \times 10^5$, $1 \times 10^6$, $3 \times 10^6$ and $1 \times 10^7$ cells/mouse showed tumor growth inhibitions of 23.8%, 53.4% ($p<0.001$), 59.4% ($p<0.001$) and 76.8% ($p<0.001$), respectively, compared to that in the vehicle control group, and the positive control group administered with adriamycin showed a tumor growth inhibition of 58.3% ($p<0.001$). In addition, when the mice were treated with the NK cells in combination with IL-2, the groups injected with the NK cells at concentrations of $3 \times 10^5$, $1 \times 10^6$, $3 \times 10^6$ and $1 \times 10^7$ cells/mouse showed tumor growth inhibitions of 17.0%, 33.8% ($p<0.01$), 49.8% ($p<0.01$) and 73.5% ($p<0.001$), respectively (FIG. 4b).

1-2: Examination of Tumor Weight Decrease According to the Number of Administrations of NK Cells and the Use of NK Cells in Combination with IL-2

In order to examine the anticancer effects of the NK cells according to the number of administration of the NK cells and the use of the NK cells in combination with IL-2, the weights of tumors in drug-treated mice were measured.

According to the same method as described in Experimental Example 1-1, mice were treated with the NK cells alone or in combination with IL-2. On day 23, the mice were sacrificed using $CO_2$ gas, and tumors were separated from the sacrificed mice and weighed using a chemical balance. The tumors were photographed and fixed in liquid nitrogen. All the measurements were analyzed by t-TEST to determine the statistical significance between the vehicle control group and the administered groups.

As a result, as shown in FIG. 4c, the groups injected with the NK cells at concentrations of $3 \times 10^5$, $1 \times 10^6$, $3 \times 10^6$ and $1 \times 10^7$ cells/mice showed tumor weight decreases of 23.4%, 54.0%, 59.1% ($p<0.05$) and 78.8% ($p<0.01$), respectively, compared to the vehicle control group (FIG. 4c). In addition, when the mice were treated with the NK cells in combination with IL-2, the groups injected with the NK cells at concentrations of $3 \times 10^5$, $1 \times 10^6$, $3 \times 10^6$ and $1 \times 10^7$ cells/mice showed tumor weight decreases of 17.0%, 34.3%, 47.0% and 75.6% ($p<0.01$), respectively, and the positive control group administered with adriamycin showed a tumor weight decrease of 58.2% ($p<0.05$) (FIG. 4c).

1-3: Examination of Cytotoxicity According to the Number of NK Cells and the Use of NK Cells in Combination with IL-2

In order to examine the cytotoxicity of the NK cells to the mice of Experimental Example 1-1 according to administration of the NK cells alone or in combination with IL-2, the change in body weight and general symptoms of the mice were observed.

As a result, in the groups administered with the NK cells alone or in combination with IL-2, a normal increase in the body weight was observed without general symptoms during the experimental period, unlike the vehicle control group. However, the positive control group administered with adriamycin showed a statistically significant weight decrease of 21.8% (p<0.01).

In conclusion, the NK cells of the present invention, when administered alone or in combination with IL-2, did not show general symptoms and toxic symptoms such as weight loss. Regarding the anticancer effects, the group administered with the NK cells alone showed an excellent tumor growth inhibition of 70% or more, and the group administered with the NK cells in combination with IL-2 did not show increased effects compared to the group administered with the NK cells alone.

Reference Example 2: Examination of Anticancer Effects of NK Cells According to the Incubation, Preservation Conditions and Administration Schedules of NK Cells 2-1: Examination of Tumor Size Inhibition According to the Incubation, Preservation Conditions and Administration Schedules of NK Cells In order to examine the anticancer effects of the NK cells of the present invention according to the NK cell incubation method (comprising removing CD3-positive T cells by ROSETTESEP™ or not comprising the removal process), preservation conditions (fresh cells or cold-preserved cells) and administration schedules (once a week for 4 weeks, or twice a week for 2 weeks).

Specifically, NK cells were divided according to culture conditions into fresh NK, fresh NK (w/o ROSETTESEP™), 4° C. cold-preserved NK and 4° C. cold-preserved NK (w/o ROSETTESEP™), and the fresh NK cells were produced in the same manner as described in Example 1. The fresh NK (w/o ROSETTESEP™) cells were produced in the same manner as described in Example 1, except that the step of removing CD3-positive cells was omitted. The 4° C. cold-preserved NK cells were obtained by preserving fresh NK cells at 4° C. for 12 hours, and the 4° C. cold-preserved NK (w/o ROSETTESEP™) cells were obtained by producing NK cells without the step of removing CD3-positive cells, and preserving the produced cells at 4° C. for 12 hours. In order to administer the produced NK cells to mouse models, cancer cells were transplanted into mice in the same manner as described in Experimental Example 1-1, and when the average tumor volume reached about 50.0 mm$^3$, and the NK cells were administered to the mice at a concentration of $3 \times 10^6$ cells/mouse, and 0.2 ml of the NK cells were injected into the tail vein of each mouse. In the administration schedule, the NK cells were administered once a week for 4 weeks or administered twice a week for 2 weeks (FIG. 5a).

In order to examine the toxicity of the NK cells during the experimental period, the weight change and general symptoms of the mice were observed. As a result, in the groups administered with the NK cells once a week for 4 weeks [fresh NK, fresh NK (w/o ROSETTESEP™)] and twice a week for 2 weeks [fresh NK, fresh NK (w/o ROSETTESEP™), 4° C. cold-preserved NK, or 4° C. cold-preserved NK (w/o ROSETTESEP™)], a normal increase in the weight was observed without general symptoms during the experimental period, compared to the vehicle control group. However, in the positive control group administered with adriamycin, two dead animals and a statistically significant weight decrease of 31.5% (p<0.001) were observed.

In addition, in order to examine the anticancer effects of the NK cells according to the incubation, preservation conditions and administration schedules of the NK cells, the change in tumor volume was examined. As a result, as shown in FIG. 5b, the group, administered with fresh NK and fresh NK (w/o ROSETTESEP™) cells once a week for 4 weeks at a concentration of $3 \times 10^6$ cells/mouse, showed tumor growth inhibitions of 50.8% (p<0.001) and 32.7% (p<0.05), respectively, compared to the vehicle control group, and the groups, administered with fresh NK, fresh NK (w/o ROSETTESEP™ and 4° C. cold-preserved NK cells twice a week for 2 weeks, showed tumor growth inhibitions of 35.4%, 10.8% and 33.0%, respectively. The positive control group administered with adriamycin showed a tumor growth inhibition of 71.7% (p<0.01). However, the group administered with 4° C. cold-preserved NK (w/o ROSETTESEP™) cells showed no tumor growth inhibition. This suggests that, when the process of removing CD3-positive T cells is not performed, the proportion of NK cells is low, and thus the anticancer effect of the NK cells is reduced. Thus, it can be seen that the process of removing CD3-positive T cells is necessary to increase the anticancer effect of the NK cells.

2-2: Examination of Tumor Weight Decrease According to the Incubation, Preservation Condition and Administration Schedule of NK Cells In order to the anticancer effect of the NK cells of the present invention according to the incubation method, preservation condition and administration schedule of the NK cells, the decrease in tumor weight was examined.

Specifically, cancer cells were transplanted into mice in the same manner as described in Experimental Example 1-1, and NK cells were administered under the same conditions as described in Experimental Example 2-1. On 27 days after drug administration, the tumor was excised and weighed.

As a result, as shown in FIG. 5c, the groups, administered with fresh NK and fresh NK (w/o ROSETTESEP™) cells once a week for 4 weeks at a concentration of $3 \times 10^6$ cells/mouse, showed tumor weight decreases of 49.0% (p<0.001) and 33.1% (p<0.05), compared to the vehicle control group. Furthermore, the groups, administered with fresh NK, fresh NK (w/o ROSETTESEP™) and 4° C. cold-preserved NK cells twice a week for 2 weeks, showed tumor weight decreases of 30.3%, 7.2% and 29.0%, respectively, and the positive control group administered with adriamycin showed a tumor growth inhibition of 70.2% (p<0.05) (FIG. 5c).

In conclusion, when the NK cells incubated under fresh NK incubation conditions were administered once a week for 4 weeks at a concentration of $3 \times 10^6$ cells/mouse, these cells showed excellent anticancer effects. In addition, when the NK cells were administered twice a week for 2 weeks, the fresh NK and the 4° C. cold-preserved NK cells showed higher anticancer activities higher than the fresh NK (w/o ROSETTESEP™) and the 4° C. cold-preserved NK (w/o ROSETTESEP™) cells.

Reference Example 3: Examination of Anticancer Effect According to Freezing or not of NK Cells

Example 3-1: Examination of Tumor Volume Inhibition According to Freezing or not of NK Cells In order to examine the anticancer effect of the NK cells of the present invention according to freezing or not of the NK cells, the decrease in tumor volume was examined.

Specifically, cancer cells were transplanted into mice in the same manner as described in Experimental Example 1-1, and after 2 hours, the NK cells were administered to the mice at a concentration of $3\times10^6$ cells/mouse, and 0.2 ml of the NK cells were injected into the tail vein of each mouse. Herein, the NK cells were administered under the following conditions: fresh NK cells (once a week for 4 weeks, a total of four times), thawed cryopreserved NK cells (once a week for 4 weeks, a total of four times), thawed cryopreserved NK cells (twice a week for 4 weeks, a total of eight times), and fresh NK cells (once a week for one week) plus thawed cryopreserved NK cells (once a week for three weeks, a total of three times). Vehicle control groups were administered with 5% HAS and serum free medium, and a positive control group was administered intraperitoneally with 1 mg/kg of adriamycin at 2-day intervals (FIG. 6a).

To examine toxicity during the experimental period, the weight change and general symptoms of the mice were observed. As a result, in all the groups administered with the NK cells, a normal increase in the weight was observed without general symptoms during the experimental period, compared to the vehicle control groups. However, in the positive control group administered with adriamycin, two dead animals and a statistically significant weight decrease of 32.1% ($p<0.001$) appeared.

In addition, in order to examine the anticancer effect of the NK cells according to freezing or not of the NK cells, the change in tumor volume on day 27 was examined. As a result, as shown in FIG. 6b, the groups, administered with fresh NK cells (a total of four times), thawed cryopreserved cells (a total of eight times), and fresh NK cells (once) plus thawed cryopreserved NK cells (a total of three times), showed tumor growth inhibitions of 58.8% ($p<0.001$), 45.2% ($p<0.001$) and 19.2%, respectively, and the positive control group showed a tumor growth inhibition of 60.1% ($p<0.01$) (FIG. 6b).

3-2: Examination of Tumor Weight Decrease According to Freezing or not of NK Cells In order to examine the anticancer effect according to freezing or not of the NK cells of the present invention, the decrease in tumor weight was examined.

Specifically, cancer cells were transplanted into mice in the same manner as described in Experimental Example 1-1, and then NK cells were administered to the mice under the same conditions as described in Experimental Example 4-1. On 27 days after drug administration, the tumor was excised and weighed.

As a result, as shown in FIG. 6c, the groups, administered with fresh NK cells (a total of 4 times), thawed cryopreserved NK cells (a total of 8 times), and fresh NK cells (once) plus thawed cryopreserved NK cells (a total of 3 times), showed tumor weight decreases of 58.5% ($p<0.001$), 46.2% ($p<0.01$) and 19.5%, respectively, and the positive control group showed a tumor weight decrease of 60.5% ($p<0.05$) (FIG. 6c).

In conclusion, the above-described results indicate that, when the fresh NK cells (once a week for 4 weeks, a total of 4 times) or the thawed cryopreserved NK cells (twice a week for 4 weeks, a total of 8 times) are administered at a concentration of $3\times10^6$ cells/mouse, they show significant anticancer effects without general symptoms and toxic symptoms such as weight loss.

Reference Example 4: Examination of Anticancer Effects of NK Cells According to Freezing or not of NK Cells and the Number of Administrations of NK Cells 4-1: Examination of Tumor Volume Inhibition According to Freezing or not of NK Cells and the Number of Administrations of NK Cells In order to examine the anticancer effects of the NK cells of the present invention according to freezing or not of the NK cells and the number of administrations of the NK cells, the decrease in tumor volume was examined.

Specifically, cancer cells were transplanted into mice in the same manner as described in Experimental Example 1-1. After 2 hours, fresh NK cells and thawed cryopreserved NK cells were administered to the mice at concentrations of $3\times10^6$ cells/mouse and $6\times10^6$ cells/mouse, and 0.2 ml of the NK cells were injected into the tail vein of each mouse. Herein, the NK cells were administered under the following conditions: $3\times10^6$ fresh NK cells/mouse (once a week for 4 weeks, a total of 4 times); $6\times10^6$ fresh NK cells/mouse (once in two weeks for 4 weeks; a total of two times); and fresh NK cells ($3\times10^6$ cells/mouse; once a week for 1 week) plus thawed cryopreserved cells ($3\times10^6$ cells/mouse; twice a week for 3 weeks, a total of 6 times); thawed cryopreserved NK cells (serum free medium; twice a week for 4 weeks, a total of 8 times); and thawed cryopreserved NK cells (distilled water; twice a week for 4 weeks, a total of 8 times). Vehicle control groups were injected intravenously with the same amount of 5% HAS, serum-free medium and distilled water, respectively, and a positive control group was administered intraperitoneally with 2 mg/kg of doxorubicin HCL at 2-day intervals (FIG. 7a).

In order to examine toxicity during the experimental period, the weight change and general symptoms of the animals were observed. As a result, in all the groups injected with the NK cells, a normal increase in the weight was observed without general symptoms, compared to the vehicle control group. However, in the positive control group administered with doxorubicin HCL, two dead animals during the administration period and a statistically significant weight decrease of 25.0% ($p<0.01$) on the last day appeared.

In addition, in order to examine the anticancer effects of the NK cells according to freezing or not of the NK cells and the number of administrations of the NK cells, the change in tumor volume on day 26 was examined. As a result, as shown in FIG. 7b, the groups, administered with $3\times10^6$ fresh NK cells/mouse (a total of 4 times), $6\times10^6$ fresh NK cells/mouse (a total of two times), fresh NK cells ($3\times10^6$ cells/mouse; once) plus thawed cryopreserved NK cells ($3\times10^6$ cells/mouse; a total of 6 times), thawed cryopreserved NK cells (serum free medium; a total of 8 times), and thawed cryopreserved NK cells (distilled water; a total of 8 times), showed tumor growth inhibitions of 68.3% ($p<0.001$), 61.5% (p<0.001), 63.7% (p<0.001), 55.1% (p<0.1) and 38.8%, respectively. The positive control group administered with doxorubicin HCl showed a tumor growth inhibition of 72.9% (p<0.01) on the last day (FIG. 7b).

4-2: Examination of Tumor Weight Decrease According to Freezing or not of Cells, Number of Cells and the Number of Administrations of Cells In order to examine the anticancer effects of the NK cells of the present invention according to freezing or not of the NK cells, the number of the NK cells and the number of administrations of the NK cells, the decrease in tumor weight was examined.

Specifically, cancer cells were transplanted into mice in the same manner as described in Experimental Example 1-1, and then NK cells were administered to the mice under the same conditions as described in Experimental Example 4-1. On 26 days after drug administration, the tumor was excised and weighed. As a result, as shown in FIG. 7c, the groups, administered with $3\times10^6$ fresh NK cells/mouse (a total of 4 times), $6\times10^6$ fresh NK cells/mouse (a total of two times), fresh NK cells ($3\times10^6$ cells/mouse; once) plus thawed cryopreserved NK cells ($3\times10^6$ cells/mouse; a total of 6 times), thawed cryopreserved NK cells (serum free medium; a total of 8 times), and thawed cryopreserved NK cells (distilled water; a total of 8 times), showed tumor weight decreases of 68.6% (p<0.001), 61.8% (p<0.01), 59.1% (p<0.01), 50.2% (p<0.05) and 40.8% (p<0.05), respectively. The group administered with the positive control Doxorubicin HCl showed a tumor weight decrease of 70.4% (p<0.01) (FIG. 7c).

In conclusion, the above-described results indicated that, when fresh NK cells (once a week for 4 weeks, a total of 4 times; or once in two weeks for 4 weeks, a total of two times), thawed cryopreserved NK cells (serum free medium; twice a week for 4 weeks, a total of 8 times), and fresh NK cells (once a week for 1 week) plus thawed cryopreserved NK cells (twice a week for 3 weeks, a total of 6 times), were injected into the tail veins of each mouse at the above-described concentrations, these cells showed statistically significant excellent effects on the inhibition of tumor growth without causing general symptoms and toxic symptoms such as weight loss.

Experimental Example 5: Examination of the Anticancer Effect of NK Cells Against Lung Cancer According to the Number of NK Cells 5-1: Examination of the Effects of NK Cells on Tumor Growth Inhibition and Tumor Weight Decrease According to Number of NK Cells Using mouse models xenografted with human lung cancer NCI-H460 cells (Korea Research Institute of Bioscience and Biotechnology, Korea), the anticancer effect of the NK cells of the present invention was examined according to the number of the NK cells by intravenously injecting varying doses of the NK cells in a repeated manner.

Specifically, cancer cells were transplanted into mice in the same manner as described in Experimental Example 1-1, and when the average tumor volume reached 50.0 mm³, NK cells were injected into the mice at concentrations of $3\times10^5$, $1\times10^6$, $3\times10^6$ and $1\times10^7$ cells/mouse. 0.2 ml of the NK cells were injected into the tail vein of each mouse once a week for 4 weeks (a total of 4 times). A solvent control group was administered with 5% HSA, and a positive control group was administered intraperitoneally with 2 mg/kg of doxorubicin HCL at 2-day intervals (FIG. 8a).

In order to examine toxicity during the experimental period, the weight change and general symptoms of the mice were observed. As a result, in all the groups administered with varying doses of the NK cells, a normal increase in the weight was observed without general symptoms during the experimental period, compared to the vehicle control group. However, in the positive control group administered with doxorubicin HCL, a statistically significant weight decrease of 43.3% (p<0.001) appeared.

In order to examine the anticancer effect of the NK cells, the tumor volume was measured a total of 11 times according to the method of Experimental Example 1 during a period ranging from the day of start to the day of autopsy. On the last day (day 26), the mice were sacrificed, and the tumor was separated from the sacrificed mice, and then the volume of the tumor was measured to determine the tumor growth inhibitory effect of the NK cells. As a result, as shown in FIG. 8b, the group, administered with NK cells at a concentration of $1\times10^7$ cells/mouse, showed a significant tumor growth inhibition of 47.9% (p<0.001), compared to the vehicle control group. The groups, administered with NK cells at concentrations of $3\times10^5$, $1\times10^6$ and $3\times10^6$ cells/mouse, showed tumor growth inhibition up to 10 days after administration of the NK cells, but after 10 days, the tumor growth in these group showed a tendency to increase as the inhibition rate decreased. Furthermore, the positive control group showed a tumor growth inhibition of 53.8% (p<0.001) (FIG. 8b).

In addition, the effect of the NK cells on tumor weight decrease was examined. As a result, as shown in FIG. 8c, the group, administered with NK cells at a concentration of $1\times10^7$ cells/mouse, showed a significant tumor weight decrease of 46.5% (p<0.001), compared to the vehicle control group, and the positive control group showed a tumor weight decrease of 52.4% (p<0.001) (FIG. 8c).

5-2: Examination of NK Cell Infiltration into Tumor Tissue

In order to examine the amount of NK cells that infiltrated into tumor tissue when the NK cells were administered under the conditions described in Experimental Example 5-1, the following experiment was performed.

Specifically, mouse cancer tissue was fixed in 10% formalin solution at 4° C. for 12 hours. The fixed tissue was sectioned thinly and placed in PBS solution. For immunohistochemical staining of the NK cells, the tissue section was placed in 3% hydrogen peroxide solution for 30 minutes, and then placed in a solution containing 0.1 M PBS (pH 7.4), 0.1% triton X-100, serum bovine albumin and CD56 antibody (1:500, PharMigen, USA), followed by incubation at 4° C. for 12 hours. Thereafter, the section was incubated in a solution containing fluorescence-labeled anti-mouse IgG (1:200, PharMigen, USA) at room temperature for 1 hour, and then observed with a microscope. Alternatively, the fixed tissue was directly stained with hematoxylin and eosin and was observed with a microscope.

As a result, as shown in FIGS. 8d and 8e, when the NK cells were administered to the mice at concentrations of $3\times10^5$, $1\times10^6$ and $3\times10^6$ cells/mouse, the number of dead cancer cells (arrow) increased in a manner dependent on the number of NK cells injected (FIG. 8d), and the number of the NK cell marker CD56-positive cells (arrow) significantly increased compared to that in the normal control group administered with the vehicle, and also CD56-positive cells mainly infiltrated around cancer tissue (FIG. 8e).

In conclusion, it was shown that, when the NK cells were injected into the tail veins of the mice once a week for 4 weeks at a concentration of $1\times10^7$ cells/mouse, these NK cells showed significant tumor inhibitory effects against human lung cancer without causing general symptoms and toxic symptoms such as weight loss.

Reference Example 6: Examination of Anticancer Effects of NK Cells Against Lung Cancer, Liver Cancer and Pancreatic Cancer In order to the anticancer effects of the NK cells of the present invention against various kinds of cancer, the anticancer effects of the NK cells were examined by repeated intravenous injections into mouse models xenografted with human lung cancer A549 cells (Korea Research Institute of Bioscience and Biotechnology, Korea), liver cancer SNU-709 cells (Korea Research Institute of Bioscience and Biotechnology, Korea) and pancreatic cancer MIA-Paca-2 cells (Korea Research Institute of Bioscience and Biotechnology, Korea).

Specifically, cancer cells were transplanted into mice in the same manner as described in Experimental Example 1-1, and when the average tumor volume reached 50.0 mm$^3$, NK cells were injected into the mice at a concentration of 6×10$^6$ cells/mouse. 0.2 ml of the NK cells were injected into the tail vein of each mouse once a week for 4 weeks (a total of 4 times). A solvent control group was administered with 5% HSA (FIG. 9a).

In order to examine toxicity during the experimental period, the weight change and general symptoms of the mice were observed. As a result, in all the groups administered with varying doses of the NK cells, a normal increase in the weight was observed without general symptoms during the experimental period, compared to the vehicle control group.

In order to examine the anticancer effect of the NK cells, the tumor volume was measured a total of 11 times according to the method of Experimental Example 1 during a period ranging from the day of start to the day of autopsy. On the last day (day 25), the mice were sacrificed, and the tumor was separated from the sacrificed mice, and then the volume of the tumor was measured to determine the tumor growth inhibitory effect of the NK cells. As a result, as shown in FIG. 9b, in the lung cancer mouse models, the groups administered with umbilical cord blood-derived NK cells and peripheral blood-derived NK cells showed tumor growth inhibitions of 24.7% ($p<0.05$) and 9.0%, respectively, compared to the vehicle control group. In the liver cancer mouse models, the group administered with umbilical cord blood-derived NK cells showed a significant tumor growth inhibition of 37.7% ($p<0.01$). In the pancreatic cancer mouse models, the group administered with umbilical cord blood-derived NK cells showed a significant tumor growth inhibition of 28.2% ($p<0.01$) (FIG. 9b).

In addition, on 25 days after administration of the NK cells, the effects of the NK cells on tumor weight decrease were examined. As a result, as shown in FIG. 9c, in the lung cancer mouse models, the groups administered with umbilical cord blood-derived NK cells and peripheral blood-derived NK cells showed tumor growth inhibitions of 20.4% ($p<0.01$) and 10.8%, respectively, compared to the vehicle control group. In the liver cancer mouse models, the group administered with umbilical cord blood-derived NK cells showed a tumor weight decrease of 37.6% ($p<0.01$), and in the pancreatic cancer mouse models, the group administered with umbilical cord blood-derived NK cells showed a tumor weight decrease of 23.9% ($p<0.01$) (FIG. 9c).

In conclusion, it was shown that, when the NK cells of the present invention were injected into the tail veins of the mice once a week for 4 weeks at a concentration of 6×10$^6$ cells/mouse, these NK cells showed significant tumor inhibitory effects against human lung cancer, liver cancer and pancreatic cells without causing general symptoms and toxic symptoms such as weight loss.

Experimental Example 6: Identification of Characteristics of NK Cells According to the Present Disclosure 6.1. NK Cell Production As in Example 1 above, NK cells separated from peripheral blood were used in the experiment.

Comparative Example 6.1. Peripheral Blood-Derived NK Cell Production

In one example, the general NK cell derived from peripheral blood was produced via the following production process. Peripheral blood was diluted at a ratio 2:1 with RPMI 1640 and after carefully placing the prepared blood on a top layer of the Ficoll-Paque, the blood was centrifuged at 2,000 rpm for 30 minutes to obtain a mononuclear cell layer (MNC layer). Monocytes were obtained by removing erythrocytes from cells carefully taken from the MNC layer. After labeling the monocytes by adding CD56 microbeads (Miltenyi Biotech) to the obtained monocytes, a CS column and Vario MACS were used to remove CD56 negative cells from the monocytes to obtain CD56 positive cells. Specifically, the CD56 microbeads (Miltenyi Biotech) captures the CD56 positive cells from the monocytes and makes them magnetic. Then, the CD56 positive cells having the microbeads attached thereto among the monocytes passed through the MACS column reacting with the magnet, such that the CD56 positive cells remained in the column and the CD56 negative cells exited and separated from the column. This produced the conventional NK cell that is separated from the peripheral blood.

6.2. Identification of Changes in Natural Killer Cell Receptor Expression

In order to determine the difference in activity of natural killer cells between Example 6.1 and Comparative Example 6.1, representative natural killer cell receptor expression levels were analyzed by FACS, and the results are shown in FIGS. 10 and 11.

As shown in FIG. 10 and FIG. 11, it may be confirmed from the expression level of CD56 and CD16 that NK cells (KRIBB-NK cells) according to the present disclosure were differentiated into natural killer cells with high purity as in the peripheral blood-derived NK cells (PB-NK cells).

Meanwhile, NK cells (KRIBB-NK cells) according to the present disclosure showed expression levels of activating receptors such as NKG2D, NKp46, NKp44 and NKp30 which are involved in the NK cell activity significantly higher than that of the general NK cells derived from peripheral blood. NK cells (KRIBB-NK cells) according to the present disclosure showed expression levels of the receptors such as KIR2DL2/3 and KIR3DL1 which are involved in the suppression of NK cell activity significantly lower than that of the general NK cells derived from peripheral blood.

In other words, the NK cells produced by the production method according to the present disclosure have different characteristics from the peripheral blood-derived NK cells generally known in the art. In particular, the NK cells produced by the production method according to the present disclosure exhibited the increase in the expression of the receptors to induce NK cell activity and the decrease in the expression of the receptors to suppress the NK cell activity that may enhance the functionality thereof.

The above results are shown in detail in FIG. 11. Specific increase or decrease percentage thereof is easily calculated based on the numerical value, and may be included within the scope of the present specification.

As may be seen in FIG. 11, each of the percentages of CD56 and CD16 positive cells that may indicate the degree of natural killer cell differentiation in NK cells (KRIBB-NK cells, average results of 3 lots) according to the present disclosure is substantially similar to that in the peripheral blood-derived NK cells (PB-NK cell) (CD56+ cell percentage=96.0%:94.9%, CD16+ cell percentage=43.0%:48.0%). Further, KRIBB-NK cells have 1.2 to 84 times higher expression levels of NKG2D and NCRs (NKp30, NKp44, NKp46) as representative receptors to induce the NK cell activity than those in PB-NK cells. KRIBB-NK cells have about 1.3 times higher expression level of NKp30 than that in PB-NK cells. KRIBB-NK cells have about 84 times higher expression level of NKp46 than that in PB-NK cells.

In contrast, KRIBB-NK cells have 34% lower KIR2D2/3 and KIR3DL1 expression levels than those in PB-NK cells in which the KIR2D2/3 and KIR3DL1 are representative receptors to inhibit the NK cell activity. The increase in the natural killer cell activating receptor and the decrease in the NK cell inhibitory receptor may be achieved by the NK cell according to the present disclosure. Thus, the NK cell according to the present disclosure exhibits different characteristics from the known NK cell and shows the result that the natural killer cell receptor is modulated to increase the functionality of the NK cell.

Experimental Example 7: Identification of Killing Ability of NK Cells According to the Present Disclosure In order to identify the killing ability of the natural killer cells as produced in Example 6.1 and Comparative Example 6.1, experiments were performed.

K562 cell line as a representative blood cancer cell line was stained with caclein-AM and reacted with natural killer cells for 4 hours. Then, direct killing ability of K562 cell line was identified.

The results are shown in FIG. 12.

As seen in FIG. 12, when a ratio of the effector and target is 10:1, the killing ability of K562 cells was about 4 times higher in the KRIBB-NK cells (average of 3 lots) than that in the peripheral blood-derived general NK cells. Even as a result of reducing the ratio of the effector, this was confirmed that the killing ability of NK cells according to the present disclosure was about 5 to 8 times higher than that of the peripheral blood-derived general NK cells. That is, the functional NK cell as activated in the present disclosure has an excellent effect on killing ability via the appropriate NK cell receptor expression change.

Experimental Example 8: Identification of IFN-γ Secretion Ability of NK Cells According to the Present Disclosure Changes in the characteristics of natural killer cells as produced in accordance with the present disclosure were checked by identifying changes in the expression level of IFN-γ which the natural killer cell produces and secretes to suppress the proliferation of cancer cells and virally infected cells.

The results are shown in FIG. 13.

As shown in FIG. 13, IFN-γ which the natural killer cell produces and secretes to inhibit the proliferation of cancer cells and virally infected cells is detected at 12.6 times higher amount in the NK cells (average results of KIRBB-NK cells 3 lots) according to the present disclosure than that in the general NK cells (PB-NK) as the peripheral blood-derived NK cells.

As described above, the general natural killer cells (PB-NK cells) isolated from peripheral blood had significantly lower killing ability and IFN-γ producing ability against cancer cells. These results show that the NK cells produced by the conventional method of separating the NK cells were not functionally improved.

However, the functionality of NK cells according to the present disclosure is maximized via culturing thereof in the medium containing the appropriate cytokines IL-15 and IL-21 that may maximize the functionality of NK cells. Thus, NK cells according to the present disclosure have NK cell receptor expression ability different from that of the known NK cells. In particular, changes in the expression of receptors to induce the NK cell activity due to the stimulation based differentiation before the NK cell encounters the target cells may enhance the killing ability and IFN-γ producing ability against cancer cells to significantly enhance the functionality of NK cells.

When considering these results, the NK cell according to the present disclosure exhibits an expression pattern of NK cell receptor different from that of the known cells. Accordingly, the NK cell according to the present disclosure has the advantage that the NK cell according to the present disclosure may exhibit an excellent anti-cancer effect as functionally enhanced NK cells.

What is claimed is:

1. A method for treating cancer in a subject in need thereof, the method comprising administering to the subject natural killer cells having the following characteristics:
   a) an increase in expression of NKG2D, NKp30, NKp44, and NKp46 as compared to a natural killer cells isolated from peripheral blood; and
   b) a decrease in expression of KIR2DL2/3, and KIR3DL1 as compared to a natural killer cells isolated from peripheral blood;
   wherein the natural killer cells administered are produced by a process comprising:
   1) obtaining CD3-negative cells by removing CD3-positive T cells from monocytes by allowing the CD3-positive T cells to crosslink to erythrocytes and then isolating the CD3-negative cells by density-gradient centrifugation; and
   2) obtaining cultured CD3-negative cells by culturing the CD3-negative cells of step 1) with IL-15 and IL-21, wherein the culturing does not comprise treating with cytokines other than IL-15 and IL-21, and wherein the culturing is performed for 10-24 days;
   3) obtaining cryopreserved NK cells by freezing the cultured CD3-negative cells of step 2) in a cryopreservation medium containing a cryoprotective agent and 10% DMSO (dimethyl sulfoxide) under serum-free, protein-free and animal component-free conditions for 2 months or less, wherein the freezing is performed by stepwise cooling from −70° C. to −200° C.; and
   4) quick thawing the cryopreserved NK cells at 37° C., and washing out the cryopreservation medium.

2. The method of claim 1, wherein the increase in the expression of NKG2D, NKp30, NKp44, and NKp46 is greater by at least 5% than the increase thereof in the natural killer cells isolated from peripheral blood.

3. The method of claim 1, wherein the decrease in expression of KIR2DL2/3 and KIR3DL1 is greater by at least 5% than the decrease thereof in the natural killer cells isolated from peripheral blood.

4. The method of claim 1, wherein the natural killer cells have a killing ability against cancer cells greater than the killing ability of the natural killer cells isolated from peripheral blood.

5. The method of claim 1, wherein the cancer includes one selected from a group consisting of colorectal cancer, lung cancer, liver cancer, pancreatic cancer and leukemia.

6. The method of claim 1, wherein the natural killer cells are administered once a week for four weeks or are administered twice a week for two weeks.

7. The method of claim 1, wherein $1\times10^5$ to $1\times10^{10}$ natural killer cells are administered.

* * * * *